United States Patent [19]

Takaya et al.

[11] 4,452,851

[45] Jun. 5, 1984

[54] CEPHEM COMPOUNDS

[75] Inventors: Takao Takaya, Kawanishi; Hisashi Takasugi, Osaka; Hideaki Yamanaka, Hirakata, all of Japan

[73] Assignee: Fujisawa Pharmaceutical Co., Ltd., Osaka, Japan

[21] Appl. No.: 343,243

[22] Filed: Jan. 27, 1982

[30] Foreign Application Priority Data

Feb. 2, 1981 [GB] United Kingdom ............... 8103081
Mar. 20, 1981 [GB] United Kingdom ............... 8108884

[51] Int. Cl.³ ............... C07D 501/36; A61K 31/545
[52] U.S. Cl. ........................... 424/246; 544/22; 544/29; 544/16
[58] Field of Search .............. 544/16, 26, 22, 27, 544/28; 424/246

[56] References Cited

U.S. PATENT DOCUMENTS

| | | | |
|---|---|---|---|
| 4,123,528 | 10/1978 | Cama et al. | 544/26 |
| 4,150,156 | 4/1979 | Beattie et al. | 544/29 |
| 4,256,739 | 3/1981 | Woodward et al. | 544/29 |
| 4,288,434 | 9/1981 | Heymes | 424/246 |
| 4,307,090 | 12/1981 | Vignav et al. | 424/246 |
| 4,374,834 | 2/1983 | Heymes et al. | 424/246 |

FOREIGN PATENT DOCUMENTS 2555858 6/1976 Fed. Rep. of Germany .
2805655 8/1978 Fed. Rep. of Germany .
2812570 9/1978 Fed. Rep. of Germany .

*Primary Examiner*—Nicholas S. Rizzo
*Attorney, Agent, or Firm*—Oblon, Fisher, Spivak, McClelland & Maier

[57] ABSTRACT

This invention relates to novel cephem compounds of high antimicrobial activity of the formula:

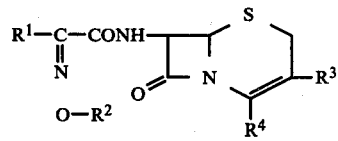

wherein $R^1$ is amino substituted thiazolyl selected from the group consisting of 2-aminothiazol-4-yl, 2-aminothiazol-5-yl, 4-aminothiazol-2-yl, 2-amino-5-halothiazol-4-yl, 2-amino-4-halothiazol-5-yl, and 4-amino-5-halothiazol-2-yl,
  protected amino substituted thiazolyl selected from said group,
  lower alkylamino substituted thiazolyl,
  amino substituted thiadiazolyl,
  protected amino substituted thiadiazolyl,
  amino substituted pyridyl,
  protected amino substituted pyridyl,
  furyl,
  thiazolyl,
  thiadiazolyl,
  phenyl, or
  naphthyl,
$R^2$ is carboxy(lower)alkyl or protected carboxy(lower)alkyl,
$R^3$ is lower alkylthio, and
$R^4$ is carboxy or protected carboxy, and pharmaceutically acceptable salts thereof.

34 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms, especially for oral administration.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

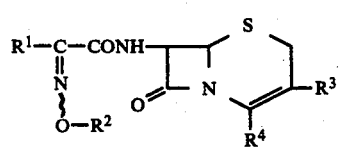

(I)

wherein
R$^1$ is amino substituted thiazolyl which may have halogen(s), protected amino substituted thiazolyl which may have halogen(s), lower alkylamino substituted thiazolyl, amino substituted thiadiazolyl, protected amino substituted thiadiazolyl, amino substituted pyridyl, protected amino substituted pyridyl, furyl, thiazolyl, thiadiazolyl, phenyl, or naphthyl,
R$^2$ is carboxy(lower)alkyl or protected carboxy(lower)alkyl,
R$^3$ is lower alkylthio, and
R$^4$ is carboxy or protected carboxy.

According to the present invention, the new cephem compounds (I) can be prepared by various processes which are illustrated in the following schemes.

Process 1

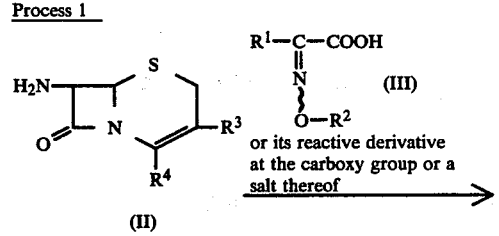

(II)
or its reactive derivative at the amino group or a salt thereof

-continued

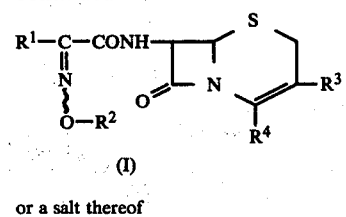

(I)
or a salt thereof

Process 2

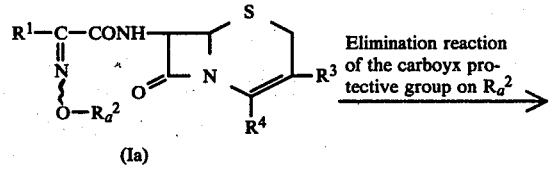

(Ia)
or a salt thereof

Elimination reaction of the carboyx protective group on R$_a$$^2$

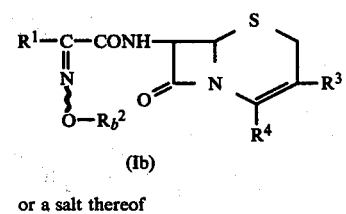

(Ib)
or a salt thereof

Process 3

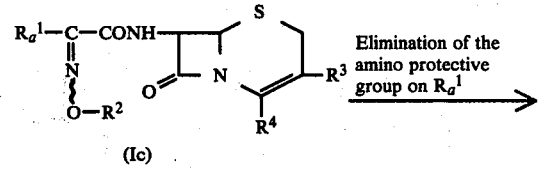

(Ic)
or a salt thereof

Elimination of the amino protective group on R$_a$$^1$

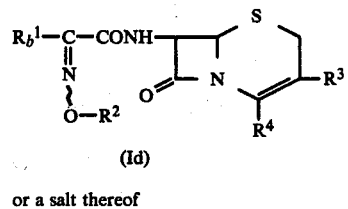

(Id)
or a salt thereof

Process 4

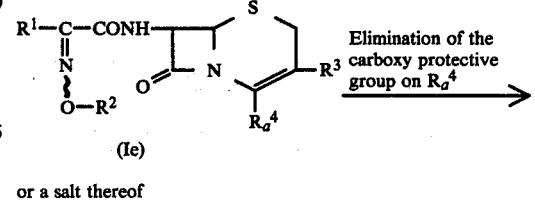

(Ie)
or a salt thereof

Elimination of the carboxy protective group on R$_a$$^4$

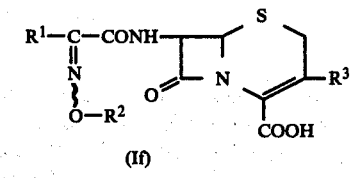

(If)
or a salt thereof

Process 5

-continued

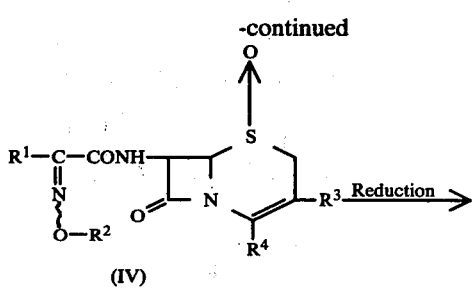
(IV)
or a salt thereof

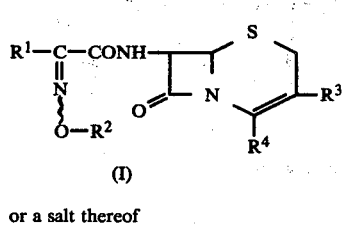
(I)
or a salt thereof

Process 6

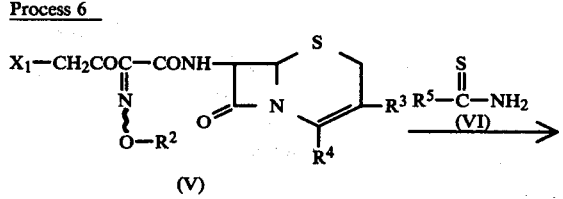
(V)
or a salt thereof

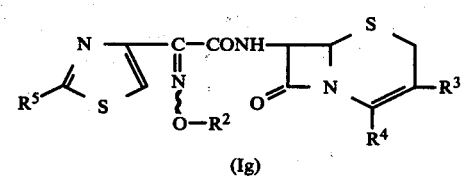
(Ig)
or a salt thereof

Process 7

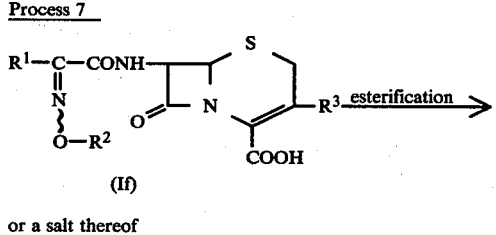
(If)
or a salt thereof

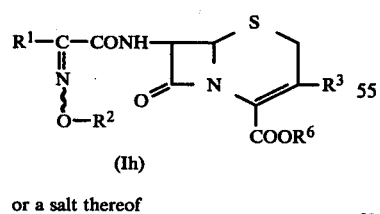
(Ih)
or a salt thereof wherein
R¹, R², R³ and R⁴ are each as defined above,
$R_a^1$ is protected amino substituted thiazolyl which may have halogen(s), protected amino substituted thiadiazolyl or protected amino substituted pyridyl, $R_b^1$ is amino substituted thiazolyl which may have halogen(s), amino substituted thiadiazolyl or amino substituted pyridyl, $R_a^2$ is protected carboxy(lower)alkyl, $R_b^2$ is carboxy(lower)alkyl, $R_a^4$ is protected carboxy, R⁵ is amino, protected amino or lower alkylamino, R⁶ is ester moiety of esterified carboxy represented by a group of the formula: —COOR⁶, and X₁ is halogen.

Among the starting compounds in the present invention, the compounds (IV), (V) and some of the compound (III) are novel and can be prepared by the processes which are illustrated in the following schemes.

Process A

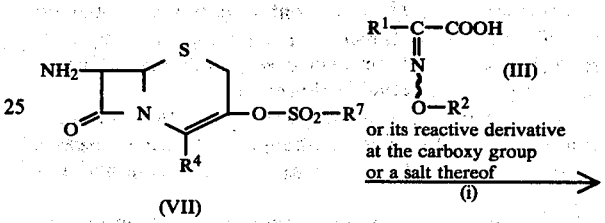
(VII)
or its reactive derivative
at the amino group
or a salt thereof (III) or its reactive derivative at the carboxy group or a salt thereof
(i)

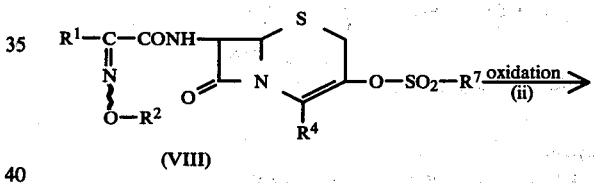
(VIII)
or a salt thereof oxidation
(ii)

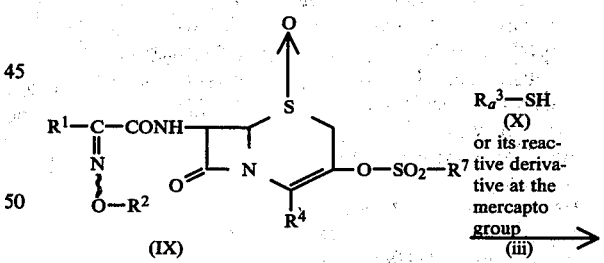
(IX)
or a salt thereof $R_a^3$—SH
(X)
or its reactive derivative at the mercapto group
(iii)

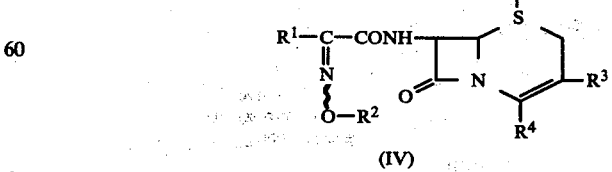
(IV)
or a salt thereof

Process B

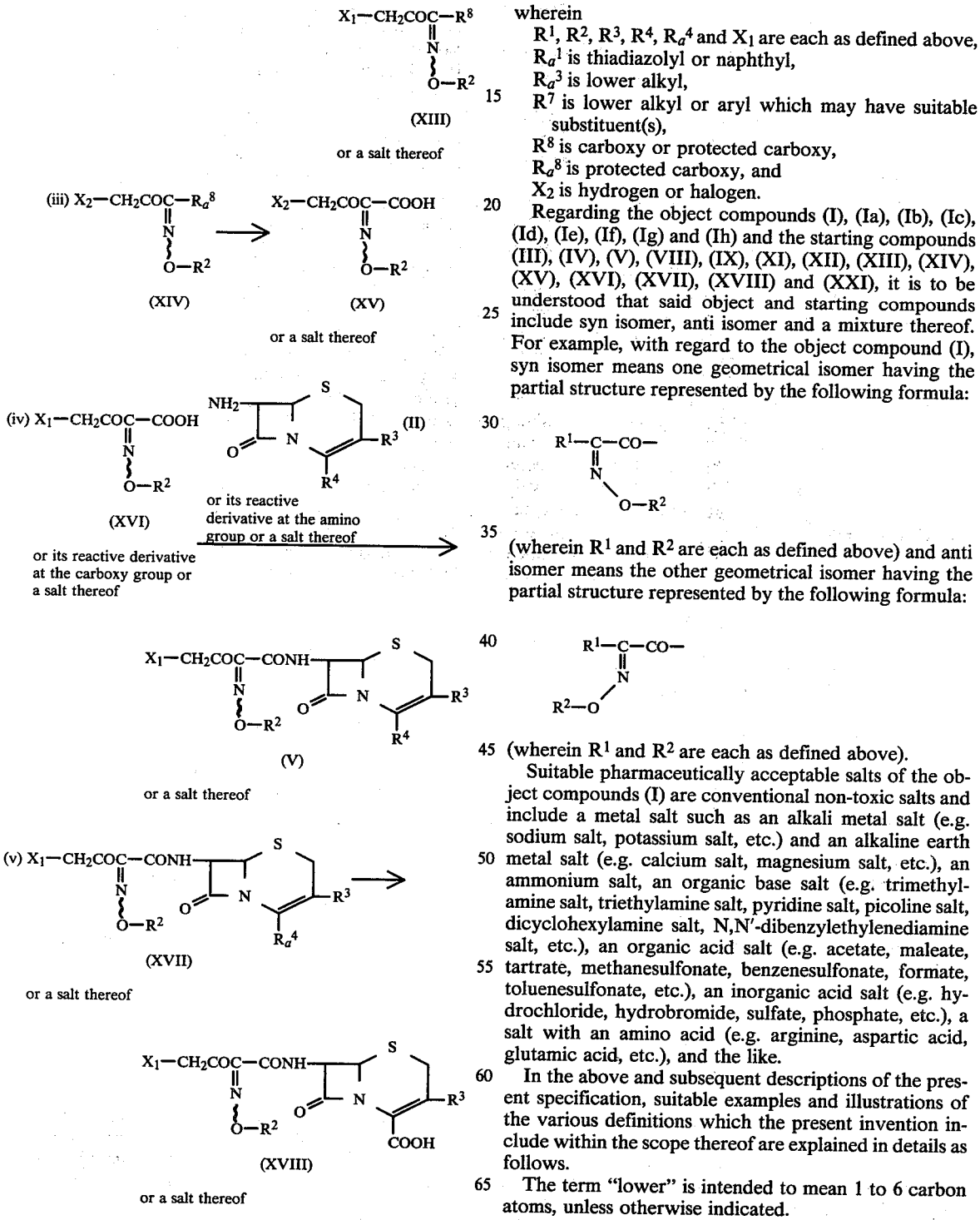

Process C wherein
R[1], R[2], R[3], R[4], $R_a{}^4$ and $X_1$ are each as defined above,
$R_a{}^1$ is thiadiazolyl or naphthyl,
$R_a{}^3$ is lower alkyl,
R[7] is lower alkyl or aryl which may have suitable substituent(s),
R[8] is carboxy or protected carboxy,
$R_a{}^8$ is protected carboxy, and
$X_2$ is hydrogen or halogen.

Regarding the object compounds (I), (Ia), (Ib), (Ic), (Id), (Ie), (If), (Ig) and (Ih) and the starting compounds (III), (IV), (V), (VIII), (IX), (XI), (XII), (XIII), (XIV), (XV), (XVI), (XVII), (XVIII) and (XXI), it is to be understood that said object and starting compounds include syn isomer, anti isomer and a mixture thereof. For example, with regard to the object compound (I), syn isomer means one geometrical isomer having the partial structure represented by the following formula:

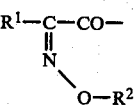

(wherein R[1] and R[2] are each as defined above) and anti isomer means the other geometrical isomer having the partial structure represented by the following formula:

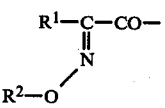

(wherein R[1] and R[2] are each as defined above).

Suitable pharmaceutically acceptable salts of the object compounds (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "amino substituted thiazolyl which may have halogen(s)" may include 2-aminothiazol-4-yl, 2- aminothiazol-5-yl, 2-amino-5-halothiazol-4-yl (e.g. 2-amino-5-chlorothiazol-4-yl, 2-amino-5-bromothiazol-4-yl, etc.), 4-aminothiazol-2-yl, and the like.

Suitable "lower alkylamino substituted thiazolyl" may include 2-(lower alkylamino)thiazol-4-yl, 2-(loweralkylamino)thiazol-5-yl, 4-(lower alkylamino)thiazol-2-yl, and the like, wherein the lower alkyl moiety is as defined below.

Suitable "amino substituted thiadiazolyl" may include 5-amino-1,2,4-thiadiazol-3-yl, 5-amino-1,3,4-thiadiazolyl-2-yl, 4-amino-1,2,5-thiadiazol-3-yl, and the like.

Suitable "thiadiazolyl" may include 1,2,4-thiadiazol-3-yl, 1,3,4-thiadiazol-2-yl, 1,2,5-thiadiazol-3-yl and the like.

Suitable "amino substituted pyridyl" may include 3(or 4 or 5 or 6)-aminopyridin-2-yl, 2(or 4 or 5 or 6)-aminopyridin-3-yl, 2(or 3)-aminopyridin-4-yl, and the like.

Suitable "protected amino" and "protected amino" moiety in the terms "protected amino substituted thiazolyl which may have halogen(s)", "protected amino substituted thiadiazolyl" and "protected amino substituted pyridyl" may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acy moiety as stated above may have at least one suitable substituent(s) such as halogen (chlorine, bromine, fluorine and iodine) or the like.

Preferable examples of "protected amino substituted thiazolyl which may have halogen(s)" may include acylaminothiazolyl which may have halogen(s) such as 2-lower alkanamidothiazolyl [e.g. 2-formamidothiazol-4-yl, etc.], 2-lower alkanamido-5-halothiazolyl [e.g. 2-formamido-5-bromothiazol-4-yl, 2-formamido-5-chlorothiazol-4-yl, etc.], and the like.

Preferable examples of "protected amino substituted thiadiazolyl" may include acylaminothiadiazolyl such as lower alkanamidothiadiazolyl [e.g. 5-formamido-1,2,4-thiadiazol-2-yl, etc.], and the like.

Preferable examples of "protected amino substituted pyridyl" may include acylaminopyridyl such as lower alkanamidopyridyl [e.g. 6-formamidopyridin-2-yl, etc.], and the like.

Suitable "protected carboxy" and "protected carboxy moiety" in the term "protected carboxy(lower)alkyl" may include an esterified carboxy and the like.

Suitable examples of the ester moiety in said esterified carboxy and ester moiety of esterified carboxy represented by a group of the formula: —COOR$^6$ may be the ones such as lower alkyl ester (e.g. methyl ester, ethyl ester propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s), (e.g. phenyl ester, 4-chlorophenyl ester, tolyl ester, tert-butylphenyl ester, xylyl ester, mesityl ester, cumenyl ester, etc.); phthalidyl ester: and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.), lower alkanoyloxy(lower)alkoxycarbonyl [e.g., acetoxymethoxycarbonyl, pivaloyloxymethoxycarbonyl, hexanoyloxymethoxycarbonyl, 1(or 2)-propionyloxyethoxycarbonyl, etc.]; phenyl(lower)alkoxycarbonyl (e.g. benzyloxycarbonyl, benzhydryloxycarbonyl, etc.) which may have a nitro group, lower alkoxycarbonyloxy(lower)alkoxycarbonyl (e.g. methoxycarbonyloxymethoxycarbonyl, 1-ethoxycarbonyloxyethoxycarbonyl, 1-isopropoxycarbonyloxyethoxycarbonyl, etc.), and (5-lower alkyl-2-oxo-1,3-dioxol-4-yl)(lower)alkoxycarbonyl [e.g. (5-methyl-2-oxo-1,3-dioxol-4-yl)methoxycarbonyl, etc.].

Suitable "lower alkyl" and "lower alkyl moiety" in the terms "carboxy(lower)alkyl", "protected carboxy(lower)alkyl", "lower alkylamino substituted thiazolyl" and "lower alkylamino" may include straight or branched one, having 1 to 6 carbon atom(s), such as methyl, ethyl, propyl, isopropyl, butyl, t-butyl, pentyl, hexyl or the like.

Preferable examples of carboxy(lower)alkyl may include carboxymethyl, 1-carboxyethyl, 2-carboxyethyl, 1-carboxypropyl, 2-carboxypropyl, 3-carboxypropyl, 4-carboxybutyl, 5-carboxypentyl, 6-carboxyhexyl, 1-carboxyisopropyl, 1-ethyl-1-carboxyethyl, 2-methyl-2-carboxypropyl, 1-methyl-1-carboxyethyl, and the like.

Preferable examples of protected carboxy(lower)alkyl may include esterified carboxy(lower)alkyl, and more preferably lower alkoxycarbonyl(lower)alkyl (e.g. methoxycarbonylmethyl, ethoxycarbonylmethyl, propoxycarbonylmethyl, tert-butoxycarbonylmethyl, 2-ethoxycarbonylethyl, 2-ethoxycarbonylpropyl, 4-ethoxycarbonylbutyl, 1-tert-butoxycarbonylisopropyl, 1-tert-butoxycarbonylethyl, 1-tert-butoxycarbonyl-1-methylpropyl, 4-tert-butoxycarbonylbutyl, 5-tert-butoxycarbonylpentyl, 6-butoxycarbonylhexyl, etc), phenyl(lower)alkoxycarbonyl(lower)alkyl (e.g., benzyloxycarbonylmethyl, benzhydryloxycarbonylmethyl, etc.), lower alkanoyloxy(lower)alkoxycarbonyl(lower)alkyl [e.g. acetoxymethoxycarbonylmethyl, pivaloyloxymethoxycarbonylmethyl, 1-(or 2)-pivaloyloxymethoxycarbonylethyl, 1-(or 2 or 3)-hexanoyloxymethoxycarbonylpropyl, 1-(or 2)-propionyloxyethoxycarbonylmethyl, etc.], and lower alkoxycarbonyloxy(lower)alkoxycarbonyl(lower)alkyl [e.g. methoxycarbonyloxymethoxycarbonylmethyl, 1-ethoxycarbonyloxyethoxycarbonylmethyl, 1-(or 2 or 3)-(1-isopropoxycarbonyloxyethoxycarbonyl)propyl, etc.].

Suitable "lower alkylthio" may include methylthio, ethylthio, propylthio, isopropylthio, butylthio, isobutylthio, tert-butylthio, pentylthio, hexylthio and the like, and preferably methylthio, ethylthio, and propylthio.

Suitable "halogen" may include chlorine, bromine, fluorine and iodine.

Suitable "aryl moiety" in the terms "aryl which may have suitable substituent(s)" may include phenyl, naphthyl, tolyl, xylyl, mesityl and the like.

Suitable substituent(s) on said aryl may include lower alkyl as defined above, halogen as defined above, nitro and the like.

Preferable examples of "aryl having suitable substituent(s)" may include aryl having lower alkyl.

The processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

Process 2

The object compound (Ib) or a salt thereof can be prepared by subjecting the compound (Ia) or a salt thereof to elimination reaction of the carboxy protective gorup on $R_a^2$.

Suitable salt of the compound (Ia) can be referred to the one exemplified for the compound (I).

The present elimination reaction can be carried out in a similar manner to that of aforementioned Process 4.

The present invention includes, within its scope, the cases that another protected carboxy and/or protected amino group(s) are converted into the corresponding amino free carboxy and/or amino group(s) during the reaction or the post-treating step of the present process.

Process 3

The object compound (Id) or a salt thereof can be prepared by subjecting the compound (Ic) or a salt thereof to elimination reaction of the amino protective group on $R_a^1$.

Suitable salt of the compound (Ic) can be referred to the metal salt, ammonium salt and organic amine salt exemplified for the compound (II).

The elimination reaction is carried out in accordance with a conventional method such as hydrolysis; reduction; a method treating the compound (Ic) wherein protected amino moiety in $R_a^1$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like.

Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitable be selected in accordance with the kind of the amino protective group and the elimination method as mentioned above, and the reaction is preferably carried out under a mild condition such as under cooling or at slightly elevated temperature.

The present invention includes, within its scope, the cases that another protected amino and/or protected carboxy group(s) are converted into the corresponding free amino and/or the free carboxy group(s) during the reaction or the post-treating step of the present process.

Process 4

The object compound (If) or a salt thereof can be prepared by subjecting the compound (Ie) or a salt thereof to elimination reaction of the carboxy protective group on $R_a^4$.

Suitable salt of the compound (Ie) can be referred to the acid addition salt exemplified for the compound (II).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitable be selected in accordance with the kind of the carboxy protective group and the elimination method.

The elimination using Lewis acid is preferable to eliminate substituted or unsubstituted ar(lower)alkyl ester and carried out by reacting the compound (Ie) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium carbon, Raney nickel, etc.).

The present elimination reaction of the carboxy protective group includes, within its scope, the cases that another protected carboxy and/or protected amino group(s) are converted into the corresponding free carboxy and/or amino group(s) during the reaction or the post-treating step of the present process.

Process 5

The compound (I) or a salt thereof can be prepared by reducing the compound (IV) or a salt thereof.

Suitable salts of the compound (IV) can be referred to the ones as exemplified for the compound (I).

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, dimethylformamide benzene, hexane, chloroform, methylene chloride, ethylene chloride, tetrahydrofuran, ethyl acetate, or any other solvents which do not adversely affect the reaction.

The reaction temperature is not critical and the reaction is usually carried out under cooling or at ambient temperature.

Process 6

The compound (Ig) or a salt thereof can be prepared by reacting the compound (V) or a salt thereof with a thiourea compound (VI).

The present reaction is preferably carried out in the presence of a base such as an inorganic base or an organic base, for example, alkali metal acetate, alkali metal carbonate, alkali metal alkoxide, trialkylamine or the like.

The reaction is usually conducted in a solvent such as water, alcohol (e.g., methanol, ethanol, etc.), benzene, acetone, N,N-dimethylformamide, tetrahydrofuran, diethyl ether, dioxane or any other solvent which does not adversely influence the reaction.

The reaction temperature is not critical and the reaction may be preferably carried out within a temperature range of ambient temperature to heating.

Process 7

The object compound (Ih) or a salt thereof can be prepared by subjecting the compound (If) or a salt thereof to esterification.

Suitable salt of the compound (If) can be referred to the ones as exemplified for the compound (II).

The present reaction may be carried out by reacting the compound (If) or a salt thereof with esterifying agent.

Suitable esterifying agent may be a compound of the formula:

$$X^3\text{-}R^6$$

wherein
$R^6$ is as defined above, and
$X^3$ is hydroxy or its reactive derivative.

Suitable reactive derivative of hydroxy for $X^3$ may include an acid residue such as aforesaid halogen or the like.

The present reaction is usually carried out in a solvent such as dimethylformamide, pyridine, hexamethylphosphoric triamide, dimethylsulfoxide or any other solvent which does not adversely affect the reaction.

In case that the compound (If) is used in a form of free acid, the reaction is preferably carried out in the presence of a base as mentioned above.

The reaction temperature is not critical and the reaction is preferably carried out under cooling, at ambient temperature or under warming.

The present esterification reaction includes, within its scope, the case that another free carboxy group in the compound (If) is transformed into esterified carboxy group according to reaction conditions and kinds of the protective groups in the course of the reaction and/or in posttreatment of the reaction.

The present invention includes, within its scope, the cases that the one type of tautomeric isomers is converted into the other type of isomer during the reaction and/or the post-treating step of the each process.

In case that the object compound (I) is obtained in a form of the free acid at the 4-position and/or the oxime portion and/or in case that the compound (I) has free amino group, it may be transformed into its pharmaceutically acceptable salt as aforementioned by a conventional method.

The processes for preparing the starting compounds of the present invention are explained in details in the following.

Process A

(i): (VII)+(III)→(VIII)

The compound (VIII) or a salt thereof can be prepared by reacting the compound (VII) or its reactive derivative at the amino group or a salt thereof with the compound (III) or its reactive derivative at the carboxy group or a salt thereof.

The present reaction can be carried out in a similar manner to that of aforementioned Process 1.

(ii): (VIII)→(IX)

The compound (IX) or a salt thereof can be prepared by oxidizing the compound (VIII) or salt thereof.

Suitable salts of the compound (VIII) can be referred to the ones exemplified for the compound (I).

The present oxidation reaction can be carried out by a conventional method which is applied for the transformation of —S— into

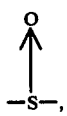

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitril, chloroform, methylene chloride, tetrahydrofuran, ethyl acetate or any other solvents which do not adversely affect the reaction.

The reaction temperature is not critical and the reaction is preferably carried out under cooling or at ambient temperature.

(iii): (IX)+(X)→(IV)

The compound (IV) or a salt thereof can be prepared by reacting the compound (IX) or a salt thereof with the compound (X) or its reactive derivative at the mercapto group.

Suitable salts of the compound (IX) can be referred to the ones exemplified for the compound (I).

Suitable reactive derivative at the mercapto group in the compound (X) may include a metal salt such as an alkali metal salt (e.g. sodium salt, potassium salt, etc.), an alkaline earth metal salt (e.g., magnesium salt, etc.) or the like.

The reaction is usually carried out in a solvent such as acetone, chloroform, nitrobenzene, methylene chloride, ethylene chloride, dimethylformamide, ether, tetrahydrofuran or any other conventional solvents which do not adversely influence the reaction, preferably in ones having strong polarity, which may be used as a mixture with water.

When the compound (X) are used in free form in the reactions, the reaction is preferably carried out in the presence of a base such as alkali metal hydroxide, alkali metal carbonate, alkali metal bicarbonate, trialkylamine, pyridine, or a Lewis acid such as boron trifluoride or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

Process B

(i): (XI)→(XII)

The compound (XII) or a salt thereof can be prepared by reacting the compound (XI) or a salt thereof with an etherifying agent.

Suitable salts of the compound (XI) can be referred to the metal salt or salt with base as exemplified for the compound (I).

The etherifying agent may include a compound of the formula:

$$R^2\text{-}X^4$$

wherein
R$^2$ is as defined above, and
X$^4$ is halogen.

The reaction is usually carried out in a solvent such as water, acetone, ethanol, diethyl ether, dimethylformamide or any other solvent which does not adversely influence the reaction, within a temperature range of cooling to heating, preferably in the presence of a base such as an inorganic or organic base, for example, alkali metal carbonate, alkali metal bicarbonate, tri(lower)alkylamine, pyridine or the like.

(ii): (XII)→(XIII)

The compound (XIII) or a salt thereof can be prepared by reacting the compound (XII) or a salt thereof with a halogenating agent.

Suitable salts of the compound (XII) can be referred to the metal salt or salt with base as exemplified for the compound (I).

The suitable halogenating agent may be halogen (e.g., bromine, chlorine, etc.), sulfuryl halide (e.g., sulfuryl bromide, sulfuryl chloride, etc.), N-halosuccinimide (e.g., N-bromosuccinimide, etc.) or the like.

The reaction is usually carried out in a solvent such as acetone, diethyl ether, N,N-dimethylformamide, tetrahydrofuran, ethyl acetate, acetic acid or any other solvent which does not adversely influence the reaction. The reaction temperature is not critical and the reaction may be preferably conducted within a temperature range of cooling to somewhat elevated temperature.

(iii): (XIV)→(XV), V): (XVII)→(XVIII)

The compound (XV) or a salt thereof and the compound (XVIII) or a salt thereof can be prepared by subjecting the compound (XIV) or a salt thereof and the compound (XVII) or a salt thereof to elimination reaction of the carboxy protective group, respectively.

The present reaction can be carried out in a similar manner to that of aforementioned Process 4.

(iv): (XVI)+(II)→(V)

The compound (V) or a salt thereof can be prepared by reacting the compound (XVI) or its reactive derivative at the carboxy group or a salt thereof with the compound (II) or its reactive derivative at the amino group or a salt thereof.

The present reaction can be carried out in a similar manner to that of aforementioned Process 1.

Process C: (XIX)+(XX)→(XXI)

The compound (XXI) or a salt thereof can be prepared by reacting the compound (XIX) or a salt thereof with the compound (XX) or a salt thereof.

Suitable salts of the compound (XIX) can be referred to the metal salt or salts with base as exemplified for the compound (I).

Suitable salts of the compound (XX) can be referred to the acid salts as exemplified for the compound (I).

The reaction is usually conducted in a conventional solvent such as water, alcohol, tetrahydrofuran, acetonitrile, dimethylsulfoxide, pyridine or any other solvent which does not adversely influence the reaction, or a mixture thereof, and the reaction temperature is not critical, and the reaction is preferably carried out under a mild condition, for example, under cooling to ambient temperature.

In case that a salt of the compound (XX) is used as a reagent, the reaction is preferably conducted in the presence of a conventional base such as pyridine, alkali metal carbonate or tri(lower)alkylamine.

The object compounds (I) and pharmaceutically acceptable salt thereof of the present invention are novel compounds which exhibit high antibacterial activity and inhibit the growth of a wide variety of pathogenic microorganisms including Gram-positive and Gram-negative bacteria and are useful as antimicrobial agents, especially for oral administration. For therapeutic purpose, the compounds according to the present invention can be used in the form of conventional pharmaceutical preparation which contain said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, ointments or suppositories, solutions, suspension, emulsions, and the like. If desired, there may be included in the above preparations auxiliary substances, stabilizing agents, wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities, urinary excretions and biliary excretions of some representative compounds of the present invention are shown below.

[1] Minimal inhibitory concentrations

(A) Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of $\mu g/ml$ after incubation at 37° C. for 20 hours.

(B) Test Compounds (1) 7-[2-(2-aminothiazol-4-yl)-2-carboxymethoxyiminoacetamido]-3-methylthio-3-cephem-4-carboxylic acid (syn isomer).

(2) 7-[2-(2-aminothiazol-4-yl)-2-carboxymethoxyiminoacetamido]-3-ethylthio-3-cephem-4-carboxylic acid (syn isomer).

(3) 7-[2-(2-amino-5-chlorothiazol-4-yl)-2-carboxymethoxyiminoacetamido]-3-ethylthio-3-cephem-4-carboxylic acid (syn isomer).

(4) 7-[2-(5-amino-1,2,4-thiadiazol-3-yl)-2-carboxymethoxyiminoacetamido]-3-ethylthio-3-cephem-4-carboxylic acid (syn isomer).

| | (C) Test Results M.I.C. ($\mu g/ml$) | | | |
|---|---|---|---|---|
| | Compounds | | | |
| Test strains | (1) | (2) | (3) | (4) |
| Escherichia coli NIHJ JC-2 | 1.56 | 3.13 | 1.56 | 1.56 |
| Proteus vulgaris IAM-1025 | 0.39 | 0.78 | 0.10 | 0.78 |
| Escherichia coli 31 | 0.20 | 0.20 | 0.20 | 0.20 |
| Klebsiella pneumoniae 20 | 0.10 | 0.10 | 0.20 | 0.39 |
| Proteus mirabilis 18 | 0.05 | 0.025 | 0.05 | 0.20 |

[2] Urinary excretion

(A) Test Method

Urine of rats was collected with a urine collector at 0 to 6, and 6 to 24 hours after oral administration of 100 mg of the test drugs per Kg. The concentration of antibiotic in urine samples were bioassayed with the standard buffer at pH 7.0, and the urinary excretion in 24 hours were calculated.

(B) Test Compounds (1) 7-[2-(2-aminothiazol-4-yl)-2-carboxymethoxyiminoacetamido]-3-methylthio-3-cephem-4-carboxylic acid (syn isomer).

(2) 7-[2-(2-aminothiazol-4-yl)-2-carboxymethoxyiminoacetamido]-3-ethylthio-3-cephem-4-carboxylic acid (syn isomer).

(3) 7-[2-(4-thiazolyl)-2-carboxymethoxyiminoacetamido]-3-methylthio-3-cephem-4-carboxylic acid (syn isomer).

| (C) Test Results | |
|---|---|
| | Urinary excretion in 24 hours (%) |
| Test Compound (1) | 51.6 |
| Test Compound (2) | 19.4 |
| Test Compound (3) | 48.6 |

[3] Biliary excretion

(A) Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg of the test drugs per kg. The antibiotic levels in the bile samples were assyed with the standard solutions prepared with M/15 phosphate buffer (pH 7.0) and the biliary excretion in 24 hours were calculated.

(B) Test Compounds (1) 7-[2-(2-aminothiazol-4-yl)-2-carboxymethoxyiminoacetamido]-3-methylthio-3-cephem-4-carboxylic acid (syn isomer).
(2) 7-[2-(2-aminothiazol-4-yl)-2-carboxymethoxyiminoacetamido]-3-ethylthio-3-cephem-4-carboxylic acid (syn isomer).
(3) 7-[2-(4-thiazolyl)-2-carboxymethoxyiminoacetamido]-3-methylthio-3-cephem-4-carboxylic acid (syn isomer).

| (C) Test Results | |
|---|---|
| | Biliary excretion in 24 hours (%) |
| Test Compound (1) | 41.1 |
| Test Compound (2) | 32.2 |
| Test Compound (3) | 25.5 |

The following preparations and examples are given for the purpose of illustrating the present invention in more detail.

Preparation 1

(1) To a solution of tert-butyl 2-hydroxyimino-3-oxobutyrate (syn isomer) (187 g) in ethyl acetate (280 ml) and N,N-dimethylformamide (187 ml) was added potassium carbonate (166 g) at ambient temperature. To the suspension was dropwise added methyl monochloroacetate (109 g) and the reaction mixture was stirred at ambient temperature for 7.5 hours.

To the resultant suspensions was added ethyl acetate (280 ml) and the inorganic salts were filtered off. The organic solution was washed with a saturated aqueous solution of sodium chloride four times. The organic layer was dried over magnesium sulfate and concentrated under reduced pressure to give tert-butyl 2-methoxycarbonylmethoxyimino-3-oxobutyrate (syn isomer) 246 g).

IR (film): 1760, 1740, 1690, 1610 cm$^{-1}$.
NMR (DMSO-d$_6$, δ): 1.40 (9H, s), 1.23 (3H, s), 3.62 (3H, s), 4.86 (2H, s).

(2) To a solution of tert-butyl 2-methoxycarbonylmethoxyimino-3-oxobutyrate (syn isomer) (10 g) in glacial acetic acid (5 ml) was added 30% hydrobromic acid in acetic acid (10 ml) at ambient temperature with stirring. The reaction mixture was stirred at 40° C. for 3 hours. The resultant solution was concentrated under reduced pressure and the residual oil was dissolved into ethyl acetate (100 ml). The ethyl acetate layer was washed with a saturated aqueous solution of sodium chloride four times and dried over magnesium sulfate. The solvent was evaporated under reduced pressure to give a crude oil (8.6 g). The oil was dissolved in methylene chloride (100 ml). To the solution was added potassium carbonate (1.87 g) and the suspension was stirred at ambient temperature for 30 minutes. The solution was diluted with n-hexane (100 ml.) The solvent was decanted and the residual glassy mass was dissolved in ethyl acetate and 10% hydrochloric acid. The separated organic layer was washed with a saturated aqueous solution of sodium chloride and dried over magnesium sulfate. The solvent was concentrated under reduced pressure to give 2-methoxycarbonylmethoxyimino-3-oxobutyric acid (syn isomer) (4.0 g) as an oil.

IR (film): 3500, 1720 (broad) cm$^{-1}$.
NMR (DMSO-d$_6$, δ): 2.46 (3H, s), 3.83 (3H, s), 5.06 (2H, s).

To a solution of tert-butyl 2-methoxycarbonylmethoxyimino-3-oxobutyrate (syn isomer) (51.9 g) in glacial acetic acid (52 ml) was slowly added sulfuryl chloride (72.2 ml) at 40° C. with stirring. The reaction mixture was stirred at the same temperature for an hour. The resultant solution was concentrated under reduced pressure and the residual oil was dissolved in ethyl acetate (300 ml). The ethyl acetate layer was washed with 10% hydrochloric acid once and washed with a saturated aqueous solution of sodium chloride four times. The separated organic layer was dried over magnesium sulfate and concentrated under reduced pressure. The residual oil was diluted with n-hexane (100 ml) and evaporated under reduced pressure. The white crystalline precipitates were washed with diisopropyl ether (100 ml). The precipitates were collected by filtration, dried under reduced pressure to give crystalline 4-chloro-2-methoxycarbonylmethoxyimino-3-oxobutyric acid (syn isomer) (13.4 g), mp. 127° to 128.5° C.

IR (Nujol): 1745, 1720, 1701, 1604 cm$^{-1}$.
NMR (DMSO-d$_6$, δ): 3.66 (3H, s), 4.79 (2H, s), 4.92 (2H, s).

Preparation 2

(1) Vilsmeier reagent was prepared from phosphorus oxychloride (10.1 g) and dimethylformamide (4.8 g) in ethyl acetate (16 ml) in a usual manner. 4-Chloro-2-methoxycarbonylmethoxyimino-3-oxobutyric acid (syn isomer) (15.7 g) was added to the stirred suspension of Vilsmeier reagent in ethyl acetate (116 ml) under ice-cooling and the mixture was stirred at this temperature for 30 minutes to give an activated acid solution. To a solution of benzhydryl 7-amino-3-methylthio-3-cephem-4-carboxylate, hydrochloride (26.9 g) and trimethylsilylacetamide (42 g) in ethyl acetate (300 ml) was added the above activated acid solution at −20° C., and the mixture was stirred at −20° to 0° C. for one hour. To the reaction mixture was added water (200 ml) and the ethyl acetate layer was separated. The ethyl acetate layer was washed with saturated sodium bicarbonate solution and brine, and dried over magnesium sulfate. The solution was evaporated and the residue was triturated with ether to give benzhydryl 7-(4-chloro-2-methoxycarbonylmethoxyimino-3-oxobutyramido]-3-methylthio-3-cephem-4-carboxylate (syn isomer) (35.7 g).

IR (Nujol): 3275, 1770, 1735, 1710, 1665 cm$^{-1}$.
NMR (DMSO-d$_6$, δ): 2.28 (3H, s), 3.63 (3H, s), 3.80 (2H, s), 4.73 (2H, s), 4.88 (2H, s), 5.13 (1H, d, J=5 Hz), 5.77 (1H, dd, J=5, 8 Hz), 6.78 (1H, s), 7.07−7.63 (10H, m), 9.43 (1H, d, J=8 Hz).

(2) To a solution of benzhydryl 7-[4-chloro-2-methoxycarbonylmethoxyimino-3-oxobutyramido]-3-methylthio-3-cephem-4-carboxylate (syn isomer) (12.65 g) and anisole (8.5 g) in dichloromethane (30 ml) was added trifluoroacetic acid (36.5 g) under ice-cooling and the mixture was stirred at ambient temperature for 1.5 hours. The reaction mixture was dropwise added to a mixture of isopropyl ether and n-hexane (1:1 400 ml) under stirring. The precipitates were collected by filtration and washed with n-hexane to give 7-[4-chloro-2-methoxycarbonylmethoxyimino-3-oxobutyramido]-3-methylthio-3-cephem-4-carboxylic acid (syn isomer) (7.3 g).

IR (Nujol): 3250, 1770, 1730, 1710, 1660, 1605 cm$^{-1}$.

NMR (DMSO-d$_6$, δ): 2.36 (3H, s), 3.74 (3H, s), 3.78 (2H, s), 4.78 (2H, s), 4.93 (2H, s), 5.13 (1H, d, J=5 Hz), 5.70 (1H, dd J=5, 8 Hz), 9.42 (1H, d, J=8 Hz).

Preparation 3

To a solution of benzhydryl 7-phenylacetamido-3-hydroxy-3-cephem-4-carboxylate-1-oxide (40 g) in pyridine (120 ml) was added mesyl chloride (13 g) under ice-cooling. The reaction mixture was stirred at ambient temperature for an hour. The resulting suspension was poured into water (1 l). The precipitates were collected by filtration, washed with water and methanol, dried under reduced pressure to give benzhydryl 7-phenylacetamido-3-mesyloxy-3-cephem-4-carboxylate-1-oxide (37.0 g).

IR (Nujol): 3290, 1798, 1720, 1655 cm$^{-1}$.

NMR (DMSO-d$_6$, δ): 3.11 (3H, s), 3.67 (2H, s), 4.13 (2H, broad s), 5.04 (1H, d, J=5 Hz), 5.91 (1H, dd, J=5 Hz, 9 Hz), 6.98 (1H, s), 7.2-7.6 (15H, m), 8.53 (1H, d, J=9 Hz).

Preparation 4

To a solution of benzhydryl 7-phenylacetamido-3-mesyloxy-3-cephem-4-carboxylate-1-oxide (400 g) in N,N-dimethylformamide (2.5 l) were added diisopropylethylamine (123 ml) and methanethiol (194 g) at ambient temperature. The reaction mixture was stirred at the same temperature for 12 hours. The resulting solution was poured into water (25 l). The precipitates were collected by filtration and washed with water and dried under reduced pressure. The precipitates were washed with methanol (5 l) and dried under reduced pressure to give benzhydryl 7-phenylacetamido-3-methylthio-3-cephem-4-carboxylate-1-oxide (275 g).

IR (Nujol): 3300, 1788, 1710, 1658 cm$^{-1}$.

Preparation 5

To a solution of benzhydryl 7-phenylacetamido-3-p-toluenesulfonyloxy-3-cephem-4-carboxylate-1-oxide (15 g) in N,N-dimethylformamide (75 ml) were added diisopropylethylamine (4.67 ml) and methylmercaptan (7.0 g) at ambient temperature. The mixed solution was stirred at the same temperature for 18 hours. The resultant solution was dropwise added to water (1.5 l) and the precipitates were collected by filtration, washed with water and diisopropyl ether. The precipitates were stirred in methanol (30 ml) for an hour at ambient temperature. The insoluble substances were collected by filtration to give benzhydryl 7-phenylacetamido-3-methylthio-3-cephem-4-carboxylate-1-oxide (6.7 g).

IR (Nujol): 3300, 1788, 1710, 1658 cm$^{-1}$.

NMR (DMSO-d$_6$, δ): 2.28 (3H, s), 3.65 (2H, s), 3.80, 4.40 (2H, ABq, J=18 Hz), 4.87 (1H, d, J=5 Hz), 5.82 (1H, dd, J=5 Hz, 9 Hz), 6.85 (1H, s), 7.3 (10H, m), 8.30 (1H, d, J=9 Hz).

Preparation 6

The following compounds were obtained according to the similar manners to those of Preparations 4 and 5.

(1) Benzhydryl 7-phenylacetamido-3-ethylthio-3-cephem-4-carboxylate-1-oxide.

IR (Nujol): 3300, 1785, 1722, 1657 cm$^{-1}$.

NMR (DMSO-d$_6$, δ): 1.10 (3H, t, J=7 Hz), 2.78 (2H, q, J=7 Hz), 3.63 (2H, broad s), 3.80, 4.33 (2H, Abq, J=18 Hz), 4.90 (1H, d, J=5 Hz), 5.83 (1H, dd, J=5 Hz, 8 Hz), 6.85 (1H, s), 7.3 (10H, m), 8.32 (1H, d, J=8 Hz).

(2) Benzhydryl 7-phenylacetamido-3-propylthio-3-cephem-4-carboxylate-1-oxide.

IR (Nujol): 3280, 1779, 1715, 1648 cm$^{-1}$.

NMR (DMSO-d$_6$, δ): 0.87 (3H, t, J=7 Hz), 1.41 (2H, sextet, J=7 Hz), 2.74 (2H, t, J=7 Hz), 3.63 (2H, broad s), 3.78, 4.32 (2H, ABq, J=18 Hz), 4.90 (1H, d, J=4.5 Hz), 5.82 (1H, dd, J=4.5 Hz, 8 Hz), 6.87 (1H, s), 7.40 (15 H, m), 8.37 (1H, d, J=8 Hz).

Preparation 7

To a solution of benzhydryl 7-phenylacetamido-3-methylthio-3-cephem-4-carboxylate-1-oxide (6.5 g) and amylene (2.53 ml) in methylenechloride (100 ml) was dropwise added acetyl bromide (2.4 ml) under ice-cooling with stirring. The mixture was stirred at ambient temperature for 30 minutes. The resultant solution was added to water. The separated organic layer was washed with a saturated aqueous solution of sodium chloride twice and dried over magnesium sulfate. The solvent was evaporated under reduced pressure to give benzhydryl 7-phenylacetamido-3-methylthio-3-cephem-4-carboxylate (5.4 g).

IR (Nujol): 3300, 1782, 1703, 1662 cm$^{-1}$.

NMR (DMSO-d$_6$, δ): 2.29 (3H, s), 3.53 (2H, broad s), 3.79 (2H, broad s), 5.07 (1H, d, J=5 Hz), 5.64 (1H, dd, J=5 Hz, 8 Hz), 6.83 (1H, s), 7.3 (10H, m).

Preparation 8

The following compounds were obtained according to a similar manner to that of Preparation 7.

(1) Benzhydryl 7-phenylacetamido-3-ethylthio-3-cephem-4-carboxylate.

IR (Nujol): 3300, 1745 (broad), 1682 cm$^{-1}$.

NMR (DMSO-d$_6$, δ): 1.10 (3H, t, J=7 Hz), 2.82 (2H, q, J=7 Hz), 3.57 (2H, broad s), 3.77 (2H, broad s), 5.13 (1H, d, J=5 Hz), 5.62 (1H, dd, J=8 Hz), 6.83 (1H, s), 7.3 (10H, m), 9.07 (1H, d, J=8 Hz).

(2) Benzhydryl 7-phenylacetamido-3-propylthio-3-cephem-4-carboxylate.

IR (Nujol): 3300, 1742 (broad), 1710, 1678 cm$^{-1}$.

NMR (DMSO-d$_6$, δ): 0.90 (3H, t, J=7 Hz), 1.43 (2H, sextet, J=7 Hz), 2.80 (2H, t, J=7 Hz), 3.57 (2H, broad s), 3.78 (2H, broad s), 5.13 (1H, d, J=5 Hz), 5.63 (1H, dd, J=5 Hz, 8 Hz), 6.87 (1H, s), 7.3 (10H, m), 9.10 (1H, d, J=8 Hz).

Preparation 9

To a suspension of pyridine phosphorus pentachloride complex prepared from pyridine (20 g) and phosphorus pentachloride (52.5 g) in methylene chloride (860 ml) was added benzhydryl 7-phenylacetamido-3-methylthio-3-cephem-4-carboxylate (67.0 g) under ice-cooling with stirring. The mixture was stirred at the same temperature for 30 minutes, and poured into methanol (650 ml) at −30° C. The mixed solution was stirred at −5° to −15° C. for 10 minutes and then evaporated under reduced pressure. To the residue were added ethyl acetate (500 ml) and cooled water (500 ml). The mixture was stirred for several minutes. The crystalline materials were collected by filtration and washed with diethyl ether to give benzhydryl 7-amino-3-methylthio-3-cephem-4-carboxylate hydrochloride (36.1 g), mp. 170° to 171° C. (dec.).

IR (Nujol): 3380, 1781, 1758, 1693 cm$^{-1}$.

NMR (DMSO-d$_6$, δ): 2.43 (3H, s), 3.75, 4.13 (2H, ABq, J=16 Hz), 5.10 (1H, d, J=5 Hz), 5.30 (1H, d, J=5 Hz), 6.88 (1H, s), 7.40 (10H, m).

Preparation 10

The following compounds were obtained according to a similar manner to that of Preparation 9.

(1) Benzhydryl 7-amino-3-ethylthio-3-cephem-4-carboxylate hydrochloride, mp. 172° to 173° C. (dec.).

IR (Nujol): 1778, 1705 cm$^{-1}$.

DMR (DMSO-d$_6$, δ): 1.16 (3H, t, J=7 Hz), 2.93 (2H, q, J=7 Hz), 3.68, 4.10 (2H, ABq, J=15 Hz), 5.05 (1H, d, J=5 Hz), 5.77 (1H, d, J=5 Hz), 6.83 (1H, s), 7.3 (10H, m).

(2) Benzhydryl 7-amino-3propylthio-3-cephem-4-carboxylate hydrochloride, mp. 160° to 162° C. (dec.).

IR (Nujol): 1772, 1732, 1700 cm$^{-1}$.

NMR (DMSO-d$_6$, δ): 0.93 (3H, t, J=7 Hz), 1.50 (2H, sextet, J=7 Hz), 2.95 (2H, t, J=7 Hz), 3.88 (2H, ABq, J=16 Hz), 5.08 (1H, d, J=5 Hz), 5.30 (1H, d, J=5 Hz), 6.90 (1H, s), 7.30 (10H, m).

Preparation 11

To a suspension of phosphorus pentachloridepyridine complex prepared from phosphorus pentachloride (2.05 g) and pyridine (0.8 ml) in methylene chloride (40 ml) was added benzhydryl 7-phenylacetamido-3-tosyloxy-3-cephem-4-carboxylate (4.3 g) under ice-cooling with stirring. The mixture was stirred at the same temperature for 30 minutes and cooled in a dry ice-acetone bath. To the solution was added methanol (6 ml) at −30° C. and the mixed solution was stirred at −10° to −5° C. for an hour. The resulting solution was adjusted to pH 6.5 with a saturated aqueous solution of sodium bicarbonate and extracted with ethyl acetate (100 ml). The separated organic layer was washed with a saturated aqueous solution of sodium chloride, dried over magnesium sulfate. The solvent was evaporated under reduced pressure to give benzhydryl 7-amino-3-tosyloxy-3-cephem-4-carboxylate (3.1 g)

IR (Nujol): 3300, 1780, 1730 cm$^{-1}$.

NMR (DMSO-d$_6$, δ): 2.33 (3H, s), 3.73 (2H, m), 5.20 (2H, m), 6.67 (1H, s), 7.13–7.75 (14H, m).

Preparation 12

Vilsmeier reagent prepared from phosphorus oxychloride (0.67 ml) and N,N-dimethylformamide (0.57 ml) was suspended in dry tetrahydrofuran (24 ml). To the suspension was added 2-(2-formamidothiazol-4-yl)-2-tert-butoxycarbonylmethoxyiminoacetic acid (syn isomer) (2.4 g) at 0° to 5° C. The solution was stirred at the same temperature for an hour to prepare the activated acid solution. To a solution of benzhydryl 7-amino-3-tosyloxy-3-cephem-4-carboxylate (3.0 g) and monotrimethylsilylacetamide (5.8 g) in methylene chloride (30 ml) was added the activated acid solution obtained above at −20° C. all at once. The reaction mixture was stirred at −10° C. for an hour. The resulting solution was poured into water (100 ml) and extracted with ethyl acetate (100 ml). The separated organic layer was washed with a saturated aqueous solution of sodium bicarbonate, and with a saturated aqueous solution of sodium chloride. The organic layer was dried over magnesium sulfate and concentrated under reduced pressure to give benzhydryl 7-[2-(2-formamidothiazol-4-yl)-2-tert-butoxycarbonylmethoxyiminoacetamido]-3-tosyloxy-3-cephem-4-carboxylate (syn isomer) (3.4 g).

IR (Nujol): 3250, 3150, 1786, 1733, 1690 cm$^{-1}$.

NMR (DMSO-d$_6$, δ): 1.43 (9H, s), 2.33 (3H, s), 3.73 (2H, m), 4.57 (2H, broad s), 5.32 (1H, d, J=5 Hz), 5.87 (1H, dd, J=5 Hz, 8 Hz), 6.68 (1H, s), 7.1–7.9 (15H, m), 8.46 (1H, s), 9.60 (1H, d, J=8 Hz), 12.6 (1H, broad s).

Preparation 13

To a solution of benzhydryl 7-[2-(2-formamidothiazol-4-yl)-2-tert-butoxycarbonylmethoxyiminoacetamido]-3-tosyloxy-3-cephem-4-carboxylate (syn isomer) (3.2 g) in methylene chloride (20 ml) was added m-chloroperbenzoic acid (1.62 g) at ambient temperature. The mixture was stirred for an hour. The resulting solution was concentrated under reduced pressure and the residue was subjected to column chromatography on silica gel (eluent: benzene-ethyl acetate) to give benzhydryl 7-[2-(2-formamidothiazol-4-yl)-2-tert-butoxycarbonylmethoxyiminoacetamido]-3-tosyloxy-3-cephem-4-carboxylate-1-oxide (syn isomer), 0.6 g).

IR (Nujol): 3170, 1803, 1740, 1692, 1668 cm$^{-1}$.

NMR (DMSO-d$_6$, δ): 1.42 (9H, s), 2.33 (3H, s), 4.03 (2H, broad s), 4.60 (2H, broad s), 5.15 (1H, d, J=4 Hz), 5.96 (1H, m), 6.70 (1H, s), 7.16–7.68 (15H, m), 8.46 (1H, s), 8.97 (1H, d, J=8 Hz).

Preparation 14

To a solution of benzhydryl 7-[2-(2-formamidothiazol-4-yl)-2-tert-butoxycarbonylmethoxyiminoacetamido]-3-tosyloxy-3-cephem-4-carboxylate-1-oxide (syn isomer) (0.54 g) and diisopropylethylamine (0.12 ml) in N,N-dimethylformamide (2.7 ml) was added methanethiol (0.35 ml). The mixture was allowed to stand at ambient temperature for 15 hours and poured into water. The precipitates were collected by filtration and subjected to column chromatography on silica gel (eluent benzene-ethyl acetate) to give benzhydryl 7-[2-(2-formamidothiazol-4-yl)-2-tert-butoxycarbonylmethoxyiminoacetamido]-3-methylthio-3-cephem-4-carboxylate-1-oxide (syn isomer) (0.2 g).

IR (Nujol): 3270, 3150, 1783, 1751, 1702, 1662 cm$^{-1}$.

NMR (DMSO-d$_6$, δ): 1.43 (9H, s), 2.33 (3H, s), 3.83, 4.43 (2H, ABq, J=18 Hz), 4.62 (2H, broad s), 5.02 (1H, d, J=5 Hz), 6.00 (1H, dd, J=5 Hz, 8 Hz), 6.86 (1H, s), 7.3 (10H, m), 7.50 (1H, s), 8.48 (1H, s), 8.73 (1H, d, J=8 Hz), 12.6 (1H, broad s).

Preparation 15

To a solution of 2-naphthylglyoxylic acid (6 g) in water (60 ml) and pyridine (6 ml) was added tert-butoxycarbonylmethoxyamine (9 g) in tetrahydrofuran (40 l) at room temperature and the mixture was stirred at the same temperature for 3 hours. The resultant mixture was adjusted to pH 7.5 with 10% aqueous sodium hydroxide and washed with ethyl acetate. The aqueous layer was acidified to pH 2.0 with 10% hydrochloric acid and the acidified solution was extracted with ethyl acetate. The organic layer was washed with brine and dried over magnesium sulfate. The solution was evaporated in vacuo to give 2-(tert-butoxycarbonylmethoxyimino)-2-(2-naphthyl)acetic acid (syn isomer) (8 g).

IR (Nujol): 1740, 1700 cm$^{-1}$.

NMR (DMSO-d$_6$, δ): 1.50 (9H, s), 4.78 (2H, s), 7.5–8.2 (7H, m).

Preparation 16

To a solution of (1,2,5-thiadiazol-3-yl)glyoxylic acid (6 g) in tetrahydrofuran (30 ml) and water (30 ml) was added tert-butoxycarbonylmethoxyamine (8.37 g) at room temperature. The mixture was adjusted to pH 4.5–5.0 with 4 N aqueous sodium hydroxide and stirred at ambient temperature for 4 hours. The mixture was adjusted to pH 7.5 with 4 N aqueous sodium hydroxide and washed with ethyl acetate (100 ml×2). The aqueous layer was acidified to pH 2.0 with 10% hydrochloric acid and extracted with ethyl acetate (100 ml×2). The organic layer was washed with brine and dried over magnesium sulfate. The solution was evaporated in vacuo to give 2-(tert-butoxycarbonylmethoxyimino)-2-(1,2,5-thiadiazol-3-yl)acetic acid (syn and anti mixture) (10.02 g).

IR (Nujol): 3450, 1720, 1700 $cm^{-1}$.
NMR (DMSO-$d_6$, δ): 1.48 (9H, s), 1.48 (9H, s), 4.73 (2H, s), 4.82 (2H, s), 8.88 (1H, s), 9.17 (1H, s).

Preparation 17

The following compound was prepared according to the similar manners to those of Preparations 15 and 16.

(1) 2-t-Butoxycarbonylmethoxyimino-2-(4-thiazolyl)acetic acid (syn isomer), mp. 136° to 139° C.

IR (Nujol): 1730 $cm^{-1}$.

Preparation 18

The following compound was prepared according to the similar manner to that of Preparation 2 (1). (1) 7-[4-Chloro-2-methoxycarbonylmethoxyimino-3-oxobutyramido]-3-methylthio-3-cephem-4-carboxylic acid (syn isomer).

IR (Nujol): 3250, 1770, 1730, 1710, 1660, 1605 $cm^{-1}$.

Preparation 19

A solution of isoamylnitrite (31.4 g) in tetrahydrofuran (131 ml) was dropwise added to a mixture of 2-(5-amino-1,2,4,-thiadiazol-3-yl)-2-(t-butoxycarbonylmethoxyimino)-acetic acid(syn ismer)(45 g) in tetrahydrofuran (450 ml) at 50° C. to 55° C. under stirring and the mixture was stirred at 62° C. to 64° C. for 6 hours. Tetrahydrofuran was evaporated in vacuo. The residue was dissolved in a mixture of ethyl acetate and water and adjusted to Ph 7.5 with saturated aqueous potassium carbonate. The separated aqueous layer was acidified to Ph 2.0 with 10% hydrochloric acid and extracted with ethyl acetate. The extract layer was washed with saturated aqueous sodium chloride, dried over magnesium sulfate and evaporated to give 2-(t-butoxy-carbonylmethoxyimino)-2-(1,2,4-thiadiazol-3-yl) acetic acid (syn isomer) (32.03 g).

IR (Nujol): 1740, 1600 $cm^{-1}$.
NMR (DMSO-$d_6$, δ): 1.46 (9H.S), 4.76 (2H, S), 10.32 (1H, S).

EXAMPLE 1

Vilsmeier reagent was prepared from phosphorus oxychloride (1.3 g) and dimethylformamide (0.6 g) in ethyl acetate (2.4 ml) in a usual manner. 2-(t-Butoxycarbonylmethoxyimino)-2-(4-thiazolyl)acetic acid (syn isomer) (2.0 g) was added to the stirred suspension of Vilsmeier reagent in ethyl acetate (20 ml) under ice cooling and stirred for 20 minutes at same temperature to produced an activated solution. N-(trimethylsilyl)acetamide (5.8 g) was added to the stirred suspension of benzhydryl 7-amino-3-methylthio-3-cephem-4-carboxylate hydrochloride (2.9 g) in ethyl acetate (30 ml) and stirred for 10 minutes at 40° C. To the solution was added the above activated solution at −10° C. and stirred for 30 minutes at same temperature. Water was added to the reaction mixture and separated organic layer was washed with saturated aqueous sodium bicarbonate and saturated aqueous sodium chloride and then dried over magnesium sulfate. The solvent was evaporated to give benzyhydryl 7-[2-(t-butoxycarbonylmethoxyimino)-2-(4-thiazolyl)acetamido]-3-methylthio-3-cephem-4-carboxylate (syn isomer) (3.62 g).

IR (Nujol): 3270, 1780, 1720, 1655 $cm^{-1}$.
NMR (DMSO-$d_6$, δ): 1.43 (9H, s), 2.33 (3H, s), 3.80 (2H, s), 4.63 (2H, s), 5.21 (1H, d, J=5.0 Hz), 5.82 (1H, dd, J=5.0 Hz, 8.0 Hz), 6.83 (1H, s), 7.07–7.70 (10H, m), 7.94 (1H, d, J=2.0 Hz), 9.12 (1H, d, J=2.0 Hz), 9.57 (1H, d, J=8.0 Hz).

EXAMPLE 2

Vilsmeier reagent prepared from N,N-dimethylformamide (0.5 ml) and phosphorus oxychloride (0.58 ml) was suspended in dry tetrahydrofuran (20 ml). To a suspension was added 2-(2-formamidothiazol-4-yl)-2-tert-butoxycarbonylmethoxyiminoacetic acid (syn isomer, 2 g) under ice-cooling with stirring, and then the solution was stirred at the same temperature for an hour to prepare the activated acid solution. To the solution of benzhydryl 7-amino-3-methylthio-3-cephem-4-carboxylate (2.0 g) and trimethylsilylacetamide (5.0 g) in methylene chloride was added the activated acid solution obtained above all at once at −20° C., and then the mixed solution was stirred at −20° to −10° C. for an hour. Water and ethyl acetate were added to the resultant solution. The solution was adjusted to pH 7.5 with an aqueous saturated solution of sodium bicarbonate. The organic layer was washed with an aqueous saturated solution of sodium chloride, and dried over magnesium sulfate. The solvent was evaporated in vacuo to give benzhydryl 7-[2-(2-formamidothiazol-4-yl)-2-tert-butoxycarbonylmethoxyiminoacetamido]-3-methylthio-3-cephem-4-carboxylate (syn isomer, 2.4 g). mp. 151°–157° C.

IR (Nujol): 3250, 1780, 1690 $cm^{-1}$.
NMR (DMSO-$d_6$, δ): 1.44 (9H, s), 2.18 (3H, s), 3.80 (2H, m), 4.61 (2H, br. s), 5.21 (1H, d, J=5 Hz), 5.80 (1H, dd, J=5 Hz, 8 Hz), 6.82 (1H, s), 7.30 (10H, m), 7.47 (1H, s), 8.48 (1H, s), 9.58 (1H, d, J=8 Hz), 12.6 (1H, br. s).

EXAMPLE 3

To a suspension of phosphorus pentachloride (1.18 g) in methylene chloride (17 ml) was added 2-(5-amino-1,2,4-thiadiazol-3-yl)-2-tert-butoxycarbonylmethoxyiminoacetic acid (syn isomer, 1.7 g) with stirring at −18° C. The mixture was stirred at −15° to −12° C. for an hour. Dry diisopropyl ether was added to the solution. The precipitates were collected by filtration and washed with dry diisopropyl ether. To a solution of benzhydryl 7-amino-3-methylthio-3-cephem-4-carboxylate (1.8 g) and monotrimethylsilylacetamide (4.6 g) in methylene chloride (36 ml) was added the precipitates obtained above at −10° C. with stirring. The reaction mixture was stirred for an hour at −10° to −5° C.

The reaction mixture was poured into water (100 ml) and extracted with ethyl acetate (100 ml).

The organic layer was washed with 5% aqueous solution of sodium bicarbonate and an aqueous saturated solution of sodium chloride in turn and dried over magnesium sulfate.

The solvent was evaporated under reduced pressure to give benzhydryl 7-[2-(5-amino-1,2,4-thiadiazol-3-yl)-2-tert-butoxycarbonylmethoxyiminoacetamido]-3-methylthio-3-cephem-4-carboxylate (syn isomer, 1.8 g), mp. 123°–129° C. (dec.).

IR (Nujol): 3300, 1776, 1689, 1615 $cm^{-1}$.
NMR (DMSO-$d_6$, δ): 1.46 (9H, s), 2.35 (3H, s), 3.83 (2H, m), 4.67 (2H, broad s), 5.20 (1H, d, J=5 Hz), 5.87

(1H, dd, J=5 Hz, 8 Hz), 6.87 (1H, s), 7.3 (10 H, m), 9.56 (1H, d, J=8 Hz).

EXAMPLE 4

Vilsmeier reagent prepared from N,N-dimethylformamide (0.42 ml) and phosphorus oxychloride (0.527 ml) was suspended in dry tetrahydrofuran (30.5 ml). To a suspension was added 2-(2-formamido-5-chlorothiazol-4-yl)-2-tert-butoxycarbonylmethoxyiminoacetic acid (syn isomer, 2.8 g) under ice-cooling with stirring and then the solution was stirred at the same temperature for an hour to prepare the activated acid solution. To the solution of benzhydryl 7-amino-3-ethylthio-3-cephem-4-carboxylate hydrochloride (2.0 g) and monotrimethylsilylacetamide (5.7 g) in methylene chloride (40 ml) was added the activated acid solution obtained above all at once at $-0°$ C. and the mixed solution was stirred at $-20°$ to $-10°$ C. for an hour. After water and ethyl acetate (150 ml) were added to the resultant solution, the mixture was adjusted to pH 7.5 with a saturated aqueous solution of sodium bicarbonate. The organic layer was washed with a saturated aqueous solution of sodium chloride, and dried over magnesium sulfate. The solvent was evaporated under reduced pressure to give benzhydryl 7-[2-(2-formamido-5-chlorothiazol-4-yl)-2-tert-butoxycarbonylmethoxyiminoacetamido]-3-ethylthio-3-cephem-4-carboxylate (syn isomer, 12.8 g), mp. 143° to 148° C.

IR (Nujol): 3250, 1780, 1750, 1728, 1683 cm$^{-1}$.

NMR (DMSO-d$_6$, δ): 1.12 (3H, t, J=7 Hz), 2.87 (2H, q, J=7 Hz), 3.78 (2H, m), 4.65 (2H, broad s), 5.27 (1H, d, J=5 Hz), 5.90 (1H, dd, J=5 Hz, 8 Hz), 6.75 (1H, s), 7.40 (10H, m), 8.53 (1H, s), 9.58 (1H, d, J=8 Hz), 12.7 (1H, broad s).

EXAMPLE 5

Vilsmeier reagent prepared from phosphorus oxychloride (0.52 ml) and N,N-dimethylformamide (0.44 ml) was suspended in dry tetrahydrofuran (16.5 ml). To the stirred suspension was added 2-(6-formamidopyridin-2-yl)-2-tert-butoxycarbonylmethoxyiminoacetic acid (syn isomer, 1.67 g) under ice-cooling and then the solution was stirred for an hour at the same temperature to prepare the activated acid solution. To the solution of benzhydryl 7-amino-3-ethylthio-3-cephem-4-carboxylate hydrochloride (2.0 g) and monotrimethylsilylacetamide (5.67 g) in methylene chloride (40 ml) was added the activated acid solution all at once at $-20°$ C., and then the mixed solution was stirred for an hour at $-20°$ to $-10°$ C. To the resultant solution were added water (50 ml) and ethyl acetate (100 ml). The organic layer was separated and washed with 5% aqueous solution of sodium bicarbonate. The solution was washed with a saturated aqueous solution of sodium chloride and dried over magnesium sulfate. The solvent was evaporated under reduced pressure to give benzhydryl 7-[2-(6-formamidopyridin-2-yl)-2-tert-butoxycarbonylmethoxyiminoacetamido]-3-ethylthio-3-cephem-4-carboxylate (syn isomer, 2.5 g), mp. 113° to 123° C.

IR (Nujol): 3250, 1774 (broad), 1688 (broad) cm$^{-1}$.

NMR (DMSO-d$_6$, δ): 1.13 (3H, t, J=7 Hz), 2.83 (2H, q, J=7 Hz), 3.73 (2H, broad s), 4.67 (2H, broad s), 5.27 (1H, d, J=5 Hz), 5.85 (1H, dd, J=5 Hz, 8 Hz), 6.82 (1H, s), 7.3-8.0 (3H, m), 7.4 (10H, m), 9.47 (1H, d, J=8 Hz), 10.53 (1H, broad s).

EXAMPLE 6

The following compounds were prepared according to a similar manner to that of Examples 1 to 5.

(1) Benzhydryl 7-[2-(2-formamidothiazol-4-yl)-2-(tert-butoxycarbonylmethoxyimino)acetamido]-3-methylthio-3-cephem-4-carboxylate (syn isomer), mp. 151° to 157° C.

IR (Nujol): 3250, 1780, 1690 cm$^{-1}$.

(2) Benzhydryl 7-[2-(2-aminothiazol-4-yl)-2-(methoxycarbonylmethoxyimino)acetamido]-3-methylthio-3-cephem-4-carboxylate (syn isomer).

IR (Nujol): 1770, 1670, 1610 cm$^{-1}$.

(3) 7-[2-(2-Aminothiazol-4-yl)-2-(methoxycarbonylmethoxyimino)acetamido]-3-methylthio-3-cephem-4-carboxylic acid (syn isomer).

IR (Nujol): 3250, 1765, 1720, 1650 cm$^{-1}$.

(4) 7-[2-(2-Aminothiazol-4-yl)-2-(carboxymethoxyimino)acetamido]-3-methylthio-3-cephem-4-carboxylic acid (syn isomer), mp. 183° to 186° C. (dec.).

IR (Nujol): 3300, 1760, 1665 cm$^{-1}$.

(5) 7-[2-Benzhydryloxycarbonylmethoxyimino-2-(2-formamidothiazol-4-yl)acetamido]-3-methylthio-3-cephem-4-carboxylic acid (syn isomer).

IR (Nujol): 3270, 1770, 1740, 1650 (br) cm$^{-1}$.

NMR (DMSO-d$_6$, δ): 2.32 (3H, s), 3.73 (2H, s), 4.94 (2H, s), 5.18 (1H, d, J=5.0 Hz), 5.76 (1H, dd, J=5.0 Hz, 8.0 Hz), 6.89 (1H, s), 7.17-7.63 (11H, m), 8.51 (1H, s), 9.69 (1H, d, J=8.0 Hz), 12.58 (1H, broad s).

(6) Sodium 7-[2-(2-Aminothiazol-4-yl)-2-benzhydryloxycarbonylmethoxyiminoacetamido]-3-methylthio-3-cephem-4-carboxylate (syn isomer).

IR (Nujol): 1730 (broad), 1670 cm$^{-1}$.

(7) Pivaloyloxymethyl 7-[2-(2-aminothiazol-4-yl)-2-benzhydryloxycarbonylmethoxyiminoacetamido]-3-methylthio-3-cephem-4-carboxylate (syn isomer).

IR (Nujol): 3280, 3180, 1740 (broad), 1670, 1620 cm$^{-1}$.

(8) Pivaloyloxymethyl 7-[2-(2-aminothiazol-4-yl)-2-carboxymethoxyiminoacetamido]-3-methylthio-3-cephem-4-carboxylate (syn isomer).

IR (Nujol): 3300, 3200, 1770, 1750, 1670 cm$^{-1}$.

(9) Benzhydryl 7-[2-(2-formamidothiazol-4-yl)-2-(tert-butoxycarbonylmethoxyimino)acetamido]-3-methylthio-3-cephem-4-carboxylate (anti isomer).

IR (Nujol): 3250, 1760 (broad), 1685 cm$^{-1}$.

NMR (DMSO-d$_6$, δ): 1.43 (9H, s), 2.30 (3H, s), 3.80 (2H, broad s), 4.73 (2H, s), 5.18 (1H, d, J=5 Hz), 5.82 (1H, dd, J=5, 8 Hz), 6.87 (1H, s), 7.07-7.70 (10 H, m), 8.12 (1H, s), 8.47 (1H, s), 9.43 (1H, d, J=8 Hz).

(10) Benzhydryl 7-[2-(2-aminothiazol-4-yl)-2-(tert-butoxycarbonylmethoxyimino)acetamido]-3-methylthio-3-cephem-4-carboxylate (anti isomer).

IR (Nujol): 3300, 1760, 1685, 1610 cm$^{-1}$.

(11) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$.

(12) 7-[2-(2-Methylaminothiazol-4-yl)-2-(methoxycarbonylmethoxyimino)acetamido]-3-methylthio-3-cephem-4-carboxylic acid (syn isomer).

IR (Nujol): 3250, 1785, 1755, 1645 cm$^{-1}$.

(13) 7-[2-(2-Methylaminothiazol-4-yl)-2-carboxymethoxyiminoacetamido]-3-methylthio-3-cephem-4-carboxylic acid (syn isomer).

NMR (DMSO-d$_6$, δ): 2.38 (3H, s), 2.83 (3H, s), 3.77 (2H, s), 4.65 (2H, s), 5.17 (1H, d, J=5 Hz), 5.70 (1H, dd, J=5, 8 Hz), 6.90 (1H, s), 9.45 (1H, d, J=8 Hz).

(14) 7-[2-(Carboxymethoxyimino)-2-(4-thiazolyl)acetamido]-3-methylthio-3-cephem-4-carboxylic acid (syn isomer).

IR (Nujol): 1760, 1670 cm⁻¹.

(15) Benzhydryl 7-[2-(t-butoxycarbonylmethoxyimino)-2-(4-thiazolyl)acetamido]-3-ethylthio-3-cephem-4-carboxylate (syn isomer).

IR (Nujol): 3270, 1765, 1750, 1695, 1680, 1650 cm⁻¹.

NMR (DMSO-$d_6$, δ): 1.14 (3H, t, J=7.0 Hz), 1.44 (9H, s), 2.87 (2H, q, J=7.0 Hz), 3.78 (2H, s), 4.65 (2H, s), 5.29 (1H, d, J=4.0 Hz), 5.84 (1H, dd, J=4.0 Hz, 8.0 Hz), 6.86 (1H, s), 7.14–7.68 (10H, m), 7.96 (1H, d, J=2.0 Hz), 9.15 (1H, d, J=2.0 Hz), 9.61 (1H, d, J=8.0 Hz).

(16) 7-[2-(Carboxymethoxyimino)-2-(4-thiazolyl)acetamido]-3-ethylthio-3-cephem-4-carboxylic acid (syn isomer).

IR (Nujol): 1760, 1670 cm⁻¹.

(17) Benzhydryl 7-[2-(tert-butoxycarbonylmethoxyimino)-2-(1,2,5-thiadiazol-3-yl)acetamido]-3-methylthio-3-cephem-4-carboxylate (syn isomer).

IR (Nujol): 3250, 1765, 1730, 1680 cm⁻¹.

NMR (DMSO-$d_6$, δ): 1.46 (9H, s), 2.32 (3H, s), 3.81 (2H, m), 4.74 (2H, s), 5.23 (1H, d, J=5 Hz), 5.88 (1H, dd, J=8 Hz, 5 Hz), 6.84 (1H, s), 7.0–7.7 (10H, m), 9.02 (1H, s), 9.71 (1H, d, J=8 Hz).

(18) 7-[2-(Carboxymethoxyimino)-2-(1,2,5-thiadiazol-3-yl)acetamido]-3-methylthio-3-cephem-4-carboxylic acid (syn isomer).

IR (Nujol): 3250, 1775, 1680 cm⁻¹.

(19) Benzhydryl 7-[2-(tert-butoxycarbonylmethoxyimino)-2-(2-naphthyl)acetamido]-3-methylthio-3-cephem-4-carboxylate (syn isomer).

IR (Nujol): 3300, 1770, 1720, 1680, 1540 cm⁻¹.

NMR (DMSO-$d_6$, δ): 2.35 (3H, s), 3.80 (2H, s), 4.75 (2H, s), 5.30 (1H, d, J=5 Hz), 5.90 (1H, dd, J=5, 8 Hz), 6.90 (1H, s), 7.0–8.1 (7H, m), 9.83 (1H, d, J=8 Hz).

(20) 7-[2-Carboxymethoxyimino-2-(2-naphthyl)acetamido]-3-methylthio-3-cephem-4-carboxylic acid (syn isomer).

IR (Nujol): 3300, 1760, 1680, 1540 cm⁻¹.

(21) benzhydryl 7-[2-(2-aminothiazol-4-yl)-2-tert-butoxycarbonylmethoxyiminoacetamido]-3-methylthio-3-cephem-4-carboxylate (syn isomer). mp. 148°–155° C.

IR (Nujol): 3300, 1778, 1685 cm⁻¹.

(22) benzhydryl 7-[2-(2-formamidothiazol-4-yl)-2-tert-butoxycarbonylmethoxyiminoacetamido]-3-ethylthio-3-cephem-4-carboxylate (syn isomer). mp 173°–176° C.

IR (Nujol): 3250, 1780, 1745, 1726, 1690 cm⁻¹.

NMR (DMSO-$d_6$, δ): 1.13 (3H, t, J=7 Hz), 2.90 (2H, q, J=7 Hz), 3.80 (2H, m), 4.67 (2H, broad s), 5.32 (1H, d, J=5 Hz), 5.87 (1H, dd, J=5 Hz, 8 Hz), b 6.92 (1H, s), 7.40 (10H, m), 7.53 (1H, s), 8.57 (1H, s), 9.68 (1H, d, J=8 Hz), 12.73 (1H, broad s).

(23) benzhydryl 7-[2-(2-aminothiazol-4-yl)-2-tert-butoxycarbonylmethoxyiminoacetamido]-3-ethylthio-3-cephem-4-carboxylate (syn isomer). mp 165°–169° C.

IR (Nujol): 3250, 1780, 1728, 1685 cm⁻¹.

(24) 7-[2-(2-aminothiazol-4-yl)-2-carboxymethoxyiminoacetamido]-3-methylthio-3-cephem-4-carboxylic acid (syn isomer). mp. 183°–186° C. (dec.).

IR (Nujol): 3300, 1760, 1665 cm⁻¹.

(25) 7-[2-(2-aminothiazol-4-yl)-2-carboxymethoxyiminoacetamido]-3-ethylthio-3-cephem-4-carboxylic acid (syn isomer), mp. 215°–218° C. (dec.).

IR (Nujol): 3280, 1763, 1670 cm⁻¹.

(26) Benzhydryl 7-[2-(5-amino-1,2,4-thiadiazol-3-yl)-2-tert-butoxycarbonylmethoxyiminoacetamido]-3-ethylthio-3-cephem-4-carboxylate (syn isomer), mp. 103° to 108° C. (dec.).

IR (Nujol): 3300, 1775, 1727, 1690, 1620 cm⁻¹.

NMR (DMSO-$d_6$, δ): 1.10 (3H, t, J=7 Hz), 2.82 (2H, q, J=7 Hz), 3.75 (2H, broad s), 4.62 (2H, broad s), 5.22 (1H, d, J=5 Hz), 5.82 (1H, dd, J=5 Hz, 8 Hz), 6.83 (1H, s), 7.3 (10H, m), 9.48 (1H, d, J=8 Hz).

(27) Benzhydryl 7-[2-(5-amino-1,2,4-thiadiazol-3-yl)-2-(1-tert-butoxycarbonylethoxyimino)acetamido]-3-ethylthio-3-cephem-4-carboxylate (syn isomer).

IR (Nujol): 1770, 1720, 1685, 1610 cm⁻¹

NMR (DMSO-$d_6$, δ): 1.08 (3H, t, J=7.0 Hz), 1.28–1.65 (12H, m), 2.82 (2H, q, J=7.0 Hz), 3.76 (2H, m), 4.64 (1H, m), 5.24 (1H, d, J=5.0 Hz), 5.85 (1H, dd, J=5.0 Hz, 8.0 Hz), 6.84 (1H, s), 7.13–7.69 (10H, m), 8.18 (2H, broad s), 9.44, 9.51 (1H, d, J=8.0 Hz).

(28) Benzhydryl 7-[2-phenyl-2-tert-butoxycarbonylmethoxyiminoacetamido]-3-ethylthio-3-cephem-4-carboxylate (syn isomer), mp. 98° to 103° C.

IR (Nujol): 3280, 1779, 1723, 1710, 1674 cm⁻¹.

NMR (DMSO-$d_6$, δ): 1.13 (3H, t, J=7 Hz), 2.84 (2H, q, J=7 Hz), 3.77 (2H, broad s), 4.64 (2H, broad s), 5.31 (1H, d, J=5 Hz), 5.82 (1H, dd, J=5 Hz, 8 Hz), 6.86 (1H, s), 7.40 (15H, m), 9.70 (1H, d, J=8 Hz).

(29) Benzhydryl 7-[2-(2-formamidothiazol-4-yl)-2-tert-butoxycarbonylmethoxyiminoacetamido]-3-propylthio-3-cephem-4-carboxylate (syn isomer).

IR (Nujol): 3240, 3130, 1780, 1722, 1684 cm⁻¹.

NMR (DMSO-$d_6$, δ): 0.90 (3H, t, J=7 Hz), 1.42 (9H, s), 1.3–1.5 (2H, m), 2.8 (2H, t, J=7 Hz), 3.73 (2H, broad s), 4.57 (2H, broad s), 5.27 (1H, d, J=5 Hz), 5.80 (1H, dd, J=5 Hz, 8 Hz), 6.86 (1H, s), 7.3 (10H, m), 8.50 (1H, s), 9.60 (1H, d, J=8 Hz), 12.6 (1H, broad, s).

(30) Benzhydryl 7-[2-(2-formamidothiazol-4-yl)-2-(1-tert-butoxycarbonylethoxyimino)acetamido]-3-methylthio-3-cephem-4-carboxylate (syn isomer).

IR (Nujol): 3200, 1780, 1680 (broad), 1540 cm⁻¹.

NMR (DMSO-$d_6$, δ): 1.37, 1.60 (12H, m), 2.35 (3H, s), 4.65 (1H, m), 3.83 (2H, s), 5.23 (1H, d, J=5 Hz), 5.87 (1H, dd, J=5 Hz, 8 Hz), 6.85 (1H, s), 7.32 (10H, m), 7.45 (1H, s), 8.50 (1H, s), 9.50 and 9.58 (each ½H, d, J=8 Hz).

(31) Benzhydryl 7-[2-(2-formamido-5-chlorothiazol-4-yl)-2-tert-butoxycarbonylmethoxyaminoacetamido]-3-methylthio-3-cephem-4-carboxylate (syn isomer).

IR (Nujol): 3200, 1780, 1750, 1725, 1690, 1540 cm⁻¹.

NMR (DMSO-$d_6$, δ): 1.43 (9H, s), 2.33 (3H, s), 3.83 (2H, s), 4.67 (2H, s), 5.23 (1H, d, J=5 Hz), 5.92 (1H, dd, J=5 Hz, 8 Hz), 6.90 (1H, s), 7.47 (10H, m), 8.58 (1H, s), 9.68 (1H, d, J=8 Hz), 12.92 (1H, broad s).

(32) Benzhydryl 7-[2-(2-formamidothiazol-4-yl)-2-(1-tert-butoxycarbonylethoxyimino)acetamido]-3-ethylthio-3-cephem-4-carboxylate (syn isomer)

IR (Nujol): 3150, 1780, 1715, 1680 cm⁻¹.

NMR (DMSO-$d_6$, δ): 1.02 (3H, d, J=7.0 Hz) 1.21–1.67 (12H, m), 2.86 (2H, q, J=7.0 Hz), 3.80 (2H, broad s), 4.67 (1H, m), 5.31 (1H, d, J=5.0 Hz), 5.90 (1H, dd, J=5.0 Hz, 8.0 Hz), 6.91 (1H, s), 7.16–7.74 (11H, m), 8.55 (1H, s), 9.56, 9.63 (1H, d, J=8.0 Hz), 12.72 (1H, broad s).

(33) Benzhydryl 7-[2-(6-formamidopyridin-2-yl)-2-tert-butoxycarbonylmethoxyiminoacetamido]-3-methylthio-3-cephem-4-carboxylate (syn isomer), mp. 109° to 110° C. (dec.).

IR (Nujol): 3250, 1775, 1750 (shoulder), 1690 (broad) cm⁻¹.

NMR (DMSO-d$_6$, δ): 1.46 (9H, s), 2.33 (3H, s), 3.83 (2H, broad s), 4.68 (2H, broad s), 5.20 (1H, d, J=5 Hz), 5.90 (1H, dd, J=5 Hz, 8 Hz), 6.87 (1H, s), 7.4 (10H, m), 7.3-8.0 (3H, m), 9.47 (1H, d, J=8 Hz), 10.5 (1H, broad s).

(34) benzhydryl 7-[2-(2-furyl)-2-tert-butoxycarbonylmethoxyiminoacetamido]-3-methylthio-3-cephem-4-carboxylate (syn isomer).

IR (Nujol): 3250, 1780, 1725, 1685, 1540 cm$^{-1}$.

NMR (DMSO-d$_6$, δ): 1.42 (9H, s), 2.33 (3H, s), 3.80 (2H, s), 4.62 (2H, s), 5.22 (1H, d, J=5 Hz), 5.77 (1H, dd, J=5 Hz, 8 Hz), 6.58 (1H, dd, J=2 Hz, 4 Hz), 6.75 (1H, d, J=4 Hz), 6.83 (1H, s), 7.32 (10H, m), 7.82 (1H, d, J=2 Hz), 9.70 (1H, d, J=8 Hz).

(35) Benzhydryl 7-[2-(2-amino-5-chlorothiazol-4-yl)-2-tert-butoxycarbonylmethoxyiminoacetamido]-3-ethylthio-3-cephem-4-carboxylate (syn isomer,), mp. 171° to 176° C.

IR (Nujol): 3300, 1770 (broad), 1724, 1688 cm$^{-1}$.

(36) Benzhydryl 7-[2-(6-aminopyridin-2-yl)-2-tert-butoxycarbonylmethoxyiminoacetamido]-3-ethylthio-3-cephem-4-carboxylate (syn isomer, 2.4 g), mp. 121° to 128° C. (dec.).

IR (Nujol): 3350, 1774, 1728, 1684 cm$^{-1}$.

(37) Benzhydryl 7-[2-(2-aminothiazol)-4-yl)-2-(1-tert-butoxycarbonylethoxyimino)acetamido]-3-methylthio-3-cephem-4-carboxylate (syn isomer).

IR (Nujol): 3250, 1780, 1720, 1680, 1620, 1540 cm$^{-1}$.

(38) Benzhydryl 7-[2-(2-amino-5-chlorothiazol-4-yl)-2-tert-butoxycarbonylmethoxyiminoacetamido]-3-methylthio-3-cephem-4-carboxylate (syn isomer).

IR (Nujol): 3300, 1770, 1730, 1690, 1620, 1540 cm$^{-1}$.

(39) Benzhydryl 7-[2-(2-aminothiazol-4-yl)-2-(1-tert-butoxycarbonylethoxyimino)acetamido]-3-ethylthio-3-cephem-4-carboxylate (syn isomer).

IR (Nujol): 1775, 1710, 1680, 1610 cm$^{-1}$.

(40) Benzhydryl 7-[2-(2-aminothiazol-4-yl)-2-tert-butoxycarbonylmethoxyaminoacetamido]-3-propylthio-3-cephem-4-carboxylate (syn isomer).

IR (Nujol): 3260, 1778, 1723, 1680 cm$^{-1}$.

(41) Benzhydryl 7-[2-(6-aminopyridin-2-yl)-2-tert-butoxycarbonylmethoxyiminoacetamido]-3-methylthio-3-cephem-4-carboxylate (syn isomer). mp. 97° to 101° C. (dec.).

IR (Nujol): 3300, 1777 (broad), 1688, 1616 cm$^{-1}$.

(42) 7-[2-(5-amino-1,2,4-thiadiazol-3-yl)-2-carboxymethoxyiminoacetamido]-3-methylthio-3-cephem-4-carboxylic acid (syn isomer,), mp. 173° to 176° C. (dec.).

IR (Nujol): 3380, 3290, 1764, 1722, 1672, 1644 cm$^{-1}$.

(43) 7-[2-(2-amino-5-chlorothiazol-4-yl)-2-carboxymethoxyiminoacetamido]-3-ethylthio-3-cephem-4-carboxylic acid (syn isomer,), mp. 193° to 195° C. (dec.).

IR (Nujol): 3400, 3200, 1775, 1691, 1657 cm$^{-1}$.

(44) 7-[2-(6-Aminopyridin-2-yl)-2-carboxymethoxyiminoacetamido]-3-ethylthio-3-cephem-4-carboxylic acid (syn isomer, ), mp. 164° to 167° C. (dec.).

IR (Nujol): 3300, 3180, 1773 (shoulder), 1765, 1663 cm$^{-1}$.

(45) 7-[2-Phenyl-2-carboxymethoxyiminoacetamido]-3-ethylthio-3-cephem-4-carboxylic acid (syn isomer, ), mp. 103° to 107° C. (dec.).

IR (Nujol): 3250, 1760 (broad), 1674 (broad) cm$^{-1}$.

(46) 7-[2-(5-Amino-1,2,4-thiadiazol-3-yl)-2-carboxymethoxyiminoacetamido]-3-ethylthio-3-cephem-4-carboxylic acid (syn isomer), mp. 163° to 166° C. (dec.).

IR (Nujol): 3380, 3270, 1760, 1718, 1669, 1640 cm$^{-1}$.

(47) 7-[2-(5-Amino-1,2,4-thiadiazol-3-yl)-2-(1-carboxyethoxyimino)acetamido]-3-ethylthio-3-cephem-4-carboxylic acid (syn isomer).

IR (Nujol): 3300, 3180, 1760, 1670, 1620 cm$^{-1}$.

(48) 7-[2-(2-Aminothiazol-4-yl)-2-carboxymethoxyiminoacetamido]-3-propylthio-3-cephem-4-carboxylic acid (syn isomer), mp. 125° to 128° C. (dec.).

IR (Nujol): 3300, 1760 (broad), 1665 (broad) cm$^{-1}$.

(49) 7-[2-(2-Aminothiazol-4-yl)-2-(1-carboxyethoxyimino)acetamido]-3-ethylthio-3-cephem-4-carboxylic acid (syn isomer).

IR (Nujol): 3280, 3180, 1760, 1670, 1630 cm$^{-1}$. (50) 7-[2-(2-Aminothiazol-4-yl)-2-(1-carboxyethoxyimino)acetamido]-3-methylthio-3-cephem-4-carboxylic acid (syn isomer), mp. 110° to 115° C. (dec.).

IR (Nujol): 3300, 1760, 1670, 1530 cm$^{-1}$.

(51) 7-[2-(2-Amino-5-chlorothiazol-4-yl)-2-(carboxymethoxyiminoacetamido]-3-methylthio-3-cephem-4-carboxylic acid (syn isomer), mp. 178° C. (dec.).

IR (Nujol): 3400, 3200, 1770, 1690, 1655, 1620, 1530 cm$^{-1}$.

(52) 7-[2-(6-aminopyridin-2-yl)-2-carboxymethoxyiminoacetamido]-3-methylthio-3-cephem-4-carboxylic acid (syn isomer), mp. 111° to 116° C. (dec.).

IR (Nujol): 3300, 3150, 1760, 1660 (broad), 1618 cm$^{-1}$.

(53) 7-[2-(2-Furyl-2-carboxymethoxyiminoacetamido]-3-methylthio-3-cephem-4-carboxylic acid (syn isomer).

IR (Nujol): 3200, 1760, 1670, 1530 cm$^{-1}$.

(54) Benzhydryl 7-[2-(t-butoxycarbonylmethoxyimino)-2-(1,2,4-thiadiazol-3-yl) acetamido]-3-methyethio-3-cephem-4-carboxylate (syn isomer).

IR(Nujol): 1760(broad), 1680, 1630 cm$^{-1}$.

NMR (DMSO-d$_6$, δ): 1.42 (9H, S), 2.30 (3H, S), 3.73 (2H, S), 4.71 (2H, S), 5.19 (1H, d, J=5.0 HZ), 5.88 (1H, d-d, J=5.0 HZ, 8.0 HZ) 6.82 (1H, S), 7.30 (10H, m), 9.67 (1H, d, J=8.0 HZ), 10.26 (1H, S).

(55) 7-[2-carboxymethoxyimino-2-(1,2,4-thiadiazol-3-yl)-acetamido]-3-methylthio-3-cephem-4-carboxylic acid (syn isomer).

IR (Nujol): 1760, 1700, 1660 cm$^{-1}$.

EXAMPLE 7

To a solution of benzhydryl 7-[2-(2-formamidothiazol-4-yl)-2-(tert-butoxycarbonylmethoxyimino)acetamido]-3-methylthio-3-cephem-4-carboxylate-1-oxide (syn isomer) (1.5 g) in N,N-dimethylformamide (15 ml) was added phosphorus trichloride (0.18 ml) at −30° C. The mixture was stirred at the same temperature for 15 minutes. The resulting solution was poured into water (40 ml) and the precipitates were collected by filtration and dried under reduced pressure to give benzhydryl 7-[2-(2-formamidothiazol-4-yl)-2-(tert-butoxycarbonylmethoxyimino)acetamido]-3-methylthio-3-cephem-4-carboxylate (syn isomer) (1.31 g), mp. 151° to 157° C.

IR (Nujol): 3250, 1780, 1690 cm$^{-1}$.

EXAMPLE 8

The following compounds were prepared according to a similar manner to that of Example 7.

(1) Benzhydryl 7-[2-(2-aminothiazol-4-yl)-2-(methoxycarbonylmethoxyimino)acetamido]-3-methylthio-3-cephem-4-carboxylate (syn isomer).

IR (Nujol): 1770, 1670, 1610 cm$^{-1}$.

(2) 7-[2-(2-Aminothiazol-4-yl)-2-(methoxycarbonylmethoxyimino)acetamido]-3-methylthio-3-cephem-4-carboxylic acid (syn isomer).

IR (Nujol): 3250, 1765, 1720, 1650 cm$^{-1}$.

(3) 7-[2-(2-Aminothiazol-4-yl)-2-(carboxymethoxyimino)acetamido]-3-methylthio-3-cephem-4-carboxylic acid (syn isomer), mp. 183° to 186° C. (dec.).

IR (Nujol): 3300, 1760, 1665 cm$^{-1}$.

(4) 7-[2-Benzhydryloxycarbonylmethoxyimino-2-(2-formamidothiazol-4-yl)acetamido]-3-methylthio-3-cephem-4-carboxylic acid (syn isomer).

IR (Nujol): 3270, 1770, 1740, 1650 (broad) cm$^{-1}$.

(5) Sodium 7-[2-(2-aminothiazol-4-yl)-2-benzhydryloxycarbonylmethoxyiminoacetamido]-3-methylthio-3-cephem-4-carboxylate (syn isomer).

IR (Nujol): 1730 (broad), 1670 cm$^{-1}$.

(6) Pivaloyloxymethyl 7-[2-(2-aminothiazol-4-yl)-2-benzhydryloxycarbonylmethoxyiminoacetamido]-3-methylthio-3-cephem-4-carboxylate (syn isomer)

IR (Nujol): 3280, 3180, 1740 (broad), 1670, 1620 cm$^{-1}$.

(7) Pivaloyloxymethyl 7-[2-(2-aminothiazol-4-yl)-2-carboxymethoxyiminoacetamido]-3-methylthio-3-cephem-4-carboxylate (syn isomer)

IR (Nujol): 3300, 3200, 1770, 1750, 1670 cm$^{-1}$.

(8) Benzhydryl 7-[2-(2-formamidothiazol-4-yl)-2-(tert-butoxycarbonylmethoxyimino)acetamido]-3-methylthio-3-cephem-4-carboxylate (anti isomer).

IR (Nujol): 3250, 1760 (broad), 1685 cm$^{-1}$.

(9) Benzhydryl 7-[2-(2-aminothiazol-4-yl)-2-(tert-butoxycarbonylmethoxyimino)acetamido]-3-methylthio-3-cephem-4-carboxylate (anti isomer).

IR (Nujol): 3300, 1760, 1685, 1610 cm$^{-1}$.

(10) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$.

(11) 7-[2-(2-Methylaminothiazol-4-yl)-2-methoxycarbonyl-methoxyimino)acetamido]-3-methylthio-3-cephem-4-carboxylic acid (syn isomer).

IR (Nujol): 3250, 1785, 1755, 1645 cm$^{-1}$.

(12) 7-[2-(2-Methylaminothiazol-4-yl)-2-(carboxymethoxyimino)acetamido]-3-methylthio-3-cephem-4-carboxylic acid (syn isomer).

NMR (DMSO-d$_6$, δ): 2.38 (3H, s), 2.83 (3H, s), 3.77 (2H, s), 4.65 (2H, s), 5.17 (1H, d, J=5 Hz), 5.70 (1H, dd, J=5, 8 Hz), 6.90 (1H, s), 9.45 (1H, d, J=8 Hz).

(13) Benzhydryl 7-[2-(t-butoxycarbonylmethoxyimino)-2-(4-thiazolyl)acetamido]-3-methylthio-3-cephem-4-carboxylate (syn isomer).

IR (Nujol): 3270, 1780, 1720, 1655 cm$^{-1}$.

(14) 7-[2-(Carboxymethoxyimino)-2-(4-thiazolyl)acetamido]-3-methylthio-3-cephem-4-carboxylic acid (syn isomer).

IR (Nujol): 1760, 1670 cm$^{-1}$.

(15) Benzhydryl 7-[2-(t-butoxycarbonylmethoxyimino)-2-(4-thiazolyl)acetamido]-3-ethylthio-3-cephem-4-carboxylate (syn isomer).

IR (Nujol): 3270, 1765, 1750, 1695, 1680, 1650 cm$^{-1}$.

(16) 7-[2-(Carboxymethoxyimino)-2-(4-thiazolyl)acetamido]-3-ethylthio-3-cephem-4-carboxylic acid (syn isomer).

IR (Nujol): 1760, 1670 cm$^{-1}$.

(17) Benzhydryl 7-[2-(tert-butoxycarbonylmethoxyimino)-2-(1,2,5-thiadiazol-3-yl)acetamido]-3-methylthio-3-cephem-4-carboxylate (syn isomer).

IR (Nujol): 3250, 1765, 1730, 1680 cm$^{-1}$.

(18) 7-[2-(Carboxymethoxyimino)-2-(1,2,5-thiadiazol-3-yl)acetamido]-3-methylthio-3-cephem-4-carboxylic acid (syn isomer).

IR (Nujol): 3250, 1775, 1680 cm$^{-1}$.

(19) Benzhydryl 7-[2-(tert-butoxycarbonylmethoxyimino)-2-(2-naphthyl)acetamido]-3-methylthio-3-cephem-4-carboxylate (syn isomer).

IR (Nujol): 3300, 1770, 1720, 1680, 1540 cm$^{-1}$.

(20) 7-[2-Carboxymethoxyimino-2-(2-naphthyl)acetamido]-3-methylthio-3-cephem-4-carboxylic acid (syn isomer).

IR (Nujol): 3300, 1760, 1680, 1540 cm$^{-1}$.

(21) Benzhydryl 7-[2-(2-formamidothiazol-4-yl)-2-tert-butoxycarbonylmethoxyiminoacetamido]-3-methylthio-3-cephem-4-carboxylate (syn isomer ). mp. 151°-157° C.

IR (Nujol): 3250, 1780, 1690 cm$^{-1}$.

(22) Benzhydryl 7-[2-(2-aminothiazol-4-yl)-2-tert-butoxycarbonylmethoxyiminoacetamido]-3-methylthio-3-cephem-4-carboxylate (syn isomer). mp. 148°-155° C.

IR (Nujol): 3300, 1778, 1685 cm$^{-1}$.

(23) Benzhydryl 7-[2-(2-formamidothiazol-4-yl)-2-tert-butoxycarbonylmethoxyiminoacetamido]-3-ethylthio-3-cephem-4-carboxylate (syn isomer). mp 173°-176° C.

IR (Nujol): 3250, 1780, 1745, 1726, 1690 cm$^{-1}$. (24) Benzhydryl 7-[2-(2-aminothiazol-4-yl)-2-tert-butoxycarbonylmethoxyiminoacetamido]-3-ethylthio-3-cephem-4-carboxylate (syn isomer). mp 165°-169° C.

IR (Nujol): 3250, 1780, 1728, 1685 cm$^{-1}$.

(25) 7-[2-(2-Aminothiazol-4-yl)-2-carboxymethoxyiminoacetamido]-3-methylthio-3-cephem-4-carboxylic acid (syn isomer). mp. 183°-186° C. (dec.).

IR (Nujol): 3300, 1760, 1665 cm$^{-1}$.

(26) 7-[2-(2-Aminothiazol-4-yl)-2-carboxymethoxyiminoacetamido]-3-ethylthio-3-cephem-4-carboxylic acid (syn isomer), mp. 215°-218° C. (dec.).

IR (Nujol): 3280, 1763, 1670 cm$^{-1}$.

(27) Benzhydryl 7-[2-(5-amino-1,2,4-thiadiazol-3-yl)-2-tert-butoxycarbonylmethoxyiminoacetamido]-3-methylthio-3-cephem-4-carboxylate (syn isomer), mp. 123°-129° C. (dec.).

IR (Nujol): 3300, 1776, 1689, 1615 cm$^{-1}$.

(28) Benzhydryl 7-[2-(2-formamido-5-chlorothiazol-4-yl)-2-tert-butoxycarbonylmethoxyiminoacetamido]-3-ethylthio-3-cephem-4-carboxylate (syn isomer), mp. 143° to 148° C.

IR (Nujol): 3250, 1780, 1750, 1728, 1683 cm$^{-1}$.

(29) Benzhydryl 7-[2-(6-formamidopyridin-2-yl)-2-tert-butoxycarbonylmethoxyiminoacetamido]-3-ethylthio-3-cephem-4-carboxylate (syn isomer), mp. 113° to 123° C.

IR (Nujol): 3250, 1774 (broad), 1688 (broad) cm$^{-1}$.

(30) Benzhydryl 7-[2-(5-amino-1,2,4-thiadiazol-3-yl)-2-tert-butoxycarbonylmethoxyiminoacetamido]-3-ethylthio-3-cephem-4-carboxylate (syn isomer), mp. 103° to 108° C. (dec.).

IR (Nujol): 3300, 1775, 1727, 1690, 1620 cm$^{-1}$.

(31) Benzhydryl 7-[2-(5-amino-1,2,4-thiadiazol-3-yl)-2-(1-tert-butoxycarbonylethoxyimino)acetamido]-3-ethylthio-3-cephem-4-carboxylate (syn isomer).

IR (Nujol): 1770, 1720, 1685, 1610 cm$^{-1}$.

(32) Benzhydryl 7-[2-phenyl-2-tert-butoxycarbonylmethoxyiminoacetamido]-3-ethylthio-3-cephem-4-carboxylate (syn isomer), mp. 98° to 103° C.

IR (Nujol): 3280, 1779, 1723, 1710, 1674 cm$^{-1}$

(33) Benzhydryl 7-[2-(2-formamidothiazol-4-yl)-2-tert-butoxycarbonylmethoxyiminoacetamido]-3-propylthio-3-cephem-4-carboxylate (syn isomer).

IR (Nujol): 3240, 3130, 1780, 1722, 1684 cm$^{-1}$.

(34) Benzhydryl 7-[2-(2-formamidothiazol-4-yl)-2-(1-tert-butoxycarbonylethoxyimino)acetamido]-3-methylthio-3-cephem-4-carboxylate (syn isomer).

IR (Nujol): 3200, 1780, 1680 (broad), 1540 cm$^{-1}$.

(35) Benzhydryl 7-[2-(2-formamido-5-chlorothiazol-4-yl)-2-tert-butoxycarbonylmethoxyaminoacetamido]-3-methylthio-3-cephem-4-carboxylate (syn isomer).

IR (Nujol): 3200, 1780, 1750, 1725, 1690, 1540 cm$^{-1}$.

(36) Benzhydryl 7-[2-(2-formamidothiazol-4-yl)-2-(1-tert-butoxycarbonylethoxyimino)acetamido]-3-ethylthio-3-cephem-4-carboxylate (syn isomer).

IR (Nujol): 3150, 1780, 1715, 1680 cm$^{-1}$.

(37) Benzhydryl 7-[2-(6-formamidopyridin-2-yl)-2-tert-butoxycarbonylmethoxyiminoacetamido]-3-methylthio-3-cephem-4-carboxylate (syn isomer), mp. 109° to 110° C. (dec.).

IR (Nujol): 3250, 1775, 1750 (shoulder), 1690 (broad) cm$^{-1}$.

(38) Benzhydryl 7-[2-(2-furyl)-2-tert-butoxycarbonylmethoxyiminoacetamido]-3-methylthio-3-cephem-4-carboxylate (syn isomer).

IR (Nujol): 3250, 1780, 1725, 1685, 1540 cm$^{-1}$.

(39) Benzhydryl 7-[2-(2-amino-5-chlorothiazol-4-yl)-2-tert-butoxycarbonylmethoxyiminoacetamido]-3-ethylthio-3-cephem-4-carboxylate (syn isomer, ), mp. 171° to 176° C.

IR (Nujol): 3300, 1770 (broad), 1724, 1688 cm$^{-1}$.

(40) Benzhydryl 7-[2-(6-aminopyridin-2-yl)-2-tert-butoxycarbonylmethoxyiminoacetamido]-3-ethylthio-3-cephem-4-carboxylate (syn isomer ), mp. 121° to 128° C. (dec.).

IR (Nujol): 3350, 1774, 1728, 1684 cm$^{-1}$.

(41) Benzhydryl 7-[2-(2-aminothiazol-4-yl)-2-(1-tert-butoxycarbonylethoxyimino)acetamido]-3-methylthio-3-cephem-4-carboxylate (syn isomer).

IR (Nujol): 3250, 1780, 1720, 1680, 1620, 1540 cm$^{-1}$.

(42) Benzhydryl 7-[2-(2-amino-5-chlorothiazol-4-yl)-2-tert-butoxycarbonylmethoxyiminoacetamido]-3-methylthio-3-cephem-4-carboxylate (syn isomer).

IR (Nujol): 3300, 1770, 1730, 1690, 1620, 1540 cm$^{-1}$.

(43) Benzhydryl 7-[2-(2-aminothiazol-4-yl)-2-(1-tert-butoxycarbonylethoxyimino)acetamido]-3-ethylthio-3-cephem-4-carboxylate (syn isomer).

IR (Nujol): 1775, 1710, 1680, 1610 cm$^{-1}$.

(44) Benzhydryl 7-[2-(2-aminothiazol-4-yl)-2-tert-butoxycarbonylmethoxyiminoacetamido]-3-propylthio-3-cephem-4-carboxylate (syn isomer).

IR (Nujol): 3260, 1778, 1723, 1680 cm$^{-1}$.

(45) Benzhydryl 7-[2-(6-aminopyridin-2-yl)-2-tert-butoxycarbonylmethoxyiminoacetamido]-3-methylthio-3-cephem-4-carboxylate (syn isomer). mp. 97° to 101° C. (dec.).

IR (Nujol): 3300, 1777 (broad), 1688, 1616 cm$^{-1}$.

(46) 7-[2-(5-Amino-1,2,4-thiadiazol-3-yl)-2-carboxymethoxyiminoacetamido]-3-methylthio-3-cephem-4-carboxylic acid (syn isomer, ), mp. 173° to 176° C. (dec.).

IR (Nujol): 3380, 3290, 1764, 1722, 1672, 1644 cm$^{-1}$.

(47) 7-[2-(2-Amino-5-chlorothiazol-4-yl)-2-carboxymethoxyiminoacetamido]-3-ethylthio-3-cephem-4-carboxylic acid (syn isomer, ), mp. 193° to 195° C. (dec.).

IR (Nujol): 3400, 3200, 1775, 1691, 1657 cm$^{-1}$.

(48) 7-[2-(6-aminopyridin-2-yl)-2-carboxymethoxyiminoacetamido]-3-ethylthio-3-cephem-4-carboxylic acid (syn isomer, ), mp. 164° to 167° C. (dec.).

IR (Nujol): 3300, 3180, 1773 (shoulder), 1765, 1663 cm$^{-1}$.

(49) 7-[2-phenyl-2-carboxymethoxyiminoacetamido]-3-ethylthio-3-cephem-4-carboxylic acid (syn isomer, ), mp. 103° to 107° C. (dec.).

IR (Nujol): 3250, 1760 (broad), 1674 (broad) cm$^{-1}$.

(50) 7-[2-(5-Amino-1,2,4-thiadiazol]-3-yl)-2-carboxymethoxyiminoacetamido]-3-ethylthio-3-cephem-4-carboxylic acid (syn isomer), mp. 163° to 166° C. (dec.).

IR (Nujol): 3380, 3270, 1760, 1718, 1669, 1640 cm$^{-1}$.

(51) 7-[2-(5-Amino-1,2,4-thiadiazol-3-yl)-2-(1-carboxyethoxyimino)acetamido]-3-ethylthio-3-cephem-4-carboxylic acid (syn isomer).

IR (Nujol): 3300, 3180, 1760, 1670, 1620 cm$^{-1}$.

(52) 7-[2-(2-Aminothiazol-4-yl)-2-carboxymethoxyiminoacetamido]-3-propylthio-3-cephem-4-carboxylic acid (syn isomer), mp. 125° to 128° C. (dec.).

IR (Nujol): 3300, 1760 (broad), 1665 (broad) cm$^{-1}$.

(53) 7-[2-(2-Aminothiazol-4-yl)-2-(1-carboxyethoxyimino)acetamido]-3-ethylthio-3-cephem-4-carboxylic acid (syn isomer).

IR (Nujol): 3280, 3180, 1760, 1670, 1630 cm$^{-1}$. (54) 7-[2-(2-Aminothiazol-4-yl)-2-(1-carboxyethoxyimino)acetamido]-3-methylthio-3-cephem-4-carboxylic acid (syn isomer), mp. 110° to 115° C. (dec.).

IR (Nujol): 3300, 1760, 1670, 1530 cm$^{-1}$.

(55) 7-[2-(2-Amino-5-chlorothiazol-4-yl)-2-(carboxymethoxyiminoacetamido]-3-methylthio-3-cephem-4-carboxylic acid (syn isomer), mp. 178° C. (dec.).

IR (Nujol): 3400, 3200, 1770, 1690, 1655, 1620, 1530 cm$^{-1}$.

(56) 7-[2-(6-aminopyridin-2-yl)-2-carboxymethoxyiminoacetamido]-3-methylthio-3-cephem-4-carboxylic acid (syn isomer), mp. 111° to 116° C. (dec.).

IR (Nujol): 3300, 3150, 1760, 1660 (broad), 1618 cm$^{-1}$.

(57) 7-[2-(2-Furyl-2-carboxymethoxyiminoacetamido]-3-methylthio-3-cephem-4-carboxylic acid (syn isomer).

IR (Nujol): 3200, 1760, 1670, 1530 cm$^{-1}$.

(58) Benzhydryl 7-[2-(t-butoxycarbonylmethoxyimino)-2-(1,2,4-thiadiazol-3-yl) acetamido]-3-methyethio-3-cephem-4-carboxylate (syn isomer).

IR (Nujol): 1760(broad), 1680, 1630 cm$^{-1}$.

(59) 7-[2-carboxymethoxyimino-2-(1,2,4-thiadiazol-3-yl)-acetamido]-3-methylthio-3-cephem-4-carboxylic acid (syn isomer).

IR (Nujol): 1760, 1700, 1660 cm$^{-1}$.

EXAMPLE 9

A mixture of benzhydryl 7-[4-chloro-2-(methoxycarbonylmethoxyimino)-3-oxobutyramido]-3-methylthio-3-cephem-4-carboxylate (syn isomer) (18.97 g), thiourea (4.56 g) and sodium acetate (7.38 g) in tetrahydrofuran (150 ml) and water (80 ml) was stirred at 40° to 45° C. for 2 hours. Ethyl acetate (300 ml) was added to the reaction mixture at room temperature and the organic layer was separated. The organic layer was washed with brine and dried over magnesium sulfate. The solution was evaporated and the residue was triturated with ether to give benzhydryl 7-[2-(2-aminothiazol-4-yl)-2-(methoxycarbonylmethoxyimino)acetamido]-3-methylthio-3-cephem-4-carboxylate (syn isomer) (17.5 g).

IR (Nujol): 1770, 1670, 1610 cm$^{-1}$

NMR (DMSO-d$_6$, δ): 2.32 (3H, s), 3.65 (2H, s), 3.80 (2H, s), 4.73 (2H, s), 5.20 (1H, d, J=5 Hz), 5.80 (1H, dd, J=5, 8 Hz), 6.85 (1H, s), 6.88 (1H, s), 7.07–7.73 (10H, m), 9.60 (1H, d, J=8 Hz).

EXAMPLE 10

A mixture of 7-[4-chloro-2-(methoxycarbonylmethoxyimino)-3-oxobutyramido]-3-methylthio-3-cephem-4-carboxylic acid (syn isomer) (2.6 g), thiourea (0.91 g) and sodium acetate (2.46 g) in tetrahydrofuran (10 ml) and water (20 ml) was stirred at 40° to 45° C. for 3 hours. Water (50 ml) was added to the reaction mixture and the resultant solution was washed with ethyl acetate. The separated aqueous layer was acidified to pH 2.2 with 10% hydrochloric acid and the acidified aqueous solution was extracted with ethyl acetate-tetrahydrofuran (8:2). The organic layer was washed with brine and dried over magnesium sulfate. The solution was evaporated and the residue was triturated with ether to give 7-[2-(2-aminothiazol-4-yl)-2-(methoxycarbonylmethoxyimino)acetamido]-3-methylthio-3-cephem-4-carboxylic acid (syn isomer) (2.0 g).

IR (Nujol): 3250, 1765, 1720, 1650 cm$^{-1}$.

NMR (DMSO-d$_6$, δ): 2.35 (3H, s), 3.70 (3H, s), 3.76 (2H, s), 4.73 (2H, s), 5.16 (1H, d, J=5 Hz), 5.68 (1H, dd, J=5, 8 Hz), 6.00 (1H, s), 9.56 (1H, d, J=8 Hz).

EXAMPLE 11

A mixture of 7-[4-chloro-2-(methoxycarbonylmethoxyimino)-3-oxobutyramido]-3-methylthio-3-cephem-4-carboxylic acid (syn isomer) (4.3 g), N-methylthiourea (1.8 g) and sodium acetate (4.1 g) in water (20 ml) and tetrahydrofuran (40 ml) was stirred at 38° to 42° C. for 2.5 hours. Water (50 ml) was added to the reaction mixture and the resultant solution was washed with ethyl acetate. The separated aqueous layer was acidified to pH 2.3 with 10% hydrochloric acid and then extracted with ethyl acetate. The ethyl acetate layer was washed with brine and dried over magnesium sulfate. The solution was evaporated and the residue was triturated with ether to give 7-[2-(2-methylaminothiazol-4-yl)-2-(methoxycarbonylmethoxyimino)acetamido]-3-methylthio-3-cephem-4-carboxylic acid (syn isomer) (3.2 g).

IR (Nujol): 3250, 1785, 1755, 1645 cm$^{-1}$

NMR (DMSO-d$_6$, δ): 2.34 (3H, s), 2.83 (3H, s), 3.70 (3H, s), 3.76 (2H, s), 4.72 (2H, s), 5.15 (1H, d, J=5 Hz), 5.70 (1H, dd, J=5, 8 Hz), 6.90 (1H, s), 9.49 (1H, d, J=8 Hz).

EXAMPLE 12

The following compounds were prepared according to the similar manners to those of Examples 9 to 11.

(1) Benzhydryl 7-[2-(2-formamidothiazol-4-yl)-2-tert-butoxycarbonylmethoxyiminoacetamido]-3-methylthio-3-cephem-4-carboxylate (syn isomer), mp. 151° to 157° C.

IR (Nujol): 3250, 1780, 1690 cm$^{-1}$.

(2) 7-[2-(2-Aminothiazol-4-yl)-2-(carboxymethoxyimino)acetamido]-3-methylthio-3-cephem-4-carboxylic acid (syn isomer), mp. 183° to 186° C. (dec.).

IR (Nujol): 3300, 1760, 1665 cm$^{-1}$.

(3) 7-[2-Benzhydryloxycarbonylmethoxyimino-2-(2-formamidothiazol-4-yl)acetamido]-3-methylthio-3-cephem-4-carboxylic acid (syn isomer).

IR (Nujol): 3270, 1770, 1740, 1650 (broad) cm$^{-1}$.

(4) Sodium 7-[2-(2-aminothiazol-4-yl)-2-benzhydryloxycarbonylmethoxyiminoacetamido]-3-methylthio-3-cephem-4-carboxylate (syn isomer).

IR (Nujol): 1730 (broad), 1670 cm$^{-1}$.

(5) Pivaloyloxymethyl 7-[2-(2-aminothiazol-4-yl)-2-benzhydryloxycarbonylmethoxyiminoacetamido]-3-methylthio-3-cephem-4-carboxylate (syn isomer)

IR (Nujol): 3280, 3180, 1740 (broad), 1670, 1620 cm$^{-1}$.

(6) Pivaloyloxymethyl 7-[2-(2-aminothiazol-4-yl)-2-carboxymethoxyiminoacetamido]-3-methylthio-3-cephem-4-carboxylate (syn isomer).

IR (Nujol): 3300, 3200, 1770, 1750, 1670 cm$^{-1}$.

(7) Benzhydryl 7-[2-(2-formamidothiazol-4-yl)-2-(tert-butoxycarbonylmethoxyimino)acetamido]-3-methylthio-3-cephem-4-carboxylate (anti isomer).

IR (Nujol): 3250, 1760 (broad), 1685 cm$^{-1}$.

(8) Benzhydryl 7-[2-(2-aminothiazol-4-yl)-2-(tert-butoxycarbonylmethoxyimino)acetamido]-3-methylthio-3-cephem-4-carboxylate (anti isomer).

IR (Nujol): 3300, 1760, 1685, 1610 cm$^{-1}$.

(9) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$.

(10) 7-[2-(2-Methylaminothiazol-4-yl)-2-(carboxymethoxyimino)acetamido]-3-methylthio-3-cephem-4-carboxylic acid (syn isomer).

NMR (DMSO-d$_6$, δ): 2.38 (3H, s), 2.83 (3H, s), 3.77 (2H, s), 4.65 (2H, s), 5.17 (1H, d, J=5 Hz), 5.70 (1H, dd, J=5, 8 Hz), 6.90 (1H, s), 9.45 (1H, d, J=8 Hz).

(11) Benzhydryl 7-[2-(2-formamidothiazol-4-yl)-2-tert-butoxycarbonylmethoxyiminoacetamido]-3-methylthio-3-cephem-4-carboxylate (syn isomer, 2.4 g). mp. 151°–157° C.

IR (Nujol): 3250, 1780, 1690 cm$^{-1}$.

(12) Benzhydryl 7-[2-(2-aminothiazol-4-yl)-2-tert-butoxycarbonylmethoxyiminoacetamido]-3-methylthio-3-cephem-4-carboxylate (syn isomer) mp. 148°–155° C.

IR (Nujol): 3300, 1778, 1685 cm$^{-1}$.

(13) Benzhydryl 7-[2-(2-formamidothiazol-4-yl)-2-tert-butoxycarbonylmethoxyiminoacetamido]-3-ethylthio-3-cephem-4-carboxylate (syn isomer). mp 173°–176° C.

IR (Nujol): 3250, 1780, 1745, 1726, 1690 cm$^{-1}$.

(14) Benzhydryl 7-[2-(2-aminothiazol-4-yl)-2-tert-butoxycarbonylmethoxyiminoacetamido]-3-ethylthio-3-cephem-4-carboxylate (syn isomer). mp 165°–169° C.

IR (Nujol): 3250, 1780, 1728, 1685 cm$^{-1}$.

(15) 7-[2-(2-Aminothiazol-4-yl)-2-carboxymethoxyiminoacetamido]-3-methylthio-3-cephem-4-carboxylic acid (syn isomer). mp. 183°–186° C. (dec.).

IR (Nujol): 3300, 1760, 1665 cm$^{-1}$.

(16) 7-[2-(2-Aminothiazol-4-yl)-2-carboxymethoxyiminoacetamido]-3-ethylthio-3-cephem-4-carboxylic acid (syn isomer), mp. 215°–218° C. (dec.).

IR (Nujol): 3280, 1763, 1670 cm$^{-1}$.

(17) Benzhydryl 7-[2-(2-formamidothiazol-4-yl)-2-tert-butoxycarbonylmethoxyiminoacetamido]-3-propylthio-3-cephem-4-carboxylate (syn isomer).

IR (Nujol): 3240, 3130, 1780, 1722, 1684 cm$^{-1}$.

(18) Benzhydryl 7-[2-(2-formamidothiazol-4-yl)-2-(1-tert-butoxycarbonylethoxyimino)acetamido]-3-methylthio-3-cephem-4-carboxylate (syn isomer).

IR (Nujol): 3200, 1780, 1680 (broad), 1540 cm$^{-1}$.

(19) Benzhydryl 7-[2-(2-formamidothiazol-4-yl)-2-(1-tert-butoxycarbonylethoxyimino)acetamido]-3-ethylthio-3-cephem-4-carboxylate (syn isomer).

IR (Nujol): 3150, 1780, 1715, 1680 cm$^{-1}$.

(20) Benzhydryl 7-[2-(2-aminothiazol-4-yl)-2-(1-tert-butoxycarbonylethoxyimino)acetamido]-3-methylthio-3-cephem-4-carboxylate (syn isomer).

IR (Nujol): 3250, 1780, 1720, 1680, 1620, 1540 cm$^{-1}$.

(21) Benzhydryl 7-[2-(2-aminothiazol-4-yl)-2-(1-tert-butoxycarbonylethoxyimino)acetamido]-3-ethylthio-3-cephem-4-carboxylate (syn isomer).

IR (Nujol): 1775, 1710, 1680, 1610 cm$^{-1}$.

(22) Benzhydryl 7-[2-(2-aminothiazol-4-yl)-2-tert-butoxycarbonylmethoxyiminoacetamido]-3-propylthio-3-cephem-4-carboxylate (syn isomer).

IR (Nujol): 3260, 1778, 1723, 1680 cm$^{-1}$.

(23) 7-[2-(2-Aminothiazol-4-yl)-2-carboxymethoxyiminoacetamido]-3-propylthio-3-cephem-4-carboxylic acid (syn isomer), mp. 125° to 128° C. (dec.).

IR (Nujol): 3300, 1760 (broad), 1665 (broad) cm$^{-1}$.

(24) 7-[2-(2-Aminothiazol-4-yl)-2-(1-carboxyethoxyimino)acetamido]-3-ethylthio-3-cephem-4-carboxylic acid (syn isomer).

IR (Nujol): 3280, 3180, 1760, 1670, 1630 cm$^{-1}$.

(25) 7-[2-(2-Aminothiazol-4-yl)-2-(1-carboxyethoxyimino)acetamido]-3-methylthio-3-cephem-4-carboxylic acid (syn isomer), mp. 110° to 115° C. (dec.).

IR (Nujol): 3300, 1760, 1670, 1530 cm$^{-1}$.

EXAMPLE 13

To the solution of 7-[2-benzhydryloxycarblnylmethoxyimino-2-(2-formamidothiazol-4-yl)acetamido]-3-methylthio-3-cephem-4-carboxylic acid (syn isomer) (8.7 g) in methanol (80 ml) and tetrahydrofuran (60 ml) was added conc. hydrochloric acid (2.7 g) and the mixture was stirred for 3 hours at ambient temperature. To the resulting solution was added water (30 ml) and adjusted to pH 7.0 with saturated aqueous sodium carbonate. The solution was evaporated under reduced pressure. The precipitates were collected by filtration and washed with ethyl acetate, dried over phosphorus pentoxide to give sodium 7-[2-(2-aminothiazol-4-yl)-2-benzhydryloxycarbonylmethoxyiminoacetamido]-3-methylthio-3-cephem-4-carboxylate (syn isomer) (5.02 g).

IR (Nujol): 1730 (broad), 1670 cm$^{-1}$.

NMR (DMSO-d$_6$, δ): 2.14 (3H, s), 3.51 (2H, m), 4.83 (2H, s), 5.00 (1H, d, J=5.0 Hz), 5.57 (1H, dd, J=5.0 Hz, 8.0 Hz), 6.76 (1H, s), 6.84 (1H, s), 7.15-7.56 (10H, m), 9.45 (1H, d, J=8.0 Hz).

EXAMPLE 14

To a suspension of benzhydryl 7-[2-(2-formamidothiazol-4-yl)-2-tert-butoxycarbonylmethoxyiminoacetamido]-3-methylthio-3-cephem-4-carboxylate (syn isomer, 2.3 g) in methanol (69 ml) was added conc. hydrochloric acid (1.44 ml) at 35° C., and the suspension was stirred for an hour at the same temperature. The reaction mixture was adjusted to pH 7.0 with an aqueous saturated solution of sodium bicarbonate. Methanol as evaporated in vacuo, and the residue was dissolved in ethyl acetate. The ethyl acetate layer was washed with an aqueous saturated solution of sodium chloride and dried over magnesium sulfate. The solvent was evaporated in vacuo to give benzhydryl 7-[2-(2-aminothiazol-4-yl)-2-tert-butoxycarbonylmethoxyiminoacetamido]-3-methylthio-3-cephem-4-carboxylate (syn isomer, 1.76 g). mp. 148°-155° C.

IR (Nujol): 3300, 1778, 1685 cm$^{-1}$.

NMR (DMSO-d$_6$, δ): 1.43 (9H, s), 2.35 (3H, s), 3.80 (2H, m), 4.57 (2H, broad s), 5.21 (1H, d, J=5 Hz), 5.77 (1H, dd, J=5 Hz, 8 Hz), 6.83 (2H, s), 7.40 (10H, m), 9.47 (1H, d, J=8 Hz).

EXAMPLE 15

To a suspension of benzhydryl 7-[2-(2-formamido-5-chlorothiazol-4-yl)-2-tert-butoxycarbonylmethoxyiminoacetamido]-3-ethylthio-3-cephem-4-carboxylate (syn isomer, 2.7 g) in methanol (60 ml) was added conc. hydrochloric acid (1.5 ml) at 35° C. and the mixture was stirred for 90 minutes at the same temperature. The reaction mixture was adjusted to pH 6.0 with an aqueous solution of sodium bicarbonate. Methanol was evaporated under reduced pressure and the residue was dissolved into ethyl acetate. The ethyl acetate layer was washed with a saturated aqueous solution of sodium chloride and dried over magnesium sulfate. The solvent was evaporated under reduced pressure to give benzhydryl 7-[2-(2-amino-5-chlorothiazol-4-yl)-2-tert-butoxycarbonylmethoxyiminoacetamido]-3-ethylthio-3-cephem-4-carboxylate (syn isomer, 2.0 g), mp. 171° to 176° C.

IR (Nujol): 3300, 1770 (broad), 1724, 1688 cm$^{-1}$.

NMR (DMSO-d$_6$, δ): 1.12 (3H, t, J=7 Hz), 2.83 (2H, q, J=7 Hz), 3.75 (2H, m), 4.55 (2H, broad s), 5.20 (1H, d, J=5 Hz), 5.80 (1H, dd, J=5 Hz, 8 Hz), 6.83 (1H, s), 7.33 (10H, m), 9.40 (1H, d, J=8 Hz).

EXAMPLE 16

To a solution of benzhydryl 7-[2-(6-formamidopyridin-2-yl)-2-tert-butoxycarbonylmethoxyiminoacetamido]-3-ethylthio-3-cephem-4-carboxylate (syn isomer, 2.5 g) in methanol (100 ml) and tetrahydrofuran (25 ml) was added conc. hydrochloric acid (1.5 ml). The solution was stirred for 90 minutes at 30° to 35° C. The resultant solution was adjusted to pH 5.0 with a saturated aqueous solution of sodium bicarbonate and then methanol was evaporated under reduced pressure. The residual oil was dissolved in ethyl acetate. The ethyl acetate layer was washed with a saturated aqueous solution of sodium chloride, and dried over magnesium sulfate. The solvent was evaporated under reduced pressure to give benzhydryl 7-[2-(6-aminopyridin-2-yl)-2-tert-butoxycarbonylmethoxyiminoacetamido]-3-ethylthio-3-cephem-4-carboxylate (syn isomer, 2.4 g), mp. 121° to 128° C. (dec.).

IR (Nujol): 3350, 1774, 1728, 1684 cm$^{-1}$.

NMR (DMSO-d$_6$, δ): 1.12 (3H, t, J=7 Hz), 2.85 (2H, q, J=7 Hz), 3.78 (2H, broad s), 4.63 (2H, broad s), 5.27 (1H, d, J=5 Hz), 5.87 (1H, dd, J=5 Hz, 8 Hz), 6.51 (1H, d, J=8 Hz), 6.87 (1H, s), 6.87 (1H, d, J=7 Hz), 7.21-7.67 (11H, m), 9.40 (1H, d, J=8 Hz).

EXAMPLE 17

The following compounds were prepared according to a similar manner to that of Examples 13 to 16.

(1) Benzhydryl 7-[2-(2-aminothiazol-4-yl)-2-(methoxycarbonylmethoxyimino)acetamido]-3-methylthio-3-cephem-4-carboxylate (syn isomer).

IR (Nujol): 1770, 1670, 1610 cm$^{-1}$.

(2) 7-[2-(2-Aminothiazol-4-yl)-2-(methoxycarbonylmethoxyimino)acetamido]-3-methylthio-3-cephem-4-carboxylic acid (syn isomer).

IR (Nujol): 3250, 1765, 1720, 1650 cm$^{-1}$.

(3) Pivaloyloxymethyl 7-[2-(2-aminothiazol-4-yl)-2-benzhydryloxycarbonylmethoxyiminoacetamido]-3-methylthio-3-cephem-4-carboxylate (syn isomer).

IR (Nujol): 3280, 3180, 1740 (broad), 1670, 1620 cm$^{-1}$.

(4) Pivaloyloxymethyl 7-[2-(2-aminothiazol-4-yl)-2-carboxymethoxyiminoacetamido]-3-methylthio-3-cephem-4-carboxylate (syn isomer).

IR (Nujol): 3300, 3200, 1770, 1750, 1670 cm$^{-1}$.

(5) Benzhydryl 7-[2-(2-aminothiazol-4-yl)-2-(tert-butoxycarbonylmethoxyimino)acetamido]-3-methylthio-3-cephem-4-carboxylate (anti isomer).

IR (Nujol): 3300, 1760, 1685, 1610 cm$^{-1}$.

NMR (DMSO-d$_6$, δ): 1.43 (9H, s), 2.32 (3H, s), 3.80 (2H, m), 4.68 (2H, s), 5.17 (1H, d, J=5 Hz), 5.77 (1H, dd, J=5, 8 Hz), 6.83 (1H, s), 6.93–7.57 (10H, m), 7.57 (1H, s), 9.45 (1H, d, J=8 Hz).

(6) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$.

(7) 7-[2-(2-Aminothiazol-4-yl)-2-carboxymethoxyiminoacetamido]-3-methylthio-3-cephem-4-carboxylic acid (syn isomer), mp. 183° to 186° C. (dec.).

(8) 7-[2-(2-Aminothiazol-4-yl)-2-carboxymethoxyiminoacetamido]-3-methylthio-3-cephem-4-carboxylic acid (syn isomer). mp. 183°–186° C. (dec.).

IR (Nujol): 3300, 1760, 1665 cm$^{-1}$.

(9) benzhydryl 7-[2-(2-aminothiazol-4-yl)-2-tert-butoxycarbonylmethoxyiminoacetamido]-3-ethylthio-3-cephem-4-carboxylate (syn isomer). mp. 165°–169° C.

IR (Nujol): 3250, 1780, 1728, 1685 cm$^{-1}$.

NMR (DMSO-d$_6$, δ): 1.16 (3H, t, J=7 Hz), 2.90 (2H, q, J=7 Hz), 3.80 (2H, m), 4.61 (2H, broad s), 5.28 (1H, d, J=5 Hz), 5.80 (1H, dd, J=5 Hz, 8 Hz), 6.90 (2H, s), 7.40 (10H, m), 9.55 (1H, d, J=8 Hz).

(10) 7-[2-(2-aminothiazol-4-yl)-2-carboxymethoxyiminoacetamido]-3-ethylthio-3-cephem-4-carboxylic acid (syn isomer), mp. 215°–218° C. (dec.).

IR (Nujol): 3280, 1763, 1670 cm$^{-1}$.

(11) Benzhydryl 7-[2-(2-aminothiazol-4-yl)-2-(1-tert-butoxycarbonylethoxyimino)acetamido]-3-methylthio-3-cephem-4-carboxylate (syn isomer).

IR (Nujol): 3250, 1780, 1720, 1680, 1620, 1540 cm$^{-1}$.

NMR (DMSO-d$_6$, δ): 1.27–1.63 (12H, m), 2.35 (3H, s), 4.62 (1H, m), 3.83 (2H, s), 5.26 (1H, d, J=5 Hz), 5.87 (1H, dd, J=5 Hz, 8 Hz), 6.87, 6.90 (1H,ss), 7.37 (10H, m), 9.43 and 9.53 (each ½H, d, J=8 Hz).

(12) Benzhydryl 7-[2-(2-amino-5-chlorothiazol-4-yl)-2-tert-butoxycarbonylmethoxyiminoacetamido]-3-methylthio-3-cephem-4-carboxylate (syn isomer).

IR (Nujol): 3300, 1770, 1730, 1690, 1620, 1540 cm$^{-1}$.

NMR (DMSO-d$_6$, δ): 1.42 (9H, s), 2.32 (3H, s), 3.80 (2H, s), 4.57 (2H, s), 5.17 (1H, d, J=5 Hz), 5.83 (1H, dd, J=5 Hz, 8 Hz), 6.83 (1H, s), 7.33 (10H, m), 9.40 (1H,d, J=8 Hz).

(13) Benzhydryl 7-[2-(2-aminothiazol-4-yl)-2-(1-tert-butoxycarbonylethoxyimino)acetamido]-3-ethylthio-3-cephem-4-carboxylate (syn isomer).

IR (Nujol): 1775, 1710, 1680, 1610 cm$^{-1}$.

NMR (DMSO-d$_6$, δ): 1.08 (3H, d, J=7.0 Hz), 1.23–1.63 (12H, m), 2.89 (2H, q, J=7.0 Hz), 3.81 (2H, broad s), 4.62 (1H, m), 5.32 (1H, d, J=4.0 Hz), 5.86 (1H, dd, J=4.0 Hz, 8.0 Hz), 6.86 (1H, s), 6.92 (1H, s), 7.03–7.81 (10H, m), 9.46 and 9.53 (each ½H, d, J=8.0 Hz)

(14) Benzhydryl 7-[2-(2-aminothiazol-4-yl)-2-tert-butoxycarbonylmethoxyiminoacetamido]-3-propylthio-3-cephem-4-carboxylate (syn isomer).

IR (Nujol): 3260, 1778, 1723, 1680 cm$^{-1}$.

NMR (DMSO-d$_6$, δ): 0.90 (3H, t, J=7 Hz), 1.45 (9H, s), 1.4 (2H, m), 2.83 (2H, t, J=7 Hz), 3.75 (2H, broad s), 4.55 (2H, broad s), 5.26 (1H, d, J=5 Hz), 5.77 (1H, dd, J=5 Hz, 8 Hz), 6.85 (2H, s), 7.3 (10H, m), 9.45 (1H, d, J=8 Hz).

(15) Benzhydryl 7-[2-(6-aminopyridin-2-yl)-2-tert-butoxycarbonylmethoxyiminoacetamido]-3-methylthio-3-cephem-4-carboxylate (syn isomer). mp. 97° to 101° C. (dec.).

IR (Nujol): 3300, 1777 (broad), 1688, 1616 cm$^{-1}$

NMR (DMSO-d$_6$, δ): 1.43 (9H, s), 2.33 (3H, s), 3.80 (2H, broad s), 4.60 (2H, broad s), 5.20 (1H, d, J=5 Hz), 5.83 (1H, dd, J=5 Hz, 8 Hz), 6.48 (1H, d, J=8 Hz), 6.82 (1H, s), 6.83 (1H, d, J=7 Hz), 7.33 (11H, m), 9.38 (1H, d, J=8 Hz)

(16) Benzhydryl 7-[2-(5-amino-1,2,4-thiadiazol-3-yl)-2-tert-butoxycarbonylmethoxyiminoacetamido]-3-methylthio-3-cephem-4-carboxylate (syn isomer).

IR (Nujol): 3300, 1776, 1689, 1615 cm$^{-1}$.

(17) Benzhydryl 7-[2-(5-amino-1,2,4-thiadiazol-3-yl)-2-tert-butoxycarbonylmethoxyiminoacetamido]-3-ethylthio-3-cephem-4-carboxylate (syn isomer).

IR (Nujol): 3300, 1775, 1727, 1690, 1620 cm$^{-1}$.

(18) Benzhydryl 7-[2-(5-amino-1,2,4-thiadiazol-3-yl)-2-(1-tert-butoxycarbonylethoxyimino)acetamido]-3-ethylthio-3-cephem-4-carboxylate (syn isomer).

IR (Nujol): 1770, 1720, 1685, 1610 cm$^{-1}$.

(19) 7-[2-(5-Amino-1,2,4-thiadiazol-3-yl)-2-carboxymethoxyiminoacetamido]-3-methylthio-3-cephem-4-carboxylic acid (syn isomer)

IR (Nujol): 3380, 3290, 1764, 1722, 1672, 1644 cm$^{-1}$.

(20) 7-[2-(2-Amino-5-chlorothiazol-4-yl)-2-carboxymethoxyiminoacetamido]-3-ethylthio-3-cephem-4-carboxylic acid (syn isomer).

IR (Nujol): 3400, 3200, 1775, 1691, 1657 cm$^{-1}$.

(21) 7-[2-(6-Aminopyridin-2-yl)-2-carboxymethoxyiminoacetamido]-3-ethylthio-3-cephem-4-carboxylic acid (syn isomer).

IR (Nujol): 3300, 3180, 1773 (shoulder), 1765, 1663 cm$^{-1}$.

(22) 7-[2-(5-Amino-1,2,4-thiadiazol-3-yl)-2-carboxymethoxyiminoacetamido]-3-ethylthio-3-cephem-4-carboxylic acid (syn isomer).

IR (Nujol): 3380, 3270, 1760, 1718, 1669, 1640 cm$^{-1}$.

(23) 7-[2-(5-Amino-1,2,4-thiadiazol-3-yl)-2-(1-carboxyethoxyimino)acetamido]-3-ethylthio-3-cephem-4-carboxylic acid (syn isomer)

IR (Nujol): 3300, 3180, 1760, 1670, 1620 cm$^{-1}$.

(24) 7-[2-(2-Aminothiazol-4-yl)-2-carboxymethoxyiminoacetamido]-3-propylthio-3-cephem-4-carboxylic acid (syn isomer).

IR (Nujol): 3300, 1760 (broad), 1665 (broad) cm$^{-1}$.

(25) 7-[2-(2-Aminothiazol-4-yl)-2-(1-carboxyethoxyimino)acetamido]-3-ethylthio-3-cephem-4-carboxylic acid (syn isomer)

IR (Nujol): 3280, 3180, 1760, 1670, 1630 cm$^{-1}$.

(26) 7-[2-(2-Aminothiazol-4-yl)-2-(1-carboxyethoxyimino)acetamido]-3-methylthio-3-cephem-4-carboxylic acid (syn isomer)

IR (Nujol): 3300, 1760, 1670, 1530 cm$^{-1}$.

(27) 7-[2-(2-Amino-5-chlorothiazol-4-yl)-2-carboxymethoxyiminoacetamido]-3-methylthio-3-cephem-4-carboxylic acid (syn isomer).

IR (Nujol): 3400, 3200, 1770, 1690, 1655, 1620, 1530 cm$^{-1}$.

(28) 7-[2-(6-Aminopyridin-2-yl)-2-carboxymethoxyiminoacetamido]-3-methylthio-3-cephem-4-carboxylic acid (syn isomer).

IR (Nujol): 3300, 3150, 1760, 1660 (broad), 1618 cm$^{-1}$.

EXAMPLE 18

A mixture of 7-[2-(2-aminothiazol-4-yl)-2-methoxycarbonylmethoxyimino)acetamido]-3-methylthio-3-cephem-4-carboxylic acid (syn isomer) (2.44 g) and sodium bicarbonate (1.26 g) in water (50 ml) was stirred at 40° to 45° C. for 7 hours. The reaction mixture was adjusted to pH 6.0 with acetic acid. The solution was subjected to calcium chlomatography on macroporous non-ionic adsorption resin "Diaion HP-20" (60 ml) and eluted with water. The eluted solution (120 ml) was concentrated to a volume of 40 ml and the solution was acidified to pH 2.3 with 10% hydrochloric acid under ice-cooling. The precipitates were collected by filtration and dried to give 7-[2-(2-aminothiazol-4-yl)-2-(carboxymethoxyimino)acetamido]-3-methylthio-3-cephem-4-carboxylic acid (syn isomer) (1.6 g), mp. 183° to 186° C. (dec.).

IR (Nujol): 3300, 1760, 1665 cm$^{-1}$.

EXAMPLE 19

Trifluoroacetic acid (4.7 g) was added to a solution of pivaloyloxymethyl 7-[2-(2-aminothiazol-4-yl)-2-benzhydryloxycarbonylmethoxyiminoacetamido]-3-methylthio-3-cephem-4-carboxylate (syn isomer) (3.1 g) in dichloromethane (12.4 ml) and anisole (0.9 g) with ice-cooling and the mixture was stirred for an hour at ambient temperature. To the resulting solution was added isopropyl ether and stirred. The precipitates were collected by filtration, washed with isopropyl ether. The precipitates were added to a mixture of ethyl acetate and water and adjusted to pH 7.5 with saturated aqueous potassium carbonate. The separated aqueous layer was adjusted to pH 2.5 with 10% hydrochloric acid. The precipitates were filtrated off, washed with water and dried over phosphorus pentoxide in vacuo to give pivaloyloxymethyl 7-[2-(2-aminothiazol-4-yl)-2-carboxymethoxyiminoacetamido]-3-methylthio-3-cephem-4-carboxylate (syn isomer) (1.69 g).

IR (Nujol): 3300, 3200, 1770, 1750, 1670 cm$^{-1}$.

NMR (DMSO-d$_6$, δ): 1.15 (9H, s), 2.37 (3H, s), 3.82 (2H, s), 4.59 (2H, s), 5.17 (1H, d, J=4.0 Hz), 5.71 (1H, dd, J=4.0 Hz, 8.0 Hz), 5.78 (2H, s), 6.83 (1H, s), 9.45 (1H, d, J=8.0 Hz).

EXAMPLE 20

Trifluoroacetic acid (14 ml) was added to a stirred suspension of benzhydryl 7-[2-(t-butoxycarbonylmethoxyimino)-2-(4-thiazolyl)acetamido]-3-methylthio-3-cephem-4-carboxylate (syn isomer) (3.5 g) in dichloromethane (7 ml) and anisole (3.5 ml) at ambient temperature and the mixture was stirred for 1.5 hours at the same temperature. To the resulting solution was added isopropyl ether (50 ml) and n-hexane (30 ml) and stirred. The precipitates were collected by filtration, washed with solution of isopropyl ether and n-hexane (1:1). The precipitates were added to a mixture of ethyl acetate and water and adjusted to pH 7.0 with saturated aqueous potassium carbonate. The separated aqueous layer was adjusted to pH 4.0 with 10% hydrochloric acid and the solution was washed with ethyl acetate. The aqueous layer was adjusted to pH 1.8 with 10% hydrochloric acid under ice cooling. The precipitates were filtered off, washed with cold water and dried over phosphorus pentoxide in vacuo to give 7-[2-(carboxymethoxyimino)-2-(4-thiazolyl)acetamido]-3-methylthio-3-cephem-4-carboxylic acid (syn isomer) (1.03 g).

IR (Nujol): 1760, 1670 cm$^{-1}$.

NMR (DMSO-d$_6$, δ): 2.33 (3H, s), 3.75 (2H, s), 4.69 (2H, s), 5.17 (1H, d, J=4.0 Hz), 5.76 (1H, dd, J=4.0 Hz, 8.0 Hz), 7.99 (1H, d, J=2.0 Hz), 9.16 (1H, d, J=2.0 Hz), 9.65 (1H, d, J=8.0 Hz).

EXAMPLE 21

The solution of benzhydryl 7-[2-(2-aminothiazol-4-yl)-2-tert-butoxymethoxyiminoacetimido]-3-methylthio-3 3-cephem-4-carboxylate (syn isomer, 1.7 g) and anisole (1.7 ml) in trifluoroacetic acid (6.8 ml) was stirred for an hour at ambient temperature. The resultant solution was poured into diisopropyl ether (350 ml), and then the precipitates were collected by filtration and washed with diisopropyl ether. The precipitates were dissolved in water (15 ml). The aqueous solution was adjusted to pH 5.0 with 5% aqueous solution of sodium bicarbonate and was subjected to column chromatography on macroporus, nonionic adsorption resin "Diaion HP-20" [Trademark, manufactured by Mitsubishi Chemical Industries Ltd.]. The column was eluted with water. The eluate was concentrated under reduced pressure and was adjusted to pH 2.3 with conc. hydrochloric acid. The precipitates were collected by filtration and dried over phosphorus pentoxide to give 7-[2-(2-aminothiazol-4-yl)-2-carboxymethoxyiminoacetamido]-3-methylthio-3-cephem-4-carboxylic acid (syn isomer, 0.6 g). mp. 183°-186° C. (dec.).

IR (Nujol): 3300, 1760, 1665 cm$^{-1}$.

NMR (DMSO-d$_6$, δ): 2.33 (3H, s), 3.73 (2H, s), 4.63 (2H, s), 5.13 (1H, d, J=5 Hz), 5.67 (1H, dd, J=5 Hz, 8 Hz), 6.83 (1H, s), 9.41 (1H, d, J=8 Hz).

EXAMPLE 22

To a suspension of benzhydryl 7-[2-(5-amino-1,2,4-thiadiazol-3-yl)-2-tert-butoxycarbonylmethoxyiminoacetamido]-3-methylthio-3-cephem-4-carboxylate (syn isomer, 1.8 g) in anisole (1.8 ml) was added trifluoroacetic acid (9.0 ml). The reaction mixture was stirred for 105 minutes at ambient temperature. Then the resultant solution was poured into diisopropyl ether (300 ml) and the precipitates were collected by filtration and washed with diisopropyl ether.

The precipitates were dissolved into water (20 ml). The aqueous solution was adjusted to pH 5.0 with 5% aqueous solution of sodium bicarbonate and was subjected to column chromatography on macroporus non-ionic adsorption resin "Diaion HP-20" [Trademark, manufactured by Mitsubishi Chemical Industries Ltd.]. The column was eluted with water. The eluate was concentrated under reduced pressure and was adjusted to pH 1.3 with conc. hydrochloric acid. The precipitates were collected by filtration and dried over phosphorus pentoxide to give 7-[2-(5-amino-1,2,4-thiadiazol-3-yl)-2-carboxymethoxyiminoacetamido]-3-methylthio-3-cephem-4-carboxylic acid (syn isomer, 0.6 g), mp. 173° to 176° C. (dec.).

IR (Nujol): 3380, 3290, 1764, 1722, 1672, 1644 cm$^{-1}$.

NMR (DMSO-d$_6$, δ): 2.83 (3H, s), 3.77 (2H, m), 4.67 (2H. broad s), 5.15 (1H, d, J=5 Hz), 5.77 (1H, dd, J=5 Hz, 8 Hz), 9.52 (1H, d, J=8 Hz).

EXAMPLE 23

The solution of benzhydryl 7-[2-(2-amino-5-chlorothiazol-4-yl)-2-tert-butoxycarbonylmethoxyiminoacetamido]-3-ethylthio-3-cephem-4-carboxylate (syn isomer, 2.0 g) in anisole (2 ml) and trifluoroacetic acid (8 ml) was stirred for 90 minutes at ambient temperature. The resultant solution was poured into diisopropyl ether (300 ml), and then the precipitates were collected by filtration and washed with diisopropyl ether. The precipitates were dissolved in water. The aqueous solution was adjusted to pH 5.5 with 5% aqueous solution of sodium bicarbonate. The solution was subjected to column chromatography on macroporous, nonionic adsorption resin "Diaion HP-20" [trademark, manufactured by Mitsubishi Chemical Industries Ltd.]. The column was eluted with water. The eluate was concentrated under reduced pressure and the residue was adjusted to pH 2.3 with 10% hydrochloric acid.

The precipitates were collected by filtration and dried over phosphorus pentoxide to give 7-[2-(2-amino-5-chlorothiazol-4-yl)-2-carboxymethoxyiminoacetamido]-3-ethylthio-3-cephem-4-carboxylic acid (syn isomer, 0.82 g), mp. 193° to 195° C. (dec.).

IR (Nujol): 3400, 3200, 1775, 1691, 1657 cm$^{-1}$.

NMR (DMSO-d$_6$, δ): 1.18 (3H, t, J=7 Hz), 2.85 (2H, q, J=7 Hz), 3.71 (2H, broad s), 4.63 (2H, broad s), 5.17 (1H, d, J=5 Hz), 5.77 (1H, dd, J=5 Hz, 8 Hz), 9.43 (1H, d, J=8 Hz).

EXAMPLE 24

The solution of benzhydryl 7-[2-(6-aminopyridin-2-yl)-2-tert-butoxycarbonylmethoxyiminoacetamido]-3-ethylthio-3-cephem-4-carboxylate (syn isomer, 2.3 g) in trifluoroacetic acid (10 ml) and anisole (2 ml) was stirred for 2 hours at ambient temperature. The resultant solution was poured into diisopropyl ether (300 ml) and the precipitates were collected by filtration. The precipitates were dissolved in an aqueous solution of sodium bicarbonate (pH 7.5). The aqueous solution was washed with ethyl acetate and was adjusted to pH 2.3 with 10% hydrochloric acid. The precipitates were collected by filtration, washed with water and dried over phosphorus pentoxide under reduced pressure to give 7-[2-(6-aminopyridin-2-yl)-2-carboxymethoxyiminoacetamido]-3-ethylthio-3-cephem-4-carboxylic acid (syn isomer, 0.87 g), mp. 164° to 167° C. (dec.).

IR (Nujol): 3300, 3180, 1773 (shoulder), 1765, 1663 cm$^{-1}$.

NMR (DMSO-d$_6$, δ): 1.17 (3H, t, J=7 Hz), 2.83 (2H, q, J=7 Hz), 3.70 (2H, broad s), 4.63 (2H, broad s), 5.17 (1H, d, J=5 Hz), 5.75 (1H, dd, J=5 Hz, 8 Hz), 6.50 (1H, d, J=8 Hz), 6.80 (1H, d, J=7 Hz), 7.40 (1H, dd, J=8 Hz), 9.33 (1H, d, J=8 Hz).

EXAMPLE 25

The solution of benzhydryl 7-[2-phenyl-2-tertbutoxycarbonylmethoxyiminoacetamido]-3-ethylthio-3-cephem-4-carboxylate (syn isomer, 2.0 g) and anisole (2.0 ml) in trifluoroacetic acid (8 ml) was stirred for 90 minutes at ambient temperature. The resultant solution was evaporated under reduced pressure and the residual oil was dissolved in an aqueous solution of sodium bicarbonate. After the solution was washed with ethyl acetate, the solution was adjusted to pH 2.0 with 10% hydrochloric acid and extracted with ethyl acetate (100 ml). The extract was washed with a saturated aqueous solution of sodium chloride and dried over magnesium sulfate. The solvent was evaporated under reduced pressure to give 7-[2-phenyl-2-carboxymethoxyiminoacetamido]-3-ethylthio-3-cephem-4-carboxylic acid (syn isomer, 1.3 g), mp. 103° to 107° C. (dec.).

IR (Nujol): 3250, 1760 (broad), 1674 (broad) cm$^{-1}$.

NMR (DMSO-d$_6$, δ): 1.20 (3H, t, J=7 Hz), 2.86 (2H, q, J=7 Hz), 3.73 (2H, broad s), 4.71 (2H, broad s), 5.23 (1H, d, J=5 Hz), 5.78 (1H, dd, J=5 Hz, 8 Hz), 7.47 (5H, m), 9.67 (1H, d, J=8 Hz).

EXAMPLE 26

The following compounds were prepared according to the similar manners to those of Examples 18 to 25.

(1) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$

NMR (DMSO-d$_6$, δ): 2.3 (3H, s), 3.73 (2H, s), 4.75 (2H, s), 5.10 (1H, d, J=8 Hz), 5.63 (1H, dd, J=5, 8 Hz), 7.55 (1H, s), 9.43 (1H, d, J=8 Hz).

(2) 7-[2-(2-Methylaminothiazol-4-yl)-2-(carboxymethoxyimino)acetamido]-3-methylthio-3-cephem-4-carboxylic acid (syn isomer).

NMR (DMSO-d$_6$, δ): 2.33 (3H, s), 2.83 (3H, s), 3.77 (2H, s), 4.65 (2H, s), 5.17 (1H, d, J=5 Hz), 5.70 (1H, dd, J=5, 8 Hz), 6.90 (1H, s), 9.45 (1H, d, J=8 Hz).

(3) 7-[2-(Carboxymethoxyimino)-2-(4-thiazolyl)acetamido]-3-ethylthio-3-cephem-4-carboxylic acid (syn isomer).

IR (Nujol): 1760, 1670 cm$^-$.

NMR (DMSO-d$_6$, δ): 1.18 (3H, t, J=7.0 Hz), 2.85 (2H, q, J=7.0 Hz), 3.71 (2H, s), 4.68 (2H, s), 5.21 (1H, d, J=5.0 Hz), 5.77 (1H, dd, J=5.0 Hz, 8.0 Hz), 7.97 (1H, d, J=2.0 Hz), 9.14 (1H, d, J=2.0 Hz), 9.58 (1H, d, J=8.0 Hz).

(4) 7-[2-(Carboxymethoxyimino)-2-(1,2,5-thiadiazol-3-yl)acetamido]-3-methylthio-3-cephem-4-carboxylic acid (syn isomer).

IR (Nujol): 3250, 1775, 1680 cm$^{-1}$.

NMR (DMSO-d$_6$, δ): 2.3 (3H, s), 3.73 (2H, m), 4.85 (2H, s), 5.13 (1H, d, J=5 Hz), 5.63 (1H, dd, J=8 Hz, 5 Hz), 9.33 (1H, s), 9.47 (1H, d, J=8 Hz).

(5) 7-[2-Carboxymethoxyimino-2-(2-naphthyl)acetamido]-3-methylthio-3-cephem-4-carboxylic acid (syn isomer).

IR (Nujol): 3300, 1760, 1680, 1540 cm$^{-1}$.

NMR (DMSO-d$_6$, δ): 2.30 (3H, s), 3.80 (2H, s), 4.80 (2H, s), 5.25 (1H, d, J=5 Hz), 6.85 (1H, dd, J=5, 8 Hz), 7.5-8.20 (7H, m), 9.80 (1H, d, J=8 Hz).

(6) 7-[2-(2-aminothiazol-4-yl)-2-carboxymethoxyiminoacetamido]-3-ethylthio-3-cephem-4-carboxylic acid (syn isomer), mp. 215°-218° C. (dec.).

IR (Nujol): 3280, 1763, 1670 cm$^{-1}$.

NMR (DMSO-d$_6$, δ): 1.19 (3H, t, J=7 Hz), 2.83 (2H, q, J=7 Hz), 3.73 (2H, broad s), 4.62 (2H, broad s), 5.17 (1H, d, J=5 Hz), 5.67 (1H, dd, J=5 Hz, 8 Hz), 6.82 (1H, s), 9.46 (1H, d, J=8 Hz).

(7) 7-[2-(5-Amino-1,2,4-thiadiazol-3-yl)-2-carboxymethoxyiminoacetamido]-3-ethylthio-3-cephem-4-carboxylic acid (syn isomer), mp. 163° to 166° C. (dec.).

IR (Nujol): 3380, 3270, 1760, 1718, 1669, 1640 cm$^{-1}$.

NMR (DMSO-d$_6$, δ): 1.17 (3H, t, J=7 Hz), 2.84 (2H, q, J=7 Hz), 3.73 (2H, broad s), 4.68 (2H, broad s), 5.18 (1H, d, J=5 Hz), 5.77 (1H, dd, J=5 Hz, 8 Hz), 9.53 (1H, d, J=8 Hz).

(8) 7-[2-(5-Amino-1,2,4-thiadiazol-3-yl)-2-(1-carboxyethoxyimino)acetamido]-3-ethylthio-3-cephem-4-carboxylic acid (syn isomer).

IR (Nujol): 3300, 3180, 1760, 1670, 1620 cm$^{-1}$.

NMR (DMSO-d$_6$, δ): 1.18 (3H, t, J=7.0 Hz), 1.36, 1.46 (3H, d, J=7.0 Hz), 2.86 (2H, q, J=7.0 Hz), 3.75 (2H, m), 4.71 (1H, m), 5.21 (1H, d, J=5.0 Hz), 5.81 (1H, dd, J=5.0 Hz, 8.0 Hz), 8.20 (2H, broad s), 9.47 and 9.54 (each ½H, d, J=8.0 Hz).

(9) 7-[2-(2-Aminothiazol-4-yl)-2-carboxymethoxyiminoacetamido]-3-propylthio-3-cephem-4-carboxylic acid (syn isomer), mp. 125° to 128° C. (dec.).

IR (Nujol): 3300, 1760 (broad), 1665 (broad) cm$^{-1}$.

NMR (DMSO-d$_6$, δ): 0.95 (3H, t, J=7 Hz), 1.50 (2H, sextet, J=7 Hz), 2.83 (2H, t, J=7 Hz), 3.72 (2H, broad s), 4.62 (2H, broad s), 5.22 (1H, d, J=5 Hz), 5.73 (1H, dd, J=5 Hz, 8 Hz), 6.85 (1H, s), 9.50 (1H, d, J=8 Hz).

(10) 7-[2-(2-Aminothiazol-4-yl)-2-(1-carboxyethoxyimino)acetamido]-3-ethylthio-3-cephem-4-carboxylic acid (syn isomer).

IR (Nujol): 3280, 3180, 1760, 1670, 1630 cm$^{-1}$.

NMR (DMSO-d$_6$, δ): 1.18 (3H, t, J=7.0 Hz), 1.43 (3H, d, J=7.0 Hz), 2.86 (2H, q, J=7.0 Hz), 3.75 (2H, broad s), 4.67 (1H, m), 5.23 (1H, d, J=5.0 Hz), 5.78 (1H, m), 6.84 (1H, s), 9.47 (1H, d, J=8.0 Hz).

(11) 7-[2-(2-Aminothiazol-4-yl)-2-(1-carboxyethoxyimino)acetamido]-3-methylthio-3-cephem-4-carboxylic acid (syn isomer), mp. 110° to 115° C. (dec.).

IR (Nujol): 3300, 1760, 1670, 1530 cm$^{-1}$.

NMR (DMSO-d$_6$, δ): 1.40 (3H, d, J=6 Hz), 2.30 (3H, s), 3.73 (2H, s), 4.60 (1H, q, J=6 Hz), 5.13 (1H, d, J=5 Hz), 5.72 (1H, dd, J=5 Hz, 8 Hz), 6.77 (1H, s), 7.18 (2H, broad s), 9.38 (1H, d, J=8 Hz).

(12) 7-[2-(2-Amino-5-chlorothiazol-4-yl)-2-carboxymethoxyiminoacetamido]-3-methylthio-3-cephem-4-carboxylic acid (syn isomer), mp. 178° C. (dec.).

IR (Nujol): 3400, 3200, 1770, 1690, 1655, 1620, 1530 cm$^{-1}$.

NMR (DMSO-d$_6$, δ): 2.34 (3H, s), 3.05 (2H, s), 4.63 (2H, s), 5.12 (1H, d, J=5 Hz), 5.70 (1H, dd, J=5 Hz, 8 Hz), 7.35 (2H, broad s), 9.40 (1H, d, J=8 Hz).

(13) 7-[2-(6-aminopyridin-2-yl)-2-carboxymethoxyiminoacetamido]-3-methylthio-3-cephem-4-carboxylic acid (syn isomer), mp. 111° to 116° C. (dec.).

IR (Nujol): 3300, 3150, 1760, 1660 (broad), 1618 cm$^{-1}$.

NMR (DMSO-d$_6$, δ): 2.34 (3H, s), 3.78 (2H, broad s), 4.75 (2H, broad s), 5.18 (1H, d, J=5 Hz), 5.77 (1H, dd, J=5 Hz, 8 Hz), 6.72 (1H, d, J=8 Hz), 6.90 (1H, d, J=7 Hz), 7.60 (1H, dd, J=7 Hz, 8 Hz), 9.57 (1H, d, J=8 Hz).

(14) 7-[2-(2-Furyl-2-carboxymethoxyiminoacetamido]-3-methylthio-3-cephem-4-carboxylic acid (syn isomer).

IR (Nujol): 3200, 1760, 1670, 1530 cm$^{-1}$.

NMR (DMSO-d$_6$, δ): 2.37 (3H, s), 3.78 (2H, s), 4.68 (2H, s), 5.22 (1H, d, J=5 Hz), 5.77 (1H, dd, J=5 Hz, 8 Hz), 6.83 (2H, m), 7.88 (1H, broad s), 9.73 (1H, d, J=8 Hz).

(15) 7-[2-carboxymethoxyimino-2-(1,2,4-thiadiazol-3-yl)-acetamido]-3-methylthio-3-cephem-4-carboxylic acid (syn isomer).

IR (Nujol): 1760, 1700, 1660 cm$^{-1}$.

NMR (DMSO-d$_6$, δ): 2.31 (3H, S), 3.75 (2H, S), 4.74 (2H, S), 5.14 (1H, d, J=5.0 HZ), 5.77 (1H, d-d, J=5.0 HZ, 8.0 HZ), 10.23 (1H, S), 9.61 (1H, d, J=8.0 HZ).

EXAMPLE 27

To a suspension of benzhydryl 7-[2-(2-aminothiazol-4-yl)-2-(methoxycarbonylmethoxyimino)acetamido]-3-methylthio-3-cephem-4-carboxylate (syn isomer) (11.6 g) and anisole (8.5 g) in dichloromethane (30 ml) was added trifluoroacetic acid (36.5 g) under ice-cooling and the mixture was stirred at ambient temperature for 2 hours. The reaction mixture was dropwise added to isopropyl ether (200 ml) under stirring and the precipitates were collected by filtration. The precipitates were dissolved in ethyl acetate and saturated sodium bicarbonate solution and aqueous layer was separated. The aqueous layer was adjusted to pH 4.5 with 10% hydrochloric acid. After removing the solvent in reduced pressure, the solution was acidified to pH 2.5 with 10% hydrochloric acid under ice-cooling. The precipitates were filtered and dried to give 7-[2-(2-aminothiazol-4-yl)-2-(methoxycarbonylmethoxyimino)acetamido]-3-methylthio-3-cephem-4-carboxylic acid (syn isomer) (6.1 g).

IR (Nujol): 3250, 1765, 1720, 1650 cm$^{-1}$.

NMR (DMSO-d$_6$, δ): 2.35 (3H, s), 3.70 (3H, s), 3.76 (2H, s), 4.73 (2H, s), 5.16 (1H, d, J=5 Hz), 5.68 (1H, dd, J=5, 8 Hz), 6.90 (1H, s), 9.56 (1H, d, J=8 Hz).

EXAMPLE 28

The following compounds were prepared according to a similar manner to that of Example 27.

(1) 7-[2-(2-Aminothiazol-4-yl)-2-(carboxymethoxyimino)acetamido]-3-methylthio-3-cephem-4-carboxylic acid (syn isomer), mp. 183° to 186° C. (dec.).

IR (Nujol): 3300, 1760, 1665 cm$^{-1}$.

(2) 7-[2-Benzhydryloxycarbonylmethoxyimino-2-(2-formamidothiazol-4-yl)acetamido]-3-methylthio-3-cephem-4-carboxylic acid (syn isomer).

IR (Nujol): 3270, 1770, 1740, 1650 (broad) cm$^{-1}$.

(3) Sodium 7-[2-(2-aminothiazol-4-yl)-2-benzhydryloxycarbonylmethoxyiminoacetamido]-3-methylthio-3-cephem-4-carboxylate (syn isomer).

IR (Nujol): 1730 (broad), 1670 cm$^{-1}$.

(4) 7-[2-(2-Aminothiazol-4-yl)-2-(carboxymethoxyimino)acetamido]-3-methylthio-3-cephem-4-carboxylic acid (anti isomer).

IR (Nujol): 3280, 3110, 1770, 1660 cm$^{-1}$.

(5) 7-[2-(2-Methylaminothiazol-4-yl)-2-(methoxycarbonylmethoxyimino)acetamido]-3-methylthio-3-cephem-4-carboxylic acid (syn isomer).

IR (Nujol): 3250, 1785, 1755, 1645 cm$^{-1}$ (6) 7-[2-(2-Methylaminothiazol-4-yl)-2-(carboxymethoxyimino)acetamido]-3-methylthio-3-cephem-4-carboxylic acid (syn isomer).

NMR (DMSO-d$_6$, δ): 2.33 (3H, s), 2.83 (3H, s), 3.77 (2H, s), 4.65 (2H, s), 5.17 (1H, d, J=5 Hz), 5.70 (1H, dd, J=5, 8 Hz), 6.90 (1H, s), 9.45 (1H, d, J=8 Hz).

(7) 7-[2-(Carboxymethoxyimino)-2-(4-thiazolyl)acetamido]-3-methylthio-3-cephem-4-carboxylic acid (syn isomer).

IR (Nujol): 1760, 1670 cm$^{-1}$.

(8) 7-[2-(Carboxymethoxyimino)-2-(4-thiazolyl)acetamido]-3-ethylthio-3-cephem-4-carboxylic acid (syn isomer).

IR (Nujol): 1760, 1670 cm$^{-1}$.

(9) 7-[2-(Carboxymethoxyimino)-2-(1,2,5-thiadiazol-3-yl)acetamido]-3-methylthio-3-cephem-4-carboxylic acid (syn isomer).

IR (Nujol): 3250, 1775, 1680 cm$^{-1}$.

(10) 7-[2-Carboxymethoxyimino-2-(2-naphthyl)acetamido]-3-methylthio-3-cephem-4-carboxylic acid (syn isomer).

IR (Nujol): 3300, 1760, 1680, 1540 cm$^{-1}$.

(11) 7-[2-(2-aminothiazol-4-yl)-2-carboxymethoxyiminoacetamido]-3-methylthio-3-cephem-4-carboxylic acid (syn isomer). mp. 183°–186° C. (dec.).

IR (Nujol): 3300, 1760, 1665 cm$^{-1}$.

(12) 7-[2-(2-aminothiazol-4-yl)-2-carboxymethoxyiminoacetamido]-3-ethylthio-3-cephem-4-carboxylic acid (syn isomer), mp. 215°–218° C. (dec.).

IR (Nujol): 3280, 1763, 1670 cm$^{-1}$.

(13) 7-[2-(5-amino-1,2,4-thiadiazol-3-yl)-2-carboxymethoxyiminoacetamido]-3-methylthio-3-cephem-4-carboxylic acid (syn isomer,), mp. 173° to 176° C. (dec.).

IR (Nujol): 3380, 3290, 1764, 1722, 1672, 1644 cm$^{-1}$.

(14) 7-[2-(2-amino-5-chlorothiazol-4-yl)-2-carboxymethoxyiminoacetamido]-3-ethylthio-3-cephem-4-carboxylic acid (syn isomer,), mp. 193° to 195° C. (dec.).

IR (Nujol): 3400, 3200, 1775, 1691, 1657 cm$^{-1}$.

(15) 7-[2-(6-aminopyridin-2-yl)-2-carboxymethoxyiminoacetamido]-3-ethylthio-3-cephem-4-carboxylic acid (syn isomer,), mp. 164° to 167° C. (dec.).

IR (Nujol): 3300, 3180, 1773 (shoulder), 1765, 1663 cm$^{-1}$.

(16) 7-[2-phenyl-2-carboxymethoxyiminoacetamido]-3-ethylthio-3-cephem-4-carboxylic acid (syn isomer,), mp. 103° to 107° C. (dec.).

IR (Nujol): 3250, 1760 (broad), 1674 (broad) cm$^{-1}$.

(17) 7-[2-(5-Amino-1,2,4-thiadiazol-3-yl)-2-carboxymethoxyiminoacetamido]-3-ethylthio-3-cephem-4-carboxylic acid (syn isomer), mp. 163° to 166° C. (dec.).

IR (Nujol): 3380, 3270, 1760, 1718, 1669, 1640 cm$^{-1}$.

(18) 7-[2-(5-Amino-1,2,4-thiadiazol-3-yl)-2-(1-carboxyethoxyimino)acetamido]-3-ethylthio-3-cephem-4-carboxylic acid (syn isomer).

IR (Nujol): 3300, 3180, 1760, 1670, 1620 cm$^{-1}$.

(19) 7-[2-(2-Aminothiazol-4-yl)-2-carboxymethoxyiminoacetamido]-3-propylthio-3-cephem-4-carboxylic acid (syn isomer), mp. 125° to 128° C. (dec.).

IR (Nujol): 3300, 1760 (broad), 1665 (broad) cm$^{-1}$.

(20) 7-[2-(2-Aminothiazol-4-yl)-2-(1-carboxyethoxyimino)acetamido]-3-ethylthio-3-cephem-4-carboxylic acid (syn isomer).

IR (Nujol): 3280, 3180, 1760, 1670, 1630 cm$^{-1}$.

(21) 7-[2-(2-Aminothiazol-4-yl)-2-(1-carboxyethoxyimino)acetamido]-3-methylthio-3-cephem-4-carboxylic acid (syn isomer), mp. 110° to 115° C. (dec.).

IR (Nujol): 3300, 1760, 1670, 1530 cm$^{-1}$.

(22) 7-[2-(2-Amino-5-chlorothiazol-4-yl)-2-(carboxymethoxyiminoacetamido]-3-methylthio-3-cephem-4-carboxylic acid (syn isomer), mp. 178° C. (dec.).

IR (Nujol): 3400, 3200, 1770, 1690, 1655, 1620, 1530 cm$^{-1}$.

(23) 7-[2-(6-aminopyridin-2-yl)-2-carboxymethoxyiminoacetamido]-3-methylthio-3-cephem-4-carboxylic acid (syn isomer), mp. 111° to 116° C. (dec.).

IR (Nujol): 3300, 3150, 1760, 1660 (broad), 1618 cm$^{-1}$.

(24) 7-[2-(2-Furyl-2-carboxymethoxyiminoacetamido]-3-methylthio-3-cephem-4-carboxylic acid (syn isomer).

IR (Nujol): 3200, 1760, 1670, 1530 cm$^{-1}$.

(25) 7-[2-carboxymethoxyimino-2-(1,2,4-thiadiazol-3-yl)-acetamido]-3-methylthio-3-cephem-4-carboxylic acid (syn isomer).

IR (Nujol): 1760, 1700, 1660 cm$^{-1}$.

EXAMPLE 29

To a solution of sodium 7-[2-(2-aminothiazol-4-yl)-2-benzhydryloxycarbonylmethoxyiminoacetamido]-3-methylthio-3-cephem-4-carboxylate (syn isomer) (4.0 g) in dimethylformamide (40 ml) was added a solution of pivaloyloxymethyl iodide (1.5 g) in dimethylformamide (4.5 ml) at 0° C. and the mixture was stirred for 15 minutes at the same temperature. Ethyl acetate (150 ml) and water (100 ml) were added to the reaction mixture. The separated organic layer was washed with saturated aqueous sodium bicarbonate and water, dried over magnesium sulfate and evaporated to give pivaloyloxymethyl 7-[2-(2-aminothiazol-4-yl)-2-benzhydryloxycarbonylmethoxyiminoacetamido]-3-methylthio-3-cephem-4-carboxylate (syn isomer) (3.22 g).

IR (Nujol): 3280, 3180, 1740 (broad), 1670, 1620 cm$^{-1}$.

NMR (DMSO-d$_6$, δ): 1.14 (9H, s), 2.36 (3H, s), 3.79 (2H, s), 4.84 (2H, s), 5.17 (1H, d, J=5.0 Hz), 5.73 (1H, dd, J=5.0 Hz, 8.0 Hz), 5.86 (2H, s), 6.83 (1H, s), 6.87 (1H, s), 7.17–7.58 (10H, m), 9.57 (1H, d, J=8.0 Hz).

EXAMPLE 30

The following compounds were prepared according to a similar manner to that of Example 29.

(1) Benzhydryl 7-[2-(2-formamidothiazol-4-yl)-2-tert-butoxycarbonylmethoxyiminoacetamido]-3-methylthio-3-cephem-4-carboxylate (syn isomer), mp. 151° to 157° C.

IR (Nujol): 3250, 1780, 1690 cm$^{-1}$.

(2) Benzhydryl 7-[2-(2-aminothiazol-4-yl)-2-(methoxycarbonylmethoxyimino)acetamido]-3-methylthio-3-cephem-4-carboxylate (syn isomer).

IR (Nujol): 1770, 1670, 1610 cm$^{-1}$.

(3) Pivaloyloxymethyl 7-[2-(2-aminothiazol-4-yl)-2-carboxymethoxyiminoacetamido]-3-methylthio-3-cephem-4-carboxylate (syn isomer).

IR (Nujol): 3300, 3200, 1770, 1750, 1670 cm$^{-1}$.

(4) Benzhydryl 7-[2-(2-formamidothiazol-4-yl)-2-(tert-butoxycarbonylmethoxyimino)acetamido]-3-methylthio-3-cephem-4-carboxylate (anti isomer).

IR (Nujol): 3250, 1760 (broad, 1685 cm$^{-1}$.

(5) Benzhydryl 7-[2-(2-aminothiazol-4-yl)-2-(tert-butoxycarbonylmethoxyimino)acetamido]-3-methylthio-3-cephem-4-carboxylate (anti isomer).

IR (Nujol): 3300, 1760, 1685, 1610 cm$^{-1}$.

(6) Benzhydryl 7-[2-(t-butoxycarbonylmethoxyimino)-2-(4-thiazolyl)acetamido]-3-methylthio-3-cephem-4-carboxylate (syn isomer).

IR (Nujol): 3270, 1780, 1720, 1655.

(7) Benzhydryl 7-[2-(t-butoxycarbonylmethoxyimino)-2-(4-thiazolyl)acetamido]-3-ethylthio-3-cephem-4-carboxylate (syn isomer).

IR (Nujol): 3270, 1765, 1750, 1695, 1680, 1650 cm$^{-1}$.

(8) Benzhydryl 7-[2-(tert-butoxycarbonylmethoxyimino)-2-(1,2,5-thiadiazol-3-yl)acetamido]-3-methylthio-3-cephem-4-carboxylate (syn isomer).

IR (Nujol): 3250, 1765, 1730, 1680 cm$^{-1}$.

(9) Benzhydryl 7-[2-(tert-butoxycarbonylmethoxyimino)-2-(2-naphthyl)acetamido]-3-methylthio-3-cephem-4-carboxylate (syn isomer).

IR (Nujol): 3300, 1770, 1720, 1680, 1540 cm$^{-1}$.

(10) Benzhydryl 7-[2-(2-formamidothiazol-4-yl)-2-tert-butoxycarbonylmethoxyiminoacetamido]-3-methylthio-3-cephem-4-carboxylate (syn isomer). mp. 151°–157° C.

IR (Nujol): 3250, 1780, 1690 cm$^{-1}$.

(11) Benzhydryl 7-[2-(2-aminothiazol-4-yl)-2-tert-butoxycarbonylmethoxyiminoacetamido]-3-methylthio-3-cephem-4-carboxylate (syn isomer). mp. 148°–155° C.

IR (Nujol): 3300, 1778, 1685 cm$^{-1}$.

(12) Benzhydryl 7-[2-(2-formamidothiazol-4-yl)-2-tert-butoxycarbonylmethoxyiminoacetamido]-3- ethylthio-3-cephem-4-carboxylate (syn isomer). mp 173°–176° C.

IR (Nujol): 3250, 1780, 1745, 1726, 1690 cm$^{-1}$.

(13) Benzhydryl 7-[2-(2-aminothiazol-4-yl)-2-tert-butoxycarbonylmethoxyiminoacetamido]-3-ethylthio-3-cephem-4-carboxylate (syn isomer). mp 165°–169° C.

IR (Nujol): 3250, 1780, 1728, 1685 cm$^{-1}$.

(14) Benzhydryl 7-[2-(5-amino-1,2,4-thiadiazol-3-yl)-2-tert-butoxycarbonylmethoxyiminoacetamido]-3-methylthio-3-cephem-4-carboxylate (syn isomer), mp. 123°–129° C. (dec.).

IR (Nujol): 3300, 1776, 1689, 1615 cm$^{-1}$.

(15) Benzhydryl 7-[2-(2-formamido-5-chlorothiazol-4-yl)-2-tert-butoxycarbonylmethoxyiminoacetamido]-3-ethylthio-3-cephem-4-carboxylate (syn isomer), mp. 143° to 148° C.

IR (Nujol): 3250, 1780, 1750, 1728, 1683 cm$^{-1}$.

(16) Benzhydryl-7-[2-(6-formamidopyridin-2-yl)-2-tert-butoxycarbonylmethoxyiminoacetamido]-3-ethylthio-3-cephem-4-carboxylate (syn isomer), mp. 113° to 123° C.

IR (Nujol): 3250, 1774 (broad), 1688 (broad) cm$^{-1}$.

(17) Benzhydryl 7-[2-(5-amino-1,2,4-thiadiazol-3-yl)-2-tert-butoxycarbonylmethoxyiminoacetamido]-3-ethylthio-3-cephem-4-carboxylate (syn isomer), mp. 103° to 108° C. (dec.).

IR (Nujol): 3300, 1775, 1727, 1690, 1620 cm$^{-1}$.

(18) Benzhydryl 7-[2-(5-amino-1,2,4-thiadiazol-3-yl)-2-(1-tert-butoxycarbonylethoxyimino)acetamido]-3-ethylthio-3-cephem-4-carboxylate (syn isomer).

IR (Nujol): 1770, 1720, 1685, 1610 cm$^{-1}$.

(19) Benzhydryl 7-[2-phenyl-2-tert-butoxycarbonylmethoxyiminoacetamido]-3-ethylthio-3-cephem-4-carboxylate (syn isomer), mp. 98° to 103° C.

IR (Nujol): 3280, 1779, 1723, 1710, 1674 cm$^{-1}$.

(20) Benzhydryl 7-[2-(2-formamidothiazol-4-yl)-2-tert-butoxycarbonylmethoxyiminoacetamido]-3-propylthio-3-cephem-4-carboxylate (syn isomer).

IR (Nujol): 3240, 3130, 1780, 1722, 1684 cm$^{-1}$.

(21) Benzhydryl 7-[2-(2-formamidothiazol-4-yl)-2-(1-tert-butoxycarbonylethoxyimino)acetamido]-3-methylthio-3-cephem-4-carboxylate (syn isomer).

IR (Nujol): 3200, 1780, 1680 (broad), 1540 cm$^{-1}$.

(22) Benzhydryl 7-[2-(2-formamido-5-chlorothiazol-4-yl)-2-tert-butoxycarbonylmethoxyaminoacetamido]-3-methylthio-3-cephem-4-carboxylate (syn isomer).

IR (Nujol): 3200, 1780, 1750, 1725, 1690, 1540 cm$^{-1}$.

(23) Benzhydryl 7-[2-(2-formamidothiazol-4-yl)-2-(1-tert-butoxycarbonylethoxyimino)acetamido]-3-ethylthio-3-cephem-4-carboxylate (syn isomer).

IR (Nujol): 3150, 1780, 1715, 1680 cm$^{-1}$.

(24) Benzhydryl 7-[2-(6-formamidopyridin-2-yl)-2-tert-butoxycarbonylmethoxyiminoacetamido]-3-methylthio-3-cephem-4-carboxylate (syn isomer), mp. 109° to 110° C. (dec.).

IR (Nujol): 3250, 1775, 1750 (shoulder), 1690 (broad) cm$^{-1}$.

(25) Benzhydryl 7-[2-(2-furyl)-2-tert-butoxycarbonylmethoxyiminoacetamido]-3-methylthio-3-cephem-4-carboxylate (syn isomer).

IR (Nujol): 3250, 1780, 1725, 1685, 1540 cm$^{-1}$.

(26) Benzhydryl 7-[2-(2-amino-5-chlorothiazol-4-yl)-2-tert-butoxycarbonylmethoxyiminoacetamido]-3-ethylthio-3-cephem-4-carboxylate (syn isomer,), mp. 171° to 176° C.

IR (Nujol): 3300, 1770 (broad), 1724, 1688 cm$^{-1}$.

(27) Benzhydryl 7-[2-(6-aminopyridin-2-yl)-2-tert-butoxycarbonylmethoxyiminoacetamido]-3-ethylthio-3-cephem-4-carboxylate (syn isomer,), mp. 121° to 128° C. (dec.).

IR (Nujol): 3350, 1774, 1728, 1684 cm$^{-1}$.

(28) Benzhydryl 7-[2-(2-aminothiazol-4-yl)-2-(1-tert-butoxycarbonylethoxyimino)acetamido]-3-methylthio-3-cephem-4-carboxylate (syn isomer).

IR (Nujol): 3250, 1780, 1720, 1680, 1620, 1540 cm$^{-1}$.

(29) Benzhydryl 7-[2-(2-amino-5-chlorothiazol-4-yl)-2-tert-butoxycarbonylmethoxyiminoacetamido]-3-methylthio-3-cephem-4-carboxylate (syn isomer).

IR (Nujol): 3300, 1770, 1730, 1690, 1620, 1540 cm$^{-1}$.

(30) Benzhydryl 7-[2-(2-aminothiazol-4-yl)-2-(1-tert-butoxycarbonylethoxyimino)acetamido]-3-ethylthio-3-cephem-4-carboxylate (syn isomer).

IR (Nujol): 1775, 1710, 1680, 1610 cm$^{-1}$.

(31) Benzhydryl 7-[2-(2-aminothiazol-4-yl)-2-tert-butoxycarbonylmethoxyiminoacetamido]-3-propylthio-3-cephem-4-carboxylate (syn isomer).

IR (Nujol): 3260, 1778, 1723, 1680 cm$^{-1}$.

(32) Benzhydryl 7-[2-(6-aminopyridin-2-yl)-2-tert-butoxycarbonylmethoxyiminoacetamido]-3-methylthio-3-cephem-4-carboxylate (syn isomer). mp. 97° to 101° C. (dec.).

IR (Nujol): 3300, 1777 (broad), 1688, 1616 cm$^{-1}$.

(33) Benzhydryl 7-[2-(t-butoxycarbonylmethoxyimino)-2-(1,2,4-thiadiazol-3-yl)acetamido]-3-methyethio-3-cephem-4-carboxylate (syn isomer).

IR (Nujol): 1760(broad), 1680, 1630 cm$^{-1}$.

EXAMPLE 31

1-Ethoxycarbonyloxyethyl chloride (3.66 g) was added to a mixture of 7-[2-(2-aminothiazol-4-yl)-2-carboxymethoxyiminoacetamido]-3-methylthio-3-cephem-4-carboxylic acid (syn isomer) (4.7 g) and Potassium carbonate (1.66 g) in dimethylsulfoxide (40 ml) and stirred at 40° C. for 4.5 hours. The reaction mixture was added to the stirred mixture of water (200 ml) and ethyl acetate (200 ml).

The separated organic layer was washed with 5% aqueous sodium bicarbonate and water, and dried over magnesium sulfate and evaporated to give crude product (2.4 g).

The crude product was subjected to column chromatography on silicagel. The column was eluted with a mixture of ethyl acetate and N-hexane (2:1) to give 1-ethoxycarbonyloxyethyl 7-[2-(2-aminothiazol-4-yl)-2-(1-ethoxycarbonyloxyethyl)oxycarbonylmethoxyiminoacetamido]-3-methylthio-3-cephem-4-carboxylate (syn isomer) (0.92 g).

IR [Nujol]: 3300, 1760, 1680, 1620, 1535 cm$^{-1}$.

NMR [DMSO-d$_6$, $\delta$]: 1.22 (6H, t, J=7 HZ), 1.47 (6H, d, J=5 HZ), 2.40 (3H, S), 3.83 (2H, broad S), 4.17 (4H, q, J=7 HZ), 4.73 (2H, S), 5.18 (1H, d, J=5 HZ), 5.75 (1H, m), 6.78 (2H, m), 6.85 (1H, S), 7.23 (2H, broad S), 9.55 (1H, J=8 HZ).

EXAMPLE 32

To a suspension of 7-[2-(2-aminothiazol-4-yl)-2-carboxymethoxyiminoacetamido]-3-methylthio-3-cephem-4-carboxylic acid (syn isomer) (10 g) in water (80 ml) was added dropwise conc. hydrochloric acid (10 ml) at room temperature under stirring and the mixture was stirred at the same temperature for one hour. The precipitates were filtered and washed with cold water and dried to give 7-[2-(2-aminothiazol-4-yl)-2-carboxymethoxyiminoacetamido]-3-methylthio-3-cephem-4-carboxylic acid hydrochloride (syn isomer) (9.5 g).

IR [Nujol]: 3250, 1750, 1690, 1660, 1620, 1590, 1560, cm$^{-1}$.

EXAMPLE 33

The following compounds were prepared according to the similar manners to those of the above Examples.

(1) 1-Propionyloxyethyl 7-[2-(2-aminothiazol-4-yl)-2-benzhydryloxycarbonylmethoxyiminoacetamido]-3-methylthio-3-cephem-4-carboxylate (syn isomer).

IR (Nujol): 1750 (br.), 1675, 1610 cm$^{-1}$.

NMR (DMSO-d6, δ): 1.03 (3H, t, J=7.0 Hz), 1.46 (3H, d, J=5.0 Hz), 2.36 (2H, q, J=7.0 Hz), 2.39 (3H, s), 3.82 (2H, s), 4.87 (2H, s), 5.19 (1H, d, J=4.0 Hz), 5.76 (1H, m), 6.83-7.16 (1H, m), 6.87 (1H, s), 6.91 (1H, s), 7.17-7.56 (10H, m), 9.59 (1H, d, J=8.0 Hz).

(2) 1-Ethoxycarbonyloxyethyl 7-[2-(2-aminothiazol-4-yl)-2-benzhydryloxycarbonylmethoxyiminoacetamido]-3-methylthio-3-cephem-4-carboxylate (syn isomer).

IR (Nujol): 1750 (br.), 1670, 1615 cm$^{-1}$.

NMR (DMSO-d6, δ): 1.25 (3H, t, J=7.0 Hz), 1.48 (3H, d. J=5.0 Hz), 2.38 (3H, s), 3.82 (2H, s), 4.17 (2H, q, J=7.0 Hz), 4.86 (2H, s), 5.19 (1H, d, J=4.0 Hz), 5.73 (1H, d-d, J=4.0 Hz 8.0 Hz), 6.80 (1H, m), 6.86 (1H, s), 6.90 (1H, s), 7.17-7.55 (10H, m), 9.60 (1H, d, J=8,0 Hz).

(3) 1-Propionyloxyethyl 7-[2-(2-aminothiazol-4-yl)-2-methoxycarbonylmethoxyiminoacetamido]-3-methylthio-3-cephem-4-carboxylate (syn isomer).

IR (Nujol): 1750, 1570, 1610, 1530 cm$^{-1}$.

NMR (DMSO-d6, δ): 1.03 (3H, t, J=7 Hz), 1.47 (3H, d, J=6 Hz), 2.28 (2H, q, J=7 Hz), 2.40 (3H, s), 3.68 (3H, s), 3.83 (2H, s), 4.70 (2H, s), 5.18 (1H, d, J=5 Hz), 5.73 (1H, m), 6.68 (1H, s), 6.92 (1H, m), 7.22 (2H, br., s), 9.52 (1H, d, J=8 Hz).

(4) 1-Propionyloxyethyl 7-[2-(2-aminothiazol-4-yl)-2-(1-propionyloxyethyl)oxycarbonylmethoxyiminoacetamido]-3-methylthio-3-cephem-4-carboxylate (syn isomer).

IR (Nujol): 3250, 1755, 1680, 1620, 1535 cm$^{-1}$.

NMR (DMSO-d6, δ): 1.03 (6H, t, J=7 Hz), 1.47 (6H, d, J=5 Hz), 2.35 (2H, q, J=7 Hz), 2.40 (3H, s), 3.85 (2H, br., s), 4.73 (2H, br., s), 5.20 (1H, d, J=5 Hz), 5.75 (1H, dd, J=5 Hz, 8 Hz), 6.82 (1H, m), 6.87 (1H, s), 7.25 (2H, br., s), 9.57 (1H, d, J=8 Hz).

(5) 7-[2-(2-Formamido-5-chlorothiazol-4-yl)-2-benzhydryloxycarbonylmethoxyiminoacetamido]-3-methylthio-3-cephem-4-carboxylic acid (syn isomer).

IR (Nujol): 1780, 1740, 1670 cm$^{-1}$.

NMR (DMSO-d6, δ): 2.33 (3H, s), 3.74 (2H, s), 4.95 (2H, s), 5.16 (1H, d, J=4.0 Hz), 5.81 (1H, dd, J=4.0 Hz, 8.0 Hz), 6.93 (1H, s), 7.20-7.62 (10H, m), 8.56 (1H, s), 9.64 (1H, d, J=8.0 Hz), 12.89 (1H, br., s).

(6) 7-[2-(2-Amino-5-chlorothiazol-4-yl)-2-benzhydryloxycarbonylmethoxyiminoacetamido]-3-methylthio-3-cephem-4-carboxylic acid (syn isomer).

IR (Nujol): 1740 (br.), 1660 cm$^{-1}$.

NMR (DMSO-d6, δ): 2.33 (3H, s), 3.73 (2H, s), 4.89 (2H, s), 5.16 (1H, d, J=4.0 Hz), 5.79 (1H, dd, J-4.0 Hz, 8.0 Hz), 6.95 (1H, s), 7.23∼7.61 (10H, m), 9.59 (1H, d, J=8.0 Hz).

(7) 1-Ethoxycarbonyloxyethyl 7-[2-(2-amino-5-chlorothiazol-4-yl)-2-benzhydryloxycarbonylmethoxyiminoacetamido]-3-methylthio-3-cephem-4-carboxylate (syn isomer).

IR (Nujol): 1750 (br.), 1670, 1620 cm$^{-1}$.

NMR (DMSO-d6, δ): 1.22 (3H, t, J=7.0 Hz), 1.48 (3H, d, 5.0 Hz), 2.38 (3H, s), 3.82 (2H, s), 4.17 (2H, q, J=7.0 Hz), 4.88 (2H, s), 5.16 (1H, d, J=4.0 Hz), 5.78 (1H, dd, J=4.0 Hz, 8.0 Hz), 6.79 (1H, m), 6.92 (1H, s), 7.21-7.55 (10H, m), 9.53 (1H, d, J=8.0 Hz).

(8) (5-Methyl-2-oxo-1,3-dioxol-4-yl)methyl 7-[2-(2-aminothiazol-4-yl)-2-benzhydryloxycarbonylmethoxyiminoacetamido]-3-methylthio-3-cephem-4-carboxylate (syn isomer).

IR (Nujol): 1815, 1770, 1730, 1675, 1615 cm$^{-1}$.

NMR (DMSO-d6, δ): 2.18 (3H, s), 2.38 (3H, s), 3.80 (2H, s), 4.86 (2H, s), 5.15 (2H, s), 5.21 (1H, d, J=4.0 Hz), 5.76 (1H, d-d, J=4.0 Hz and 8.0 Hz), 6.85 (1H, s), 6.91 (1H, s), 7.13-7.51 (10H, m), 9.60 (1H, d, J=8.0 Hz).

(9) 1-Propionyloxyethyl 7-[2-(2-aminothiazol-4-yl)-2-carboxymethoxyiminoacetamido]-3-methylthio-3-cephem-4-carboxylate (syn isomer).

IR (Nujol): 1780, 1665 cm$^{-1}$.

NMR (DMSO-d6, δ), 1.04 (3H, t, J=7.0 Hz), 1.48 (3H, d, J=5.0 Hz), 2.36 (2H, q, J=7.0 Hz), 2.40 (3H, s), 3.86 (2H, s), 4,63 (2H, s), 5.22 (1H, d, J=5.0 Hz), 5.74 and 5.82 (total 1H, each 5.0 Hz and 8 Hz), 6.70-7.02 (1H, m), 6.90 (1H, s), 9.53 (1H, d, J=8.0 Hz).

(10) 1-Ethoxycarbonyloxyethyl 7-[2-(2-aminothiazol-4-yl)-2-carboxymethoxyiminoacetamido]-3-methylthio-3-cephem-4-carboxylate (syn isomer).

IR (Nujol): 1760 (br.) 1670 cm$^{-1}$.

NMR (DMSO-d6, δ): 1.22 (3H, t, J=7.0 Hz), 1.49 (3H, d, J=5.0 Hz), 2.39 (3H, s), 3.84 (2H, s), 4.17 (2H, q, J=7.0 Hz), 4.61 (2H, s), 5.18 (1H, d, J=4.0 Hz), 5.73-5.80 (total 1H, each d, J=4.0 Hz, 8.0 Hz), 6.79 (1H, m), 6.86 (1H, s), 9.47 (1H, d, J=8.0 Hz).

(11) 1-Ethoxycarbonyloxyethyl 7-[2-(2-amino-5-chlorothiazol-4-yl)-2-carboxymethoxyiminoacetamido]-3-methylthio-3-cephem-4-carboxylate (syn isomer).

IR (Nujol): 3250, 1760 (br.) 1670 1620 cm$^{-1}$.

NMR (DMSO-d6, δ), 1.22 (3H, t, J=7.0 Hz), 1.49 (3H, d, J=5.0 Hz), 2.39 (3H, s), 3.86 (2H, s), 4.19 (2H, q, J=7.0 Hz), 4.63 (2H, s), 5.16 (1H, d, J=4.0 Hz), 5.78 (1H, m), 6.81 (1H, m), 7.33 (2H, br-s), 9.39 (1H, d, J=8.0 Hz).

(12) (5-Methyl-2-oxo-1,3-dioxol-4-yl)methyl 7-[2-(2-aminothiazol-4-yl)-2-carboxymethoxyiminoacetamido]-3-methylthio-3-cephem-4-carboxylate (syn isomer).

IR (Nujol): 1810, 1765, 1665, 1615 cm$^{-1}$.

NMR (DMSO-d6, δ): 2.16 (3H, s), 2.35 (3H, s), 3.77 (2H, s), 4.56 (2H, s), 5.06 (2H, br., s), 5.14 (1H, d, J=4.0 Hz), 5.68 (1H, d-d, J=4.0 Hz and 8.0 Hz), 6.78 (1H, s), 9.41 (1H, d, J=8.0 Hz).

(13) 1-Propionyloxyethyl 7-[2-(5-amino-1,2,4-thiadiazol-3-yl)-2-(1-propionyloxyethoxycarbonylmethoxyimino)acetamido]-3-methylthio-3-cephem-4-carboxylate (syn isomer).

IR (Nujol): 1750(br.), 1675, 1610 cm$^{-1}$.

NMR (DMSO-d6, δ): 1.03 (6H, t, J=7 Hz), 1.45 (6H, d, J=5 Hz), 2.33 (4H, m), 2.37 (3H, s), 3.79 (2H, s), 4.75 (2H, s), 5.09 and 5.11 (total 1H, each 1H, J=4.0 Hz), 5.70 (1H, d-d, J=4.0 Hz and 8.0 Hz), 6.79 (2H, m), 8.04 (2H, br., s), 9.46 (1H, d, J=8.0 Hz).

(14) 1-Propionyloxyethyl 7-[2-(2-aminothiazol-4-yl)-2-carboxymethoxyiminoacetamido]-3-methylthio-3-cephem-4-carboxylate hydrochloride (syn isomer).

IR (Nujol): 1750 (br) 1670 1630 cm$^{-1}$.

NMR (DMSO-d6, δ), 1.02 (3H, t, J=7.0 Hz), 1.47 (3H, d, J=5.0 Hz), 2.35 (2H, q, J=7.0 Hz), 2.40 (3H, s), 3.86 (2H, s), 4.75 (2H, s), 5.23 (1H, d, J=4.0 Hz), 5.70 and 5.77 (total 1H, each d-d. J=4.0 Hz 8.0 Hz), 6.97 (1H, m), 7.13 (1H, s), 9.80 (1H, d, J=8.0 Hz).

(15) 1-Ethoxycarbonyloxyethyl 7-[2-(2-aminothiazol-4-yl)-2-carboxymethoxyiminoacetamido]-3-methylthio-3-cephem-4-carboxylate hydrochloride (syn isomer).

IR (Nujol): 1750 (br), 1650.

NMR (DMSO-d6, δ), 1.22 (3H, t, J=7.0 Hz), 1.49 (3H, d, J=5.0 Hz), 2.41 (3H, s), 3.87 (2H, s), 4.18 (2H, q, J=7.0 Hz), 4.75 (2H, s), 5.23 (1H, d, J=4.0 Hz), 5.71 (1H, d-d, J=4.0 Hz 8.0 Hz), 6.80 (1H, m), 7.15 (1H, s), 9.82 (1H, d, J=8.0 Hz).

(16) 7-[2-carboxymethoxyimino-2-(1,2,4-thiadiazol-3-yl)-acetamido]-3-methylthio-3-cephem-4-carboxylic acid (syn isomer).

IR (Nujol): 1760, 1700, 1660 cm$^{-1}$.

NMR (DMSO-d6, δ): 2.31 (3H, S), 3.75 (2H, S), 4.74 (2H, S), 5.14 (1H, d, J=5.0 HZ), 5.77 (1H, d-d, J=5.0 HZ, 8.0 HZ), 10.23 (1H, S), 9.61 (1H, d, J=8.0 HZ).

(17) Benzhydryl 7-[2-(t-butoxycarbonylmethoxyimino)-2-(1,2,4-thiadiazol-3-yl)acetamido]-3-methyethio-3-cephem-4-carboxylate (syn isomer).

IR (Nujol): 1760 (broad), 1680, 1630 cm$^{-1}$.

NMR (DMSO-d6, δ): 1.42 (9H, S), 2.30 (3H, S), 3.73 (2H, S), 4.71 (2H, S), 5.19 (1H, d, J=5.0 HZ), 5.88 (1H, d-d, J=5.0 HZ, 8.0 HZ), 6.82 (1H, S), 7.30 (10H, m), 9.67 (1H, d, J=8.0 HZ), 10.26 (1H, S).

What we claim is:

1. A cephem compound of the formula:

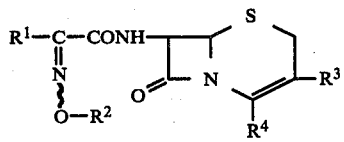

wherein
 $R^1$ is amino substituted thiazolyl selected from the group consisting of 2-aminothiazol-4-yl, 2-aminothiazol-5-yl, 4-aminothiazol-2-yl, 2-amino-5-halothiazol-4-yl, 2-amino-4-halothiazol-5-yl, and 4-amino-5-halothiazol-2-yl,
 protected amino substituted thiazolyl selected from said group,
 lower alkylamino substituted thiazolyl,
 amino substituted thiadiazolyl,
 protected amino substituted thiadiazolyl,
 amino substituted pyridyl,
 protected amino substituted pyridyl,
 furyl,
 thiazolyl,
 thiadiazolyl,
 phenyl, or
 naphthyl,
 $R^2$ is carboxy(lower)alkyl or protected carboxy(lower)alkyl,
 $R^3$ is lower alkylthio, and
 $R^4$ is carboxy or protected carboxy, and pharmaceutically acceptable salts thereof.

2. The compound of claim 1, wherein
 $R^1$ is amino substituted thiazolyl selected from said group,
 acylamino substituted thiazolyl selected from said group, wherein the acyl is selected from the group consisting of lower alkanoyl, lower alkoxycarbonyl, lower alkanesulfonyl, arenesulfonyl, aroyl, ar(lower)alkanoyl and ar(lower)alkoxycarbonyl,
 lower alkylamino substituted thiazolyl,
 amino substituted thiadiazolyl,
 acylamino substituted thiadiazolyl wherein the acyl is selected from said group,
 amino substituted pyridyl,
 acylamino substituted pyridyl wherein the acyl is selected from said group,
 furyl,
 thiazolyl,
 thiadiazolyl,
 phenyl, or
 naphthyl,
 $R^2$ is carboxy(lower)alkyl or esterified carboxy(lower)alkyl, and
 $R^4$ is carboxy or esterified carboxy.

3. Syn isomer of the compound of claim 2.

4. The compound of claim 3, wherein
 $R^1$ is 2-aminothiazol-4-yl,
 $R^2$ is carboxy(lower)alkyl, lower alkoxycarbonyl(lower)alkyl, or ar(lower)alkoxycarbonyl(lower)alkyl, and
 $R^4$ is carboxy.

5. The compound of claim 4, which is 7-[2-(2-aminothiazol-4-yl)-2-(carboxymethoxyimino)acetamido]-3-methylthio-3-cephem-4-carboxylic acid (syn isomer) or its hydrochloride.

6. The compound of claim 4, which is 7-[2-(2-aminothiazol-4-yl)-2-(1-carboxyethoxyimino)acetamido]-3-methylthio-3-cephem-4-carboxylic acid (syn isomer).

7. The compound of claim 4, which is 7-[2-(2-aminothiazol-4-yl)-2-methoxycarbonylmethoxyimino)acetamido)-3-methylthio-3-cephem-4-carboxylic acid (syn isomer).

8. The compound of claim 4, which is 7-[2-(2-aminothiazol-4-yl)-2-benzhydryloxycarbonylmethoxyiminoacetamido]-3-methylthio-3-cephem-4-carboxylic acid or its sodium salt (syn isomer).

9. The compound of claim 4, which is 7-[2-(2-aminothiazol-4-yl)-2-carboxymethoxyiminoacetamido]-3-ethylthio-3-cephem-4-carboxylic acid (syn isomer).

10. The compound of claim 4, which is 7-[2-(2-aminothiazol-4-yl)-2-(1-carboxyethoxyimino)acetamido]-3-ethylthio-3-cephem-4-carboxylic acid (syn isomer).

11. The compound of claim 4, which is 7-[2-(2-aminothiazol-4-yl)-2-carboxymethoxyiminoacetamido]-3-propylthio-3-cephem-4-carboxylic acid (syn isomer).

12. The compound of claim 3, wherein
 $R^1$ is 2-amino-5-halothiazol-4-yl,
 $R^2$ is carboxy(lower)alkyl, lower alkoxycarbonyl(lower)alkyl, or ar(lower)alkoxycarbonyl(lower)alkyl, and
 $R^4$ is carboxy.

13. The compound of claim 12, which is 7-[2-(2-amino-5-chlorothiazol-4-yl)-2-(carboxymethoxyiminoacetamido]-3-methylthio-3-cephem-4-carboxylic acid (syn isomer).

14. The compound of claim 12, which is 7-[2-(2-amino-5-chlorothiazol-4-yl)-2-carboxymethoxyiminoacetamido]-3-ethylthio-3-cephem-4-carboxylic acid (syn isomer).

15. The compound of claim 3, wherein
 $R^1$ is 5-amino-1,2,4-thiadiazol-3-yl,
 $R^2$ is carboxy(lower)alkyl, or lower alkoxycarbonyl(lower)alkyl, and
 $R^4$ is carboxy.

16. The compound of claim 15, which is 7-[2-(5-amino-1,2,4-thiadiazol-3-yl)-2-carboxymethoxyiminoacetamido]-3-methylthio-3-cephem-4-carboxylic acid (syn isomer).

17. The compound of claim 15, which is 7-[2-(5-amino-1,2,4-thiadiazol-3-yl)-2-carboxymethoxyiminoacetamido]-3-ethylthio-3-cephem-4-carboxylic acid (syn isomer).

18. The compound of claim 15, which is 7-[2-(5-amino-1,2,4-thiadiazol-3-yl)-2-(1-carboxyethoxyimino)acetamido]-3-ethylthio-3-cephem-4-carboxylic acid (syn isomer).

19. The compound of claim 3, wherein
R¹ is 6-aminopyridin-2-yl,
R² is carboxy(lower)alkyl or lower alkoxycarbonyl(lower)alkyl, and
R⁴ is carboxy.

20. The compound of claim 19, which is 7-[2-(6-aminopyridin-2-yl)-2-carboxymethoxyiminoacetamido]-3-ethylthio-3-cephem-4-carboxylic acid (syn isomer).

21. The compound of claim 19, which is 7-[2-(6-aminopyridin-2-yl)-2-carboxymethoxyiminoacetamido]-3-methylthio-3-cephem-4-carboxylic acid (syn isomer).

22. The compound of claim 3, wherein
R¹ is 2-lower alkylaminothiazol-4-yl, furyl, thiazolyl, 1,2,4-thiadiazolyl, 1,2,5-thiadiazolyl, phenyl, or naphthyl,
R² is carboxy(lower)alkyl or lower alkoxycarbonyl(lower)alkyl, and
R⁴ is carboxy.

23. The compound of claim 3, wherein
R¹ is 2-lower alkanoylaminothiazol-4-yl, 2-lower alkanoylamino-5-halothiazol-4-yl, 5-lower alkanoylamino-1,2,4-thiadiazol-3-yl, or 6-lower alkanoylaminopyridin-2-yl,
R² is carboxy(lower)alkyl, lower alkoxycarbonyl(lower)alkyl, or ar(lower)alkoxycarbonyl(lower)alkyl, and
R⁴ is carboxy or ar(lower)alkoxycarbonyl.

24. The compound of claim 3, wherein
R² is carboxy(lower)alkyl, lower alkoxycarbonyl(lower)alkyl, ar(lower)alkoxycarbonyl(lower)alkyl, lower alkanoyloxy(lower)alkoxycarbonyl(lower)alkyl, lower alkoxycarbonyloxy(lower)alkoxycarbonyl(lower)alkyl, or (5-lower alkyl-2-oxo-1,3-dioxol-4-yl)(lower)alkoxycarbonyl(lower)alkyl, and
R⁴ is ar(lower)alkoxycarbonyl, lower alkanoyloxy(lower)alkoxycarbonyl, lower alkoxycarbonyloxy(lower)alkoxycarbonyl, or (5-lower alkyl-2-oxo-1,3-dioxol-4-yl)(lower)alkoxycarbonyl.

25. The compound of claim 24, wherein
R¹ is 2-aminothiazol-4-yl, 2-amino-5-halothiazol-4-yl or 5-amino-1,2,4-thiadiazol-3-yl,
R² is carboxy(lower)alkyl, lower alkanoyloxy(lower)alkoxycarbonyl(lower)alkyl, lower alkoxycarbonyloxy(lower)alkoxycarbonyl(lower)alkyl, or (5-lower alkyl-2-oxo-1,3-dioxol-4-yl)(lower)alkoxycarbonyl(lower)alkyl, and
R⁴ is lower alkanoyloxy(lower)alkoxycarbonyl, lower alkoxycarbonyloxy(lower)alkoxycarbonyl or (5-lower alkyl-2-oxo-1,3-dioxol-4-yl)(lower)alkoxycarbonyl.

26. The compound of claim 25, which is pivaloyloxymethyl 7-[2-(2-aminothiazol-4-yl)-2-carboxymethoxyiminoacetamido]-3-methylthio-3-cephem-4-carboxylate (syn isomer) or its hydrochloride.

27. The compound of claim 25, which is 1-propionyloxyethyl 7-[2-(2-aminothiazol-4-yl)-2-carboxymethoxyiminoacetamido]-3-methylthio-3-cephem-4-carboxylate (syn isomer) or its hydrochloride.

28. The compound of claim 25, which is 1-ethoxycarbonyloxyethyl 7-[2-(2-aminothiazol-4-yl)-2-carboxymethoxyiminoacetamido]-3-methylthio-3-cephem-4-carboxylate (syn isomer) or its hydrochloride.

29. The compound of claim 25, which is (5-methyl-2-oxo-1,3-dioxol-4-yl)methyl 7-[2-(2-aminothiazol-4-yl)-2-carboxymethoxyiminoacetamido]-3-methylthio-3-cephem-4-carboxylate (syn isomer) or its hydrochloride.

30. The compound of claim 25, which is 1-ethoxycarbonyloxyethyl 7-[2-(2-amino-5-chlorothiazol-4-yl)-2-carboxymethoxyiminoacetamido]-3-methylthio-3-cephem-4-carboxylate (syn isomer) or its hydrochloride.

31. The compound of claim 25, which is 1-propionyloxyethyl 7-[2-(5-amino-1,2,4-thiadiazol-3-yl)-2-(1-propionyloxyethoxycarbonylmethoxyimino)acetamido]-3-methylthio-3-cephem-4-carboxylate (syn isomer) or its hydrochloride.

32. A cephem compound of the formula:

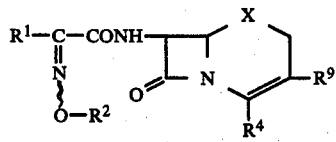

wherein
X is —S— or

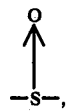

R¹ is amino substituted thiazolyl selected from the group consisting of 2-aminothiazol-4-yl, 2-aminothiazol-5-yl, 4-aminothiazol-2-yl, 2-amino-5-halothiazol-4-yl, 2-amino-4-halothiazol-5-yl, and 4-amino-5-halothiazol-2-yl,
protected amino substituted thiazolyl selected from said group,
lower alkylamino substituted thiazolyl,
amino substituted thiadiazolyl,
protected amino substituted thiadiazolyl,
amino substituted pyridyl,
protected amino substituted pyridyl,
furyl,
thiazolyl,
thiadiazolyl,
phenyl, or
naphthyl,
R² is carboxy(lower)alkyl or protected carboxy(lower)alkyl,
R⁴ is carboxy or protected carboxy, and
R⁹ is a group of the formula:

—O—SO₂—R⁷ wherein
R⁷ is lower alkyl, phenyl, or phenyl substituted with lower alkyl, halogen or nitro, or lower alkylthio, provided that X is

when $R^9$ is lower alkylthio, and a salt thereof.

33. A pharmaceutical composition comprising an effective amount of a compound of claim 1 in association with a pharmaceutically acceptable substantially non-toxic carrier or excipient.

34. A method for producing a pharmaceutical composition which comprises mixing an effective amount of a compound of claim 1 as an active ingredient with an inert carrier.

* * * * *